United States Patent
Bencke et al.

(10) Patent No.: US 12,023,445 B2
(45) Date of Patent: Jul. 2, 2024

(54) STANDALONE PATIENT HEAT AND MOISTURE EXCHANGER

(71) Applicant: RESMED PTY LTD, Bella Vista (AU)

(72) Inventors: James McKensey Bencke, Sydney (AU); Eric Leung, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 18/017,651

(22) PCT Filed: Jul. 22, 2021

(86) PCT No.: PCT/AU2021/050789
§ 371 (c)(1),
(2) Date: Jan. 23, 2023

(87) PCT Pub. No.: WO2022/016223
PCT Pub. Date: Jan. 27, 2022

(65) Prior Publication Data
US 2023/0211110 A1    Jul. 6, 2023

(30) Foreign Application Priority Data
Jul. 24, 2020   (AU) ................................ 2020902601

(51) Int. Cl.
*A61M 16/10* (2006.01)
*A61M 16/00* (2006.01)
*A61M 16/06* (2006.01)

(52) U.S. Cl.
CPC .... *A61M 16/1045* (2013.01); *A61M 16/0066* (2013.01); *A61M 16/0616* (2014.02); *A61M 16/0633* (2014.02); *A61M 16/0688* (2014.02)

(58) Field of Classification Search
CPC ........... A62B 9/003; A62B 9/06; A62B 23/06; A61M 15/085; A61M 16/0666–0677; A61M 16/1045
See application file for complete search history.

(56) References Cited

U.S. PATENT DOCUMENTS

| | | | | |
|---|---|---|---|---|
| 2,161,607 A | * | 6/1939 | Anderson | A62B 23/06 |
| | | | | 128/206.18 |
| 3,451,392 A | * | 6/1969 | Cook | A62B 23/06 |
| | | | | 55/DIG. 35 |

(Continued)

FOREIGN PATENT DOCUMENTS

| | | |
|---|---|---|
| CN | 103316408 B | 2/2015 |
| JP | 2002-253671 | 9/2002 |

(Continued)

OTHER PUBLICATIONS

"*Respiratory Physiology*", by John B. West, Lippincott Williams & Wilkins, 9th edition published 2012 (8 pages).

(Continued)

*Primary Examiner* — Valerie L Woodward
(74) *Attorney, Agent, or Firm* — Nixon & Vanderhye P.C.

(57) ABSTRACT

A heat and moisture exchanger (HME) for engaging a patient's nose while retrofit into a plenum chamber of a patient interface. The HME includes a frame configured to couple to a ridge of the patient's nose, and a cradle coupled to the frame. The cradle is configured to be positioned proximate to the patient's nares. The HME also includes an HME material coupled to the cradle. The HME material is configured to retain moisture exhaled by the patient. Air is configured to pass through the HME material when entering and exiting the patient's nares. The HME engages and is secured to the patient's nose independently of any other structure.

35 Claims, 60 Drawing Sheets

(56) References Cited

U.S. PATENT DOCUMENTS

| | | | |
|---|---|---|---|
| 4,782,832 A | | 11/1988 | Trimble et al. |
| 4,944,310 A | | 7/1990 | Sullivan |
| 5,687,715 A | | 11/1997 | Landis |
| 5,890,491 A | * | 4/1999 | Rimkus ............... A62B 23/06 |
| | | | 128/204.12 |
| 6,354,293 B1 | * | 3/2002 | Madison ........... A61M 16/1085 |
| | | | 128/207.18 |
| 6,532,959 B1 | | 3/2003 | Berthon-Jones |
| 6,581,594 B1 | | 6/2003 | Drew et al. |
| 7,866,944 B2 | | 1/2011 | Kenyon et al. |
| 8,636,479 B2 | | 1/2014 | Kenyon et al. |
| 8,638,014 B2 | | 1/2014 | Sears et al. |
| 8,733,349 B2 | | 5/2014 | Bath et al. |
| 2004/0020489 A1 | * | 2/2004 | Gillespie ............... A62B 23/06 |
| | | | 128/206.18 |
| 2005/0051170 A1 | * | 3/2005 | Koo ..................... A62B 23/06 |
| | | | 128/206.11 |
| 2007/0221219 A1 | * | 9/2007 | Christy .............. A61M 16/0666 |
| | | | 606/198 |
| 2007/0283963 A1 | * | 12/2007 | Sims ..................... A62B 7/10 |
| | | | 128/205.27 |
| 2008/0087286 A1 | * | 4/2008 | Jones ................... A62B 23/06 |
| | | | 128/206.11 |
| 2009/0007919 A1 | * | 1/2009 | Dolezal .................. A62B 7/10 |
| | | | 128/206.11 |
| 2009/0044808 A1 | | 2/2009 | Guney et al. |
| 2009/0050156 A1 | | 2/2009 | Ng et al. |
| 2010/0000534 A1 | | 1/2010 | Kooij et al. |
| 2013/0186394 A1 | * | 7/2013 | Hallett .............. A61M 16/0057 |
| | | | 128/205.24 |
| 2014/0276177 A1 | * | 9/2014 | Brambilla ............. A61M 16/06 |
| | | | 128/201.13 |
| 2016/0158474 A1 | * | 6/2016 | Harrison ........... A61M 16/0683 |
| | | | 128/205.28 |
| 2016/0158475 A1 | * | 6/2016 | Harrison ........... A61M 16/0057 |
| | | | 128/205.12 |
| 2018/0147424 A1 | * | 5/2018 | Ni .......................... A62B 23/06 |
| 2018/0193201 A1 | * | 7/2018 | Singh ..................... A62B 23/06 |
| 2018/0221618 A1 | * | 8/2018 | Strauss ................ A61K 31/045 |
| 2018/0250486 A1 | | 9/2018 | Amarasinghe et al. |

FOREIGN PATENT DOCUMENTS

| | | |
|---|---|---|
| JP | 2002-253671 A | 9/2002 |
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | 2007/092634 A2 | 8/2007 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | 2021/034757 | 2/2021 |

OTHER PUBLICATIONS

International Search Report dated Aug. 31, 2021 issued in International Application No. PCT/AU2021/050789 (5 pages).

Written Opinion of the International Searching Authority dated Aug. 31, 2021 issued in International Application No. PCT/AU2021/050789 (6 pages).

International Preliminary Report on Patentability dated Oct. 6, 2022 issued in International Application No. PCT/AU2021/050789 (7 Pages).

Notification of Transmittal of International Preliminary Report on Patentability dated Oct. 6, 2022 issued in International Application No. PCT/AU2021/050789 (1 Page).

Written Opinion of the International Preliminary Examining Authority dated Jun. 20, 2022 issued in International Application No. PCT/AU2021/050789 (5 Pages).

Notification Concerning Availability of the Publication of the International Application dated Jan. 27, 2022 issued in International Application No. PCT/AU2021/050789 (1 Page).

Extended European Search Report dated Nov. 27, 2023 issued in European Application No. 21846612.6 (10 pages).

* cited by examiner

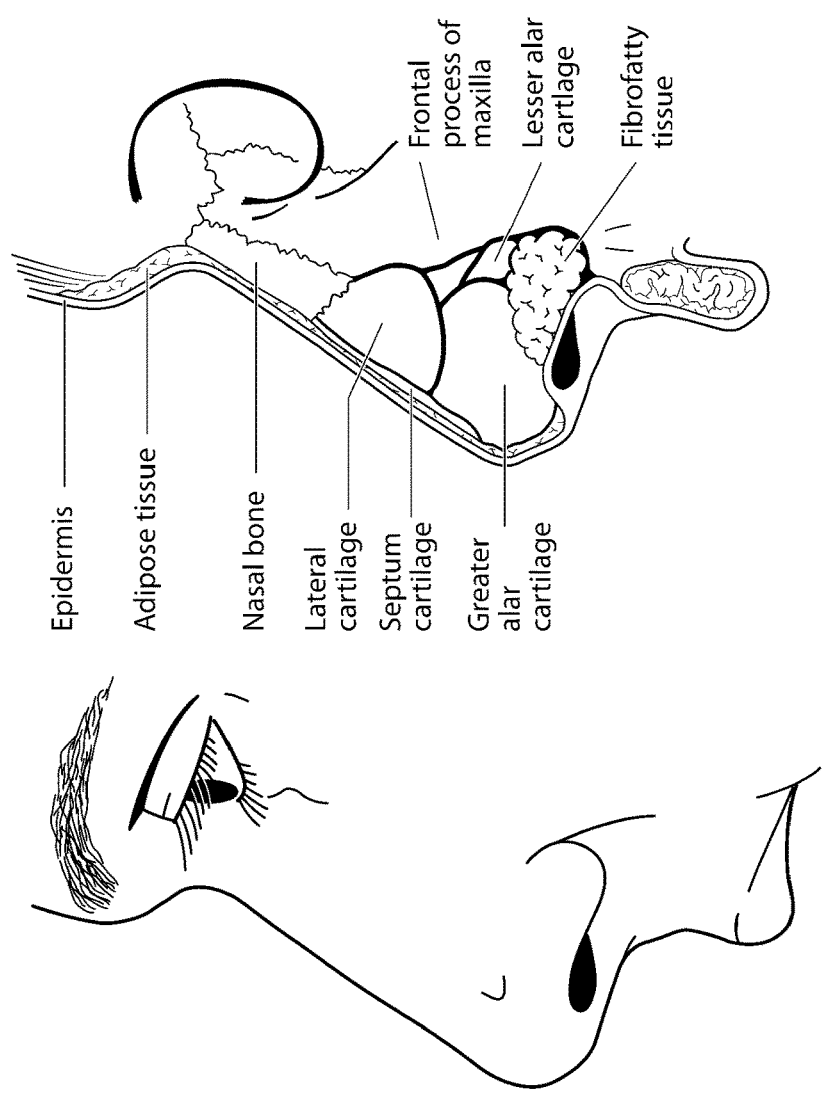
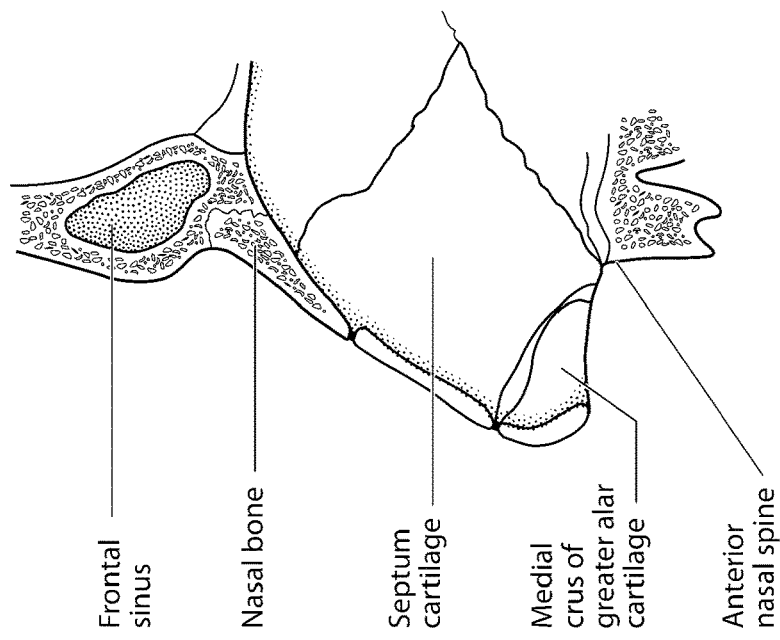
FIG. 2G
FIG. 2H
FIG. 2I

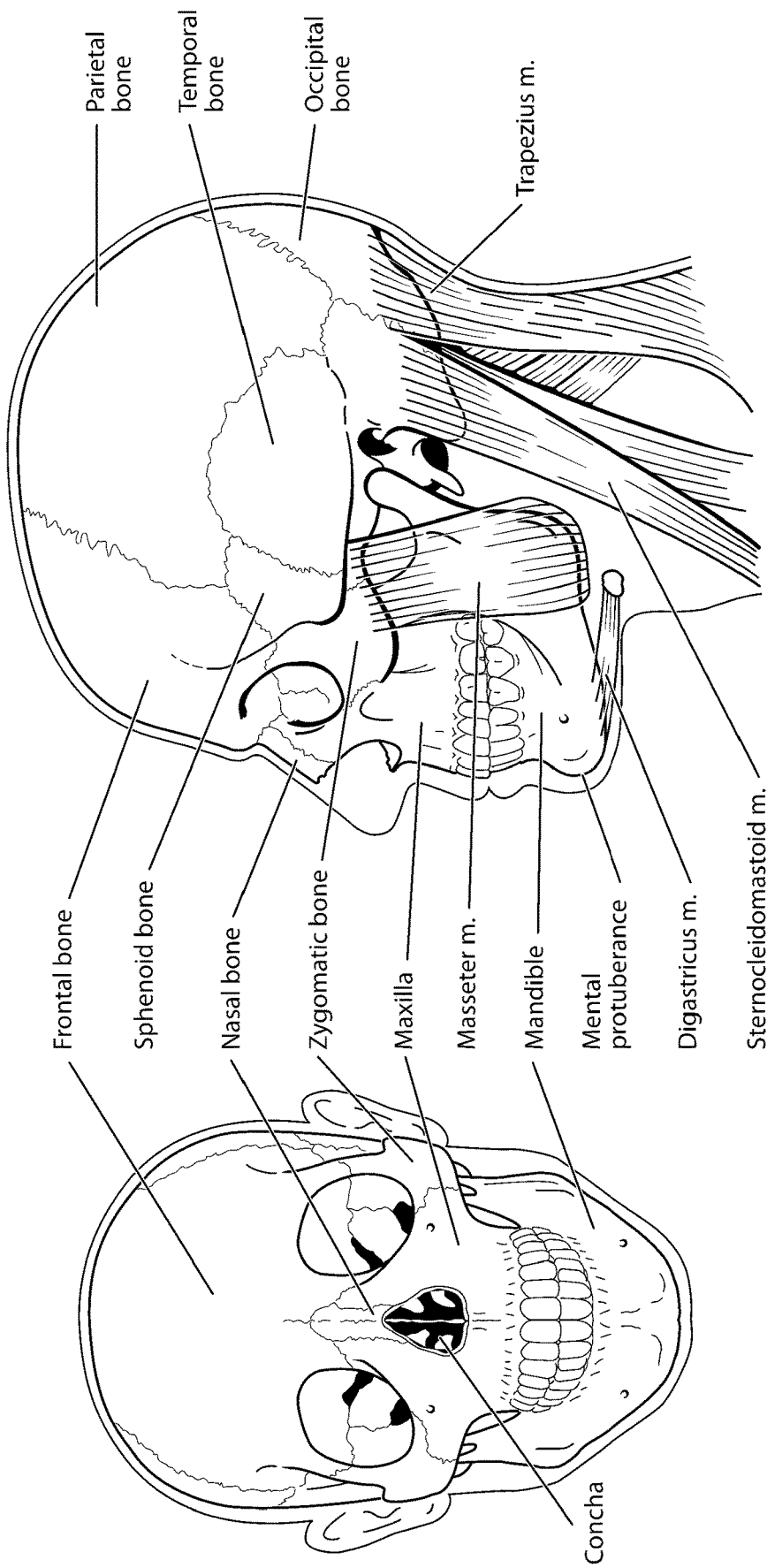

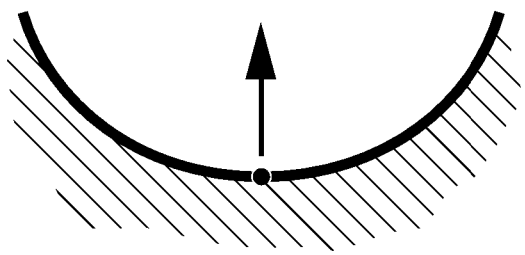
FIG. 3B — Relatively Large Positive Curvature
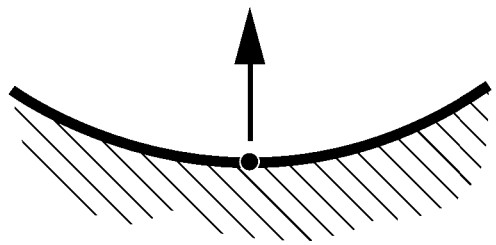
FIG. 3C — Relatively Small Positive Curvature
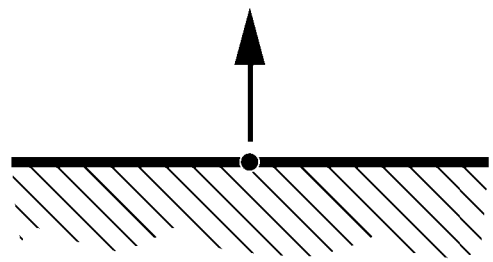
FIG. 3D — Zero Curvature
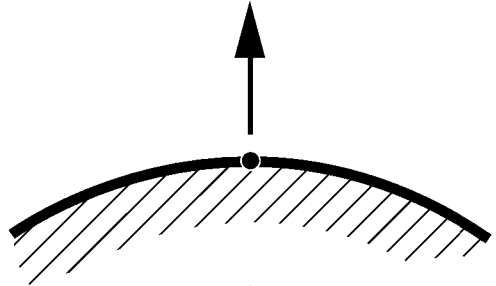
FIG. 3E — Relatively Small Negative Curvature
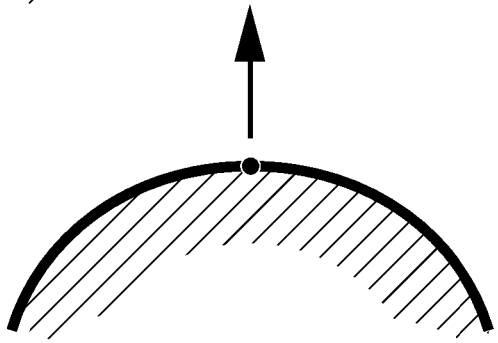
FIG. 3F — Relatively Large Negative Curvature

Left-hand rule

Right-hand rule

Left ear helix

Right-hand helix
Right-hand positive

Right ear helix

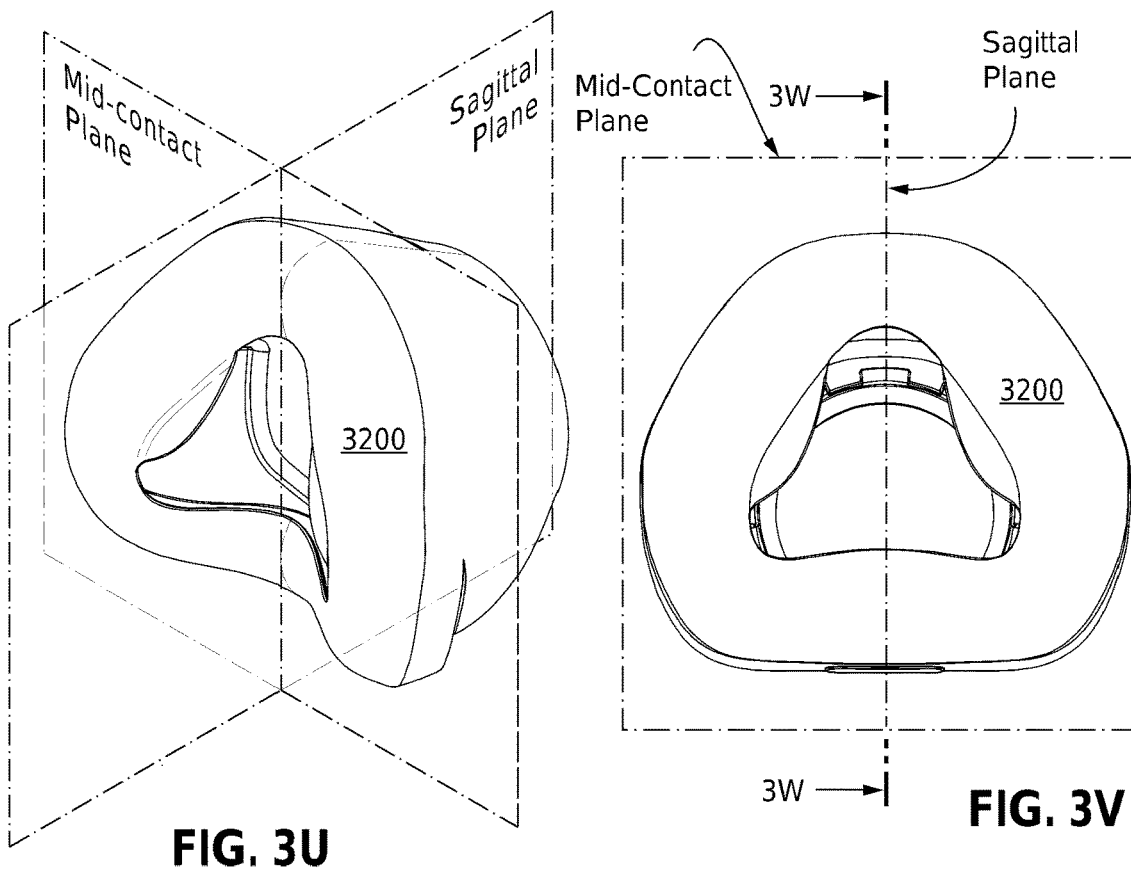
FIG. 3U
FIG. 3V
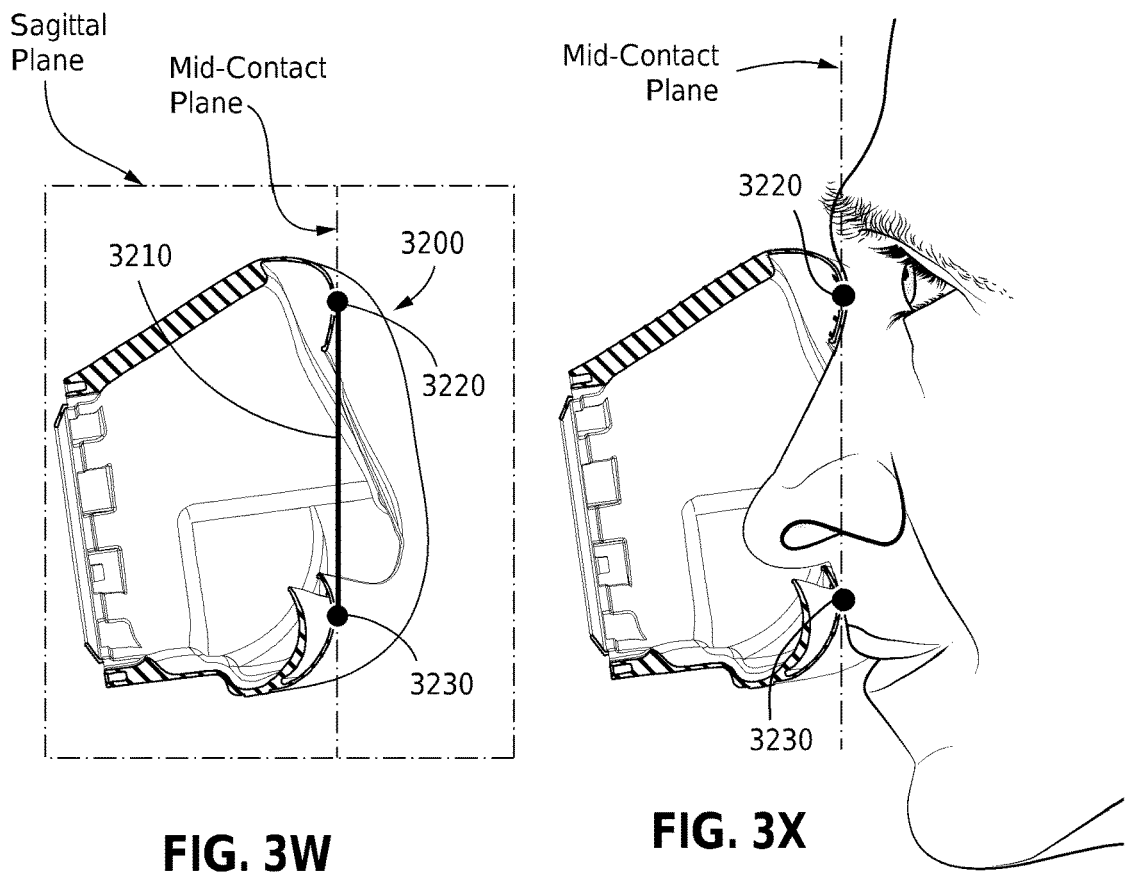
FIG. 3W
FIG. 3X

STANDALONE PATIENT HEAT AND MOISTURE EXCHANGER

CROSS-REFERENCE TO RELATED APPLICATION

This application is the U.S. national phase of International Application No. PCT/AU2021/050789 filed Jul. 22, 2021 which designated the U.S. and claims the benefit of Australian Provisional Application No. 2020902601, filed Jul. 24, 2020, the entire contents of each of which are incorporated herein by reference.

This application claims the benefit of Australian Provisional Application No. 2020902601, filed Jul. 24, 2020, the entire contents of which are incorporated herein by reference in its entirety.

BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes.

To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H41™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.5 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.6 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.7 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 $cmH_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH₂O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a heat and moisture exchanger (HME) configured to directly engage a patient's nose.

Another aspect of one form of the present technology is an HME comprising a frame configured to couple to a ridge of the patient's nose, a cradle coupled to the superior bar and configured to be positioned proximate to the patient's nares, in use, and an HME material coupled to the cradle, the HME material configured to retain moisture exhaled by the patient.

Another aspect of one form of the present technology is an HME comprising a frame configured to couple to a ridge of the patient's nose, a cradle coupled to the superior bar and configured to be positioned proximate to the patient's nares, in use, and an HME material coupled to the cradle, the HME material configured to retain moisture exhaled by the patient, wherein air is configured to pass through the HME material when entering and exiting the patient's nares, and wherein the HME engages and is secured to the patient's nose independently of any other structure.

Another aspect of one form of the present technology is an HME comprising a frame configured to couple to the patient's nose, a cradle coupled to the frame and configured to be positioned proximate to the patient's nares, in use, and an HME material coupled to the cradle and spaced apart from the patient's nares so as to form a gap between the HME material and the patient's nares.

Another aspect of one form of the present technology is an HME comprising a frame configured to couple to the patient's nose, a cradle coupled to the frame and configured to be positioned proximate to the patient's nares, in use, and an HME material coupled to the cradle and spaced apart from the patient's nares so as to form a gap between the HME material and the patient's nares, wherein the HME engages and is secured to the patient's nose independently of any other structure.

In certain forms, the frame is coupled to a ridge of the patient's nose.

In certain forms, the frame is positioned adjacent to the lateral nasal cartilage and/or to the greater alar cartilage of the patient's nose.

In certain forms, the frame is shaped like an annulus sector and is coupled to the cradle and configured to engage a septum of the patient's nose.

In certain forms, the frame is pivotable relative to the cradle.

In certain forms, the frame includes a curvature that substantially corresponds to a corvature of the patient's columella.

In certain forms, the cradle is ring shaped.

In certain forms, the HME material is formed as a plug.

In certain forms, a holder is configured to removably receive the plug.

In certain forms, the holder is removably received within the cradle.

In certain forms, the plug has a conical shape, a frusto-conical shape, or a cylindrical shape.

In certain forms, the frame is coupled to a nasal ala of the patient's nose.

In certain forms, the frame is inwardly biased and configured to clamp against a surface of the patient's nose.

In certain forms, the cradle has a concave curvature with respect to the entrance of the patient's nares.

In certain forms, the cradle is disposed substantially orthogonal with respect to the patient's upper lip.

In certain forms, the cradle is flexible or semi-rigid and can be adjusted by a patient to change the shape.

In certain forms, the HME material is removable from the cradle.

In certain forms, the HME material is permanently affixed to the cradle.

In certain forms, at least some air exhaled through the patient's nares passes through the HME material so that at least some moisture in the exhaled air is collected in the HME material.

In certain forms, at least one flow path of air into and out of the patient's nares does not travel through the HME material.

In certain forms, the cradle includes a first section and a second section, separate pieces of HME material are used to cover each section.

In certain forms, the first section is spaced apart from the second section.

In certain forms, the HME material is a foam and/or a paper.

In certain forms, the HME further includes a rib shaped with a substantially similar curvature to the patient's upper lip.

In certain forms, the HME further includes a middle bar connected between the cradle and rib, the middle bar providing support to the HME material.

In certain forms, the HME material is coupled to the cradle with an adhesive.

In certain forms, a gauze material is disposed between the HME material and the patient's skin.

In certain forms, the gauze material is coupled to the HME material with an adhesive.

In certain forms, the cradle extends from the upper lip to the pronasale.

In certain forms, the cradle extends generally parallel with respect to the patient's upper lip, the cradle extending from the pronasale to the patient's lower lip so that at least some air entering and/or exiting the patient's mouth passes through the HME material.

In certain forms, the HME material is disposable after a single use, and the cradle is reusable.

In certain forms, the cradle is secured to the patient without the use of adhesives.

Another aspect of one form of the present technology is a patient interface comprising a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient; a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head; and the HME material of any of the previous forms.

Another aspect of one form of the present technology is a patient interface comprising a plenum chamber pressurisable to a therapeutic pressure of at least 6 cmH20 above ambient air pressure, said plenum chamber including a plenum chamber inlet port sized and structured to receive a flow of air at a therapeutic pressure for breathing by a patient; a seal-forming structure constructed and arranged to form a seal with a region of a patient's face surrounding an entrance to a patient's airways for sealed delivery of a flow of air at the therapeutic pressure of at least 6 cmH20 above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head; and a heat and moisture exchanger (HME) configured to be positioned within the plenum chamber in use as a retrofit, the HME comprising, an HME material, the HME material configured to retain moisture exhaled by the patient, a cradle supporting the HME material, wherein the cradle supports the HME material apart from the nares so that the HME material does not completely cover the entrance to the nares, in use, wherein the cradle is not engaged to the plenum chamber and/or the seal-forming structure, and wherein the cradle is configured to form a complementary shape with the plenum chamber.

Another aspect of one form of the present technology is a patient interface comprising a plenum chamber pressurisable to a therapeutic pressure of at least 6 cmH20 above ambient air pressure, said plenum chamber including a plenum chamber inlet port sized and structured to receive a flow of air at a therapeutic pressure for breathing by a patient; a seal-forming structure constructed and arranged to form a seal with a region of a patient's face surrounding an entrance to a patient's airways for sealed delivery of a flow of air at the therapeutic pressure of at least 6 cmH20 above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; a positioning and stabilizing structure to provide a force to hold a seal-forming structure in a therapeutically effective position on a patient's head; and a heat and moisture exchanger (HME) configured to be coupled to the patient's nose in use as a retrofit, the HME comprising, a cradle, an HME material coupled to the cradle without contacting the patient's nares, wherein the cradle is coupled to the patient's nose prior to the seal-forming structure forming the seal with a region of a patient's face surrounding an entrance to a patient's airways, and wherein the cradle is configured to form a complementary shape with the plenum chamber in order to fit at least partially inside of the plenum chamber.

In certain forms, the flow of air is configured to at least partially pass through the HME material after entering the plenum chamber and prior to reaching the patient's nares.

In certain forms, air entering the plenum chamber through the plenum chamber inlet port is directed into the HME.

Another aspect of one form of the present technology is a patient interface comprising: a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient; a seal-forming structure constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilizing structure to provide a force to hold a seal-forming structure in a therapeutically effective position on a patient's head.

Another aspect of one form of the present technology comprises a heat and moisture exchanger (HME) configured to engage the patient's nose while retrofitted into a plenum chamber of a patient interface, the HME comprising: a frame configured to engage the patient's septum in use;
a cradle coupled to the frame and including at least one opening, the
a cradle configured to be positioned proximate to and outside of the patient's nares, in use; and
an HME material positioned over and/or within the at least one opening, the HME material configured to be spaced apart from the patient's nares so as to form a gap between the HME material and the patient's nares; and
wherein the HME is configured to engage and secure to the patient's nose independently of any other structure.

In certain forms the frame is shaped like an annulus sector, and wherein free ends of the frame are configured to contact the patient's septum, in use.

In certain forms the free ends are spherical in shape.

In certain forms the frame is S-shaped, and wherein a negative domed section contacts the patient's septum, in use.

In certain forms the frame is pivotable relative to the cradle.

In certain forms the cradle is ring-shape.

In certain forms the cradle includes a first ring and a second ring spaced apart from the first ring, wherein the first ring and the second ring each include an opening of the at least one opening.

In certain forms the HME material includes a first sheet and a second sheet, the first sheet positioned over the opening of the first ring and the second sheet positioned over the opening of the second ring.

In certain forms the first sheet and the second sheet are removably connected to the cradle with an adhesive.

In certain forms the first sheet is connected over a superior surface of the first ring and the second sheet is connected to a superior surface over the second ring.

In certain forms a holder is removably positionable through the opening of the first ring and the opening of the second ring.

In certain forms the holder includes a first compartment positionable through the opening of the first ring, a second compartment positionable through the second opening, and a linking member connecting the first compartment to the second compartment, wherein the HME material at least partially fills the first compartment and the second compartment.

In certain forms the first compartment and the second compartment are conical or frustoconical in shape.

In certain forms the HME material includes a first plug removably positionable within the first compartment and a second plug removably positionable within the second compartment.

In certain forms the first plug and the second plug are conically shaped, frustoconically shaped, or cylindrically shaped.

In certain forms the holder extends completely through the opening of the first ring and the opening of the second ring.

In certain forms the cradle includes a posterior bar, an anterior bar, and a pair of outer support bars that form a rectangular shape, the posterior bar configured to be positioned proximate to the patient's lip superior in use.

In certain forms the cradle includes a central support bar extending between the posterior bar and the anterior bar and spaced apart from the pair of outer support bars, the central support bar dividing the at least one opening into a first opening and a second opening.

In certain forms the HME material is a single sheet positioned to extend between the pair of outer support bars and cover the first opening, the second opening, and the central support bar.

In certain forms the HME material includes a first sheet positioned to extend between a first outer support bar of the pair of outer support bars and cover the first opening, and a second sheet positioned to extend between a second outer support bar of the pair of outer support bars and cover the second opening.

In certain forms the HME material is coupled to the cradle using an adhesive.

In certain forms the frame is connected to the cradle with a snap-fit.

In certain forms the cradle includes a positively curved surface extending between an upper edge and a lower edge, the upper edge configured to be positioned proximate to the patient's pronasale, and the lower edge configured to be positioned proximate to the patient's lip superior.

In certain forms the at least one opening includes a first opening and a second opening.

In certain forms the HME material is a single sheet that is positioned to cover the first opening and the second opening.

In certain forms the HME material includes a first sheet that is positioned to cover the first opening and a second sheet that is positioned to cover the second opening.

In certain forms the HME material is coupled to the cradle using an adhesive.

In certain forms a holder is removably positionable through the opening of the first ring and the opening of the second ring.

In certain forms the holder includes a first compartment positionable through the opening of the first ring, a second compartment positionable through the second opening, and a linking member connecting the first compartment to the second compartment, wherein the HME material at least partially fills the first compartment and the second compartment.

In certain forms the first compartment and the second compartment are conical or frustoconical in shape.

In certain forms the HME material includes a first plug removably positionable within the first compartment and a second plug removably positionable within the second compartment.

In certain forms the first plug and the second plug are conically shaped, frustoconically shaped, or cylindrically shaped.

In certain forms the holder extends completely through the opening of the first ring and the opening of the second ring.

In certain forms the frame is connected to the cradle with a snap-fit.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of one form of the present technology is a method of securing a patient interface for use with a CPAP device to a patient's head, the method comprising: attaching a cradle to a patient's nose, the cradle supporting an (HME) material; and securing a plenum chamber to the patient's head subsequent to attaching the cradle to the patient's nose; wherein the cradle is not secured to the plenum chamber.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

4.1 Respiratory Therapy Systems

4.2 Respiratory System and Facial Anatomy

Figure 1A:
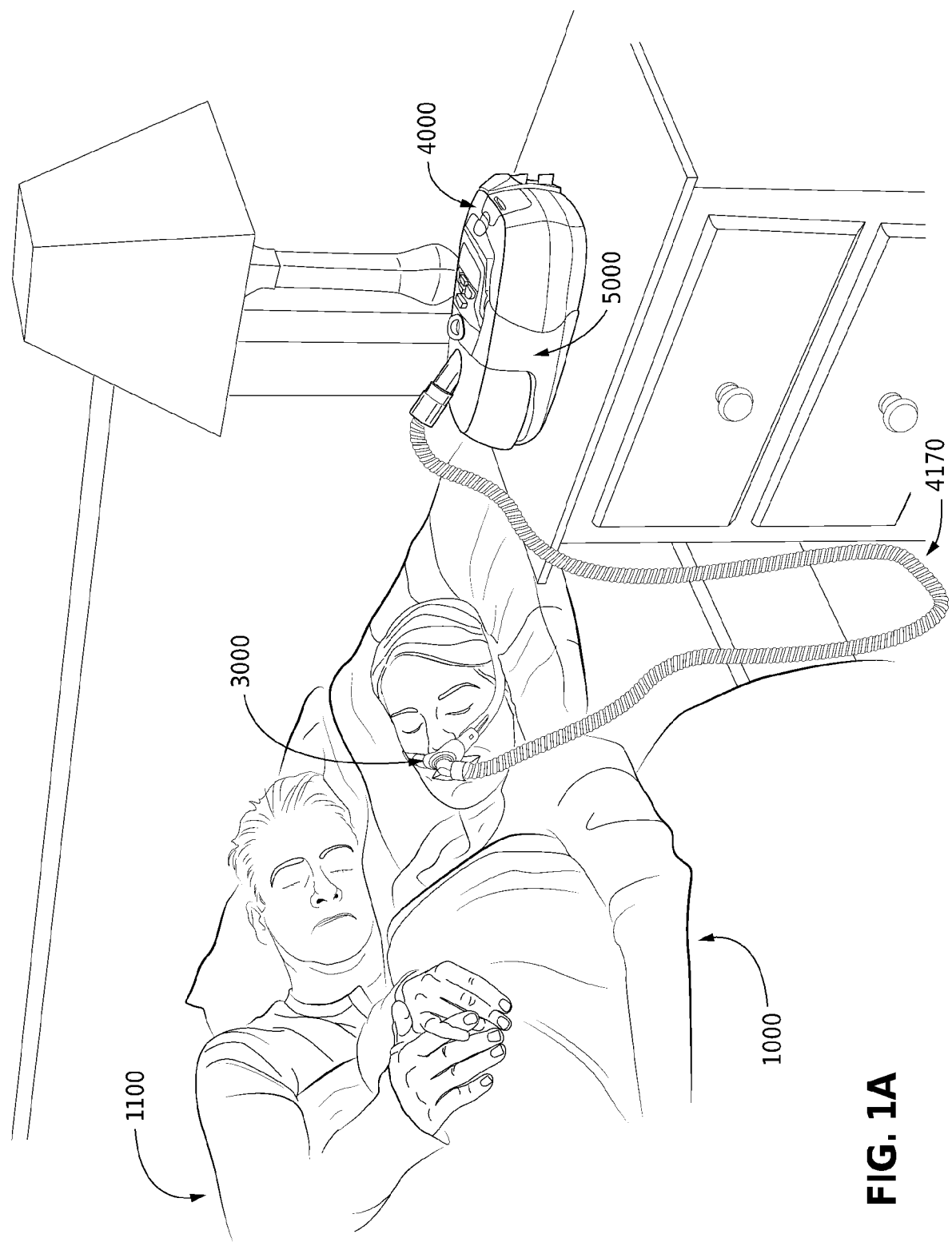
FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.
Figure 1B:
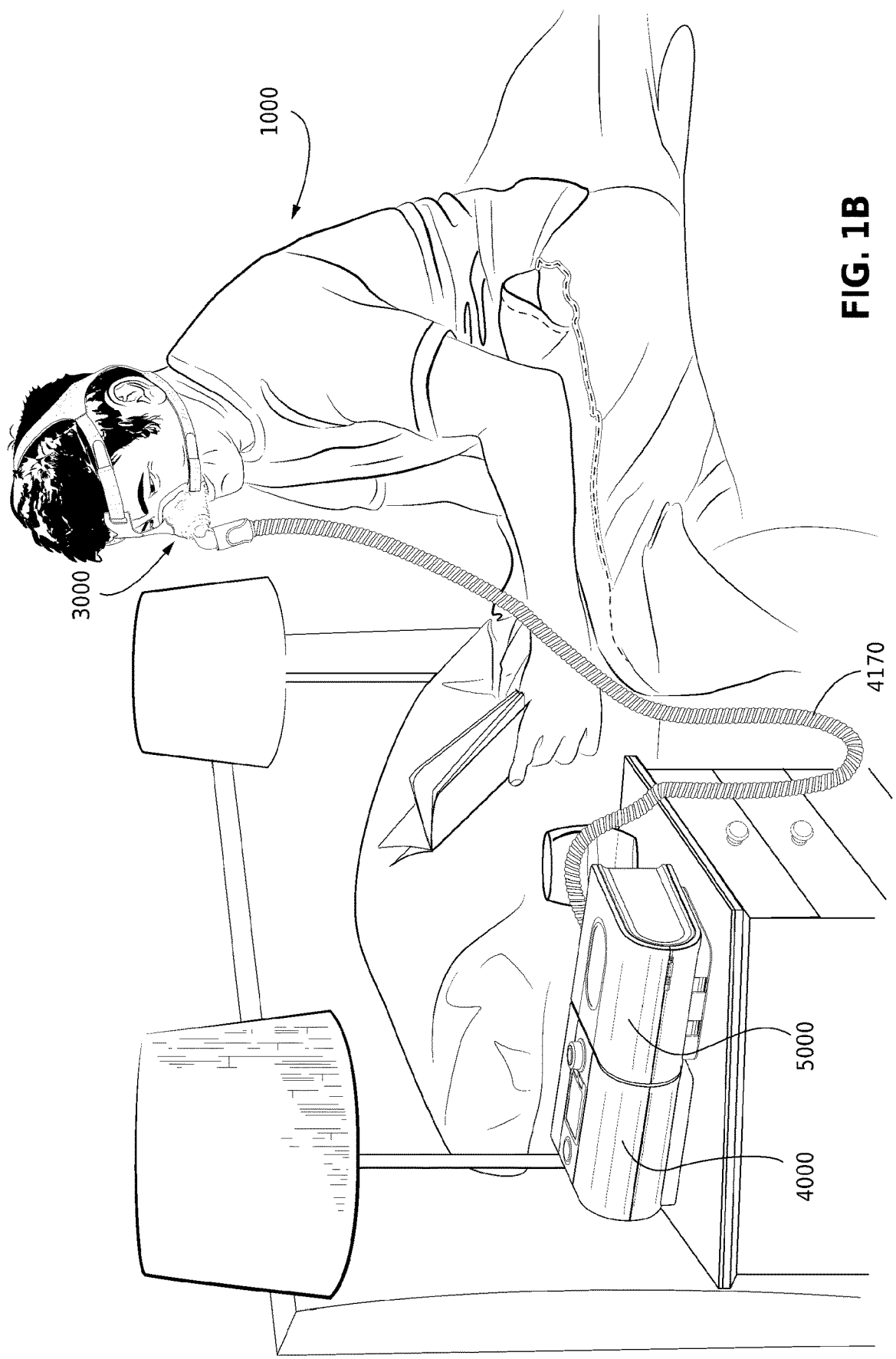
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
Figure 1C:
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.
Figure 2A:
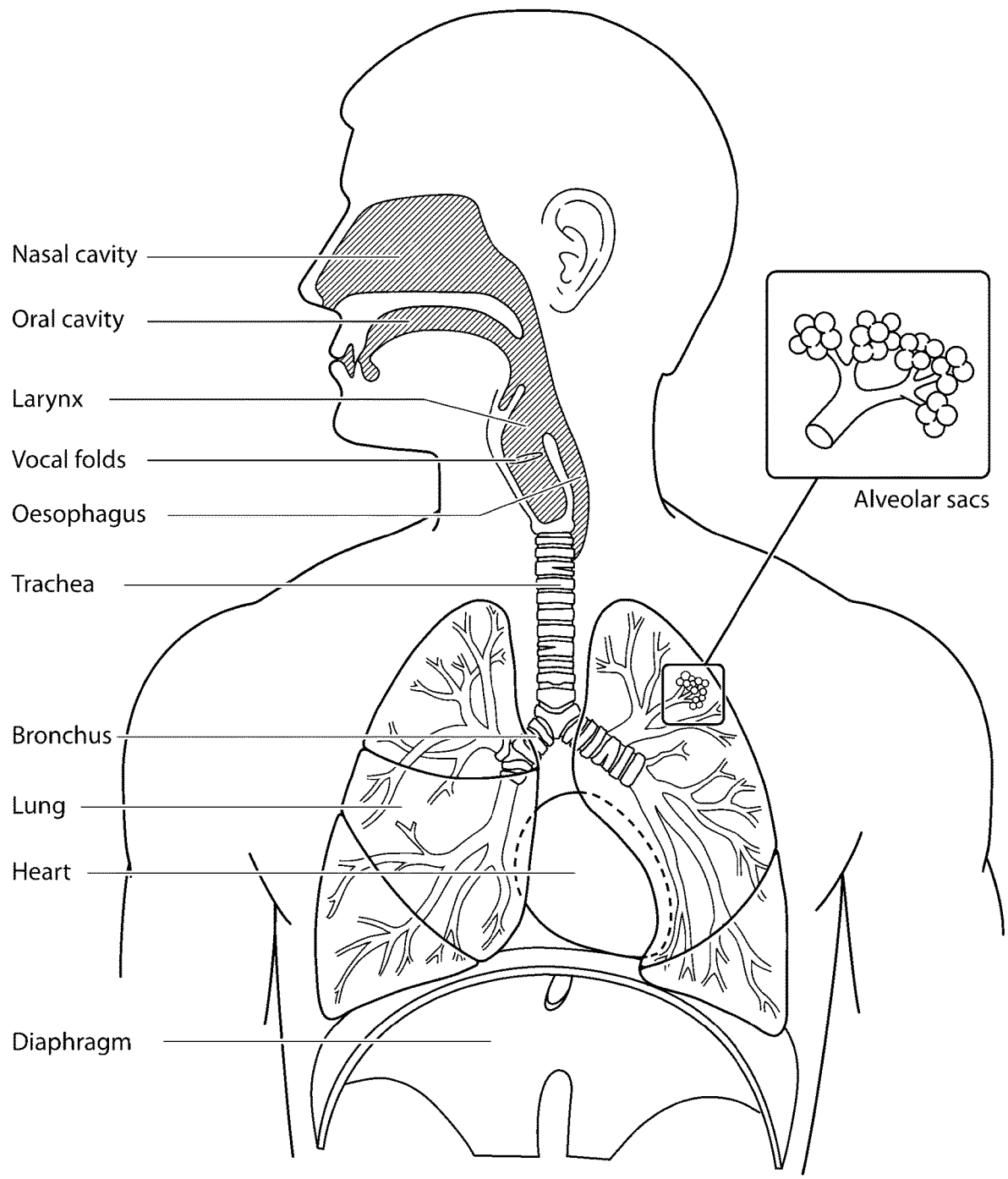

FIG. 2A shows an overview of a human respiratory system including the nasal and oral cavities, the larynx, vocal folds, oesophagus, trachea, bronchus, lung, alveolar sacs, heart and diaphragm.

Figure 2B:
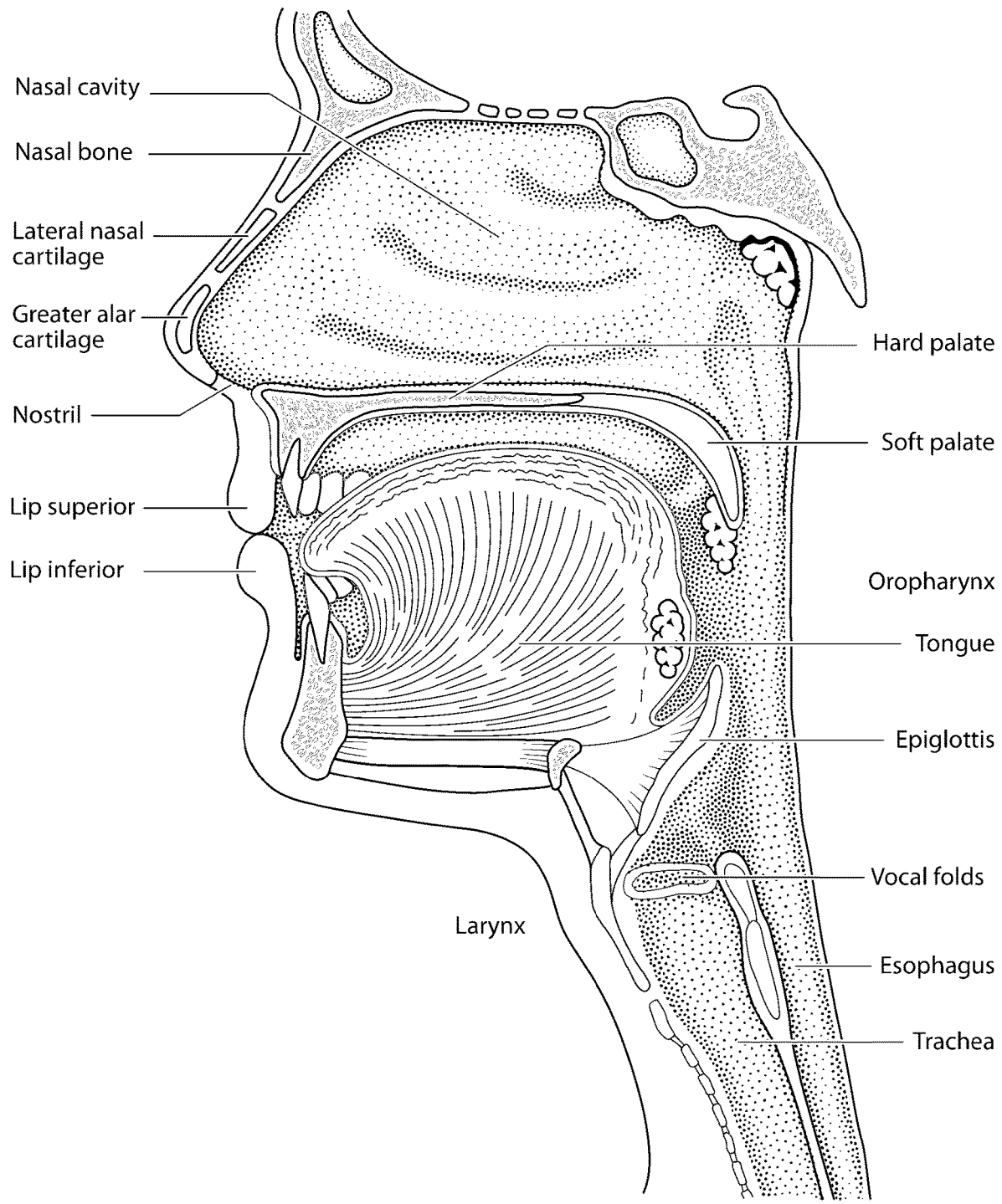

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
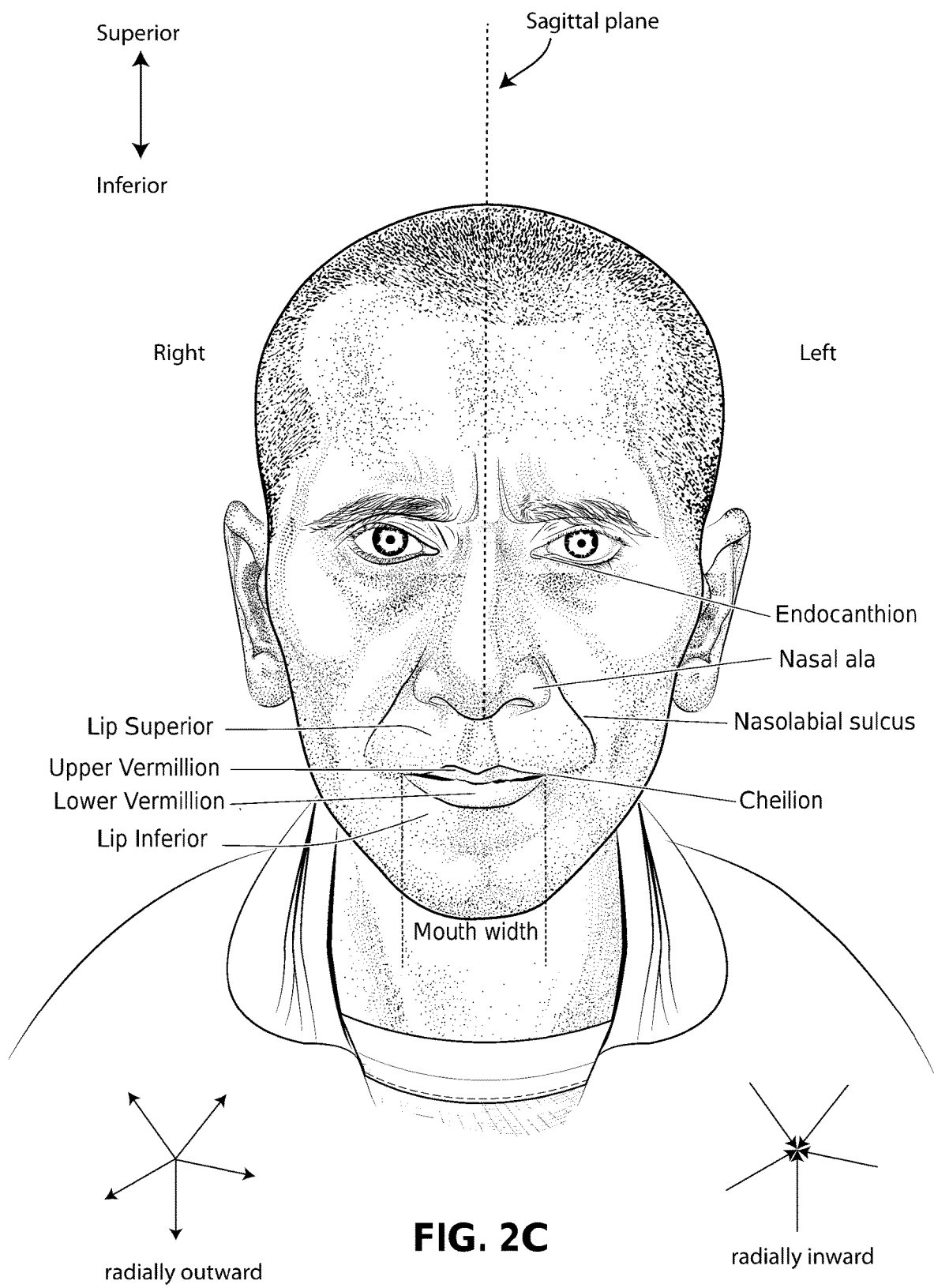

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
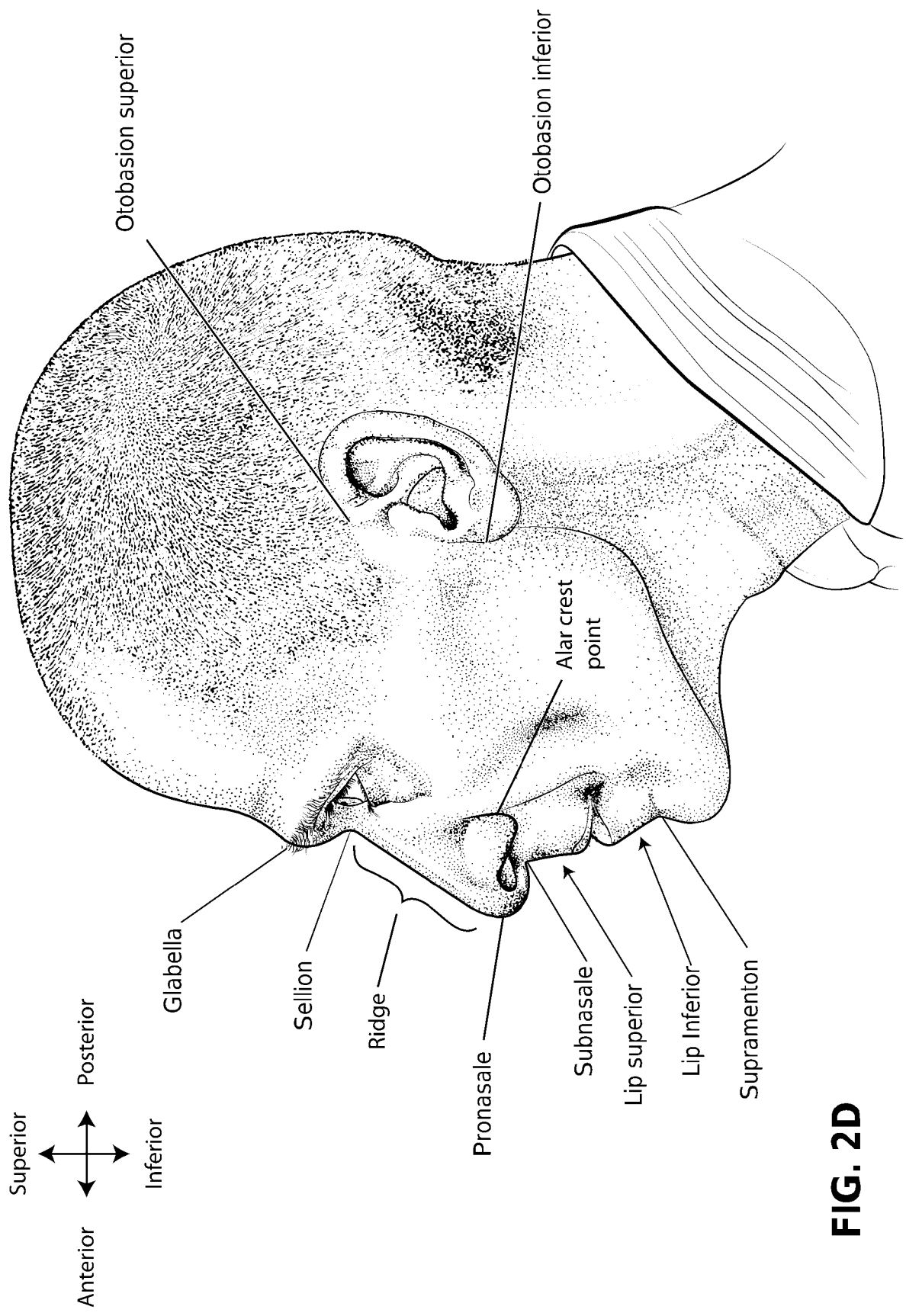

FIG. 2D is a side view of a head with several features of surface anatomy identified including *glabella*, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
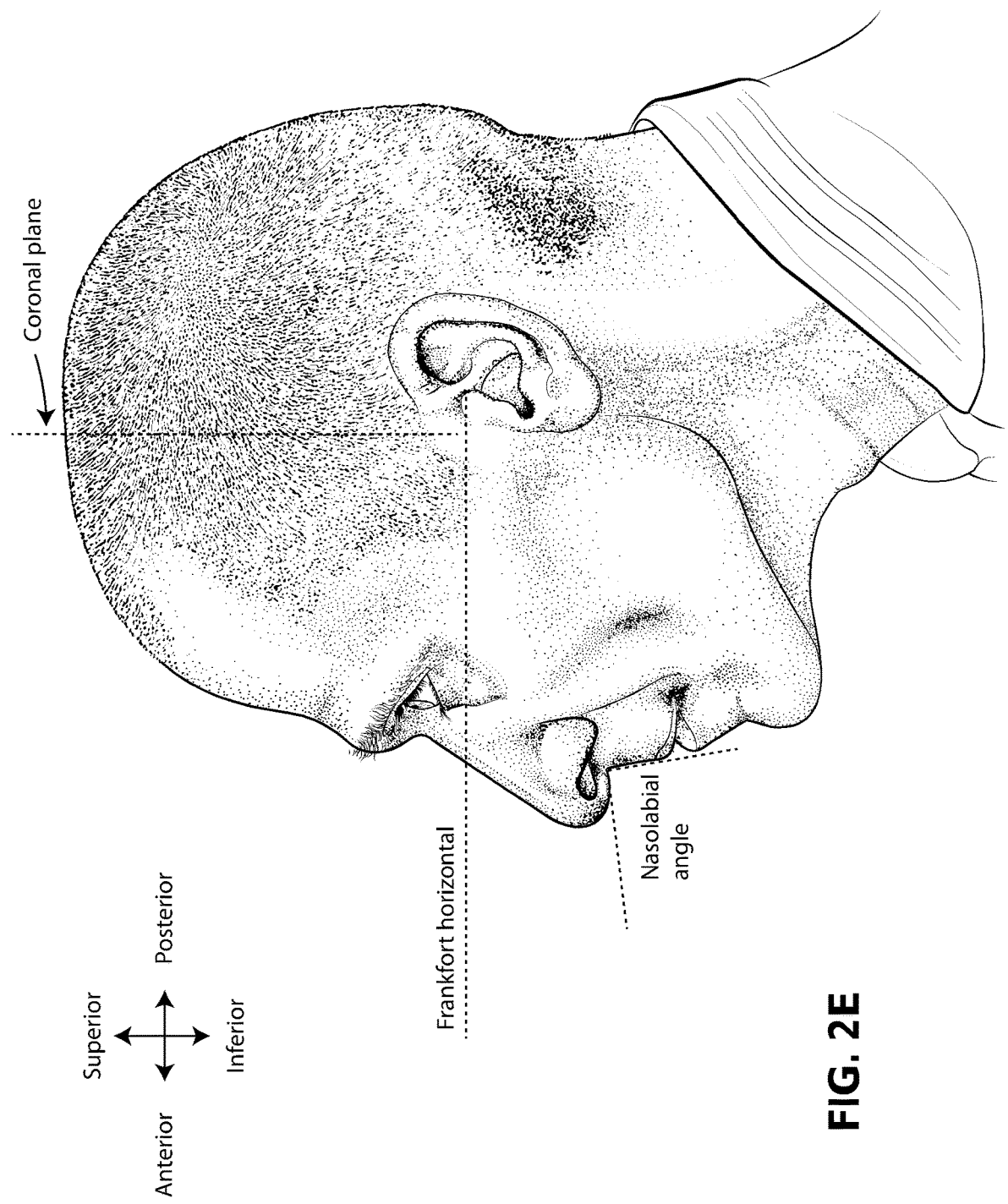

FIG. 2E is a further side view of a head. The approximate locations of the Frankfort horizontal and nasolabial angle are indicated. The coronal plane is also indicated.

Figure 2F:
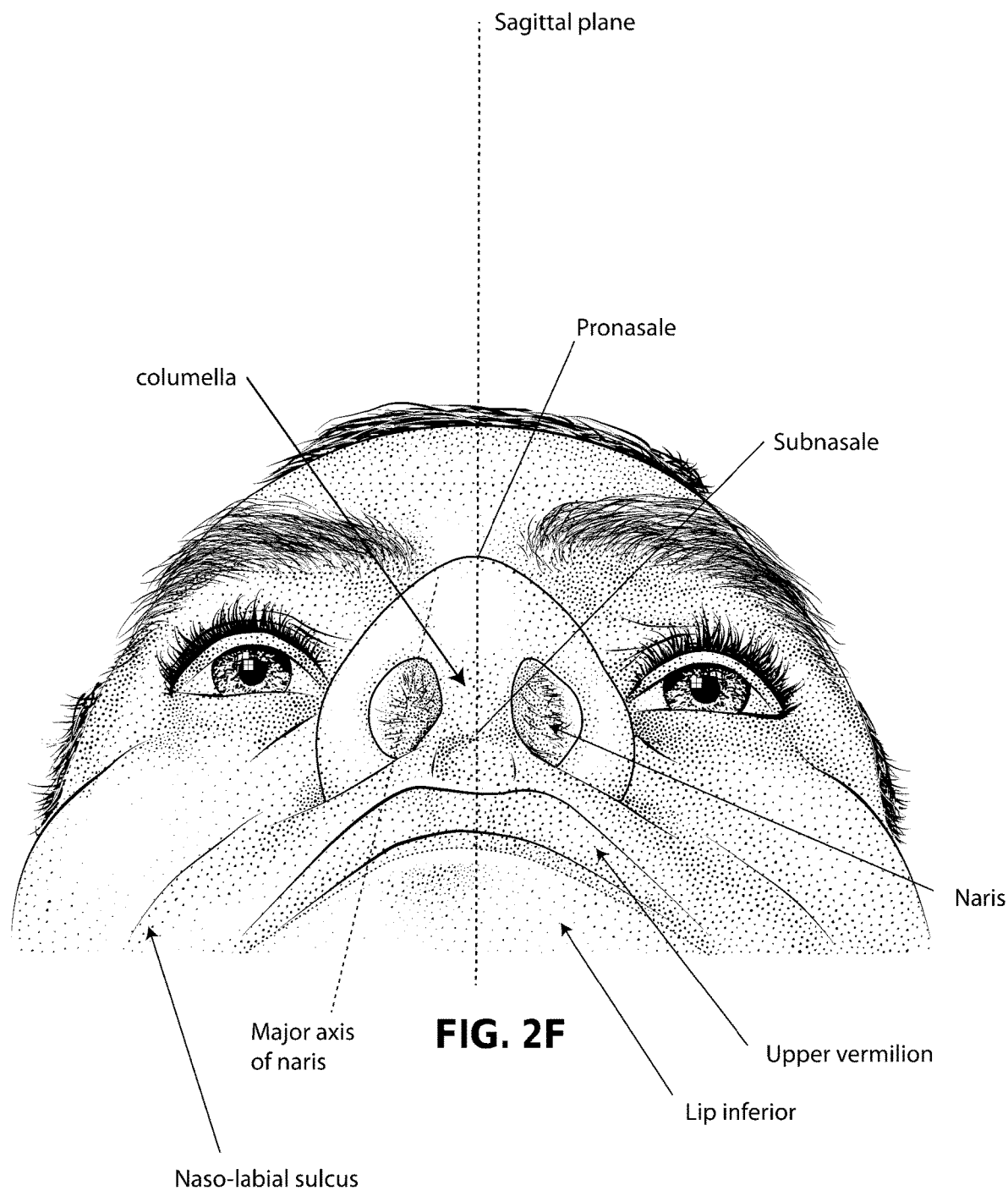

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
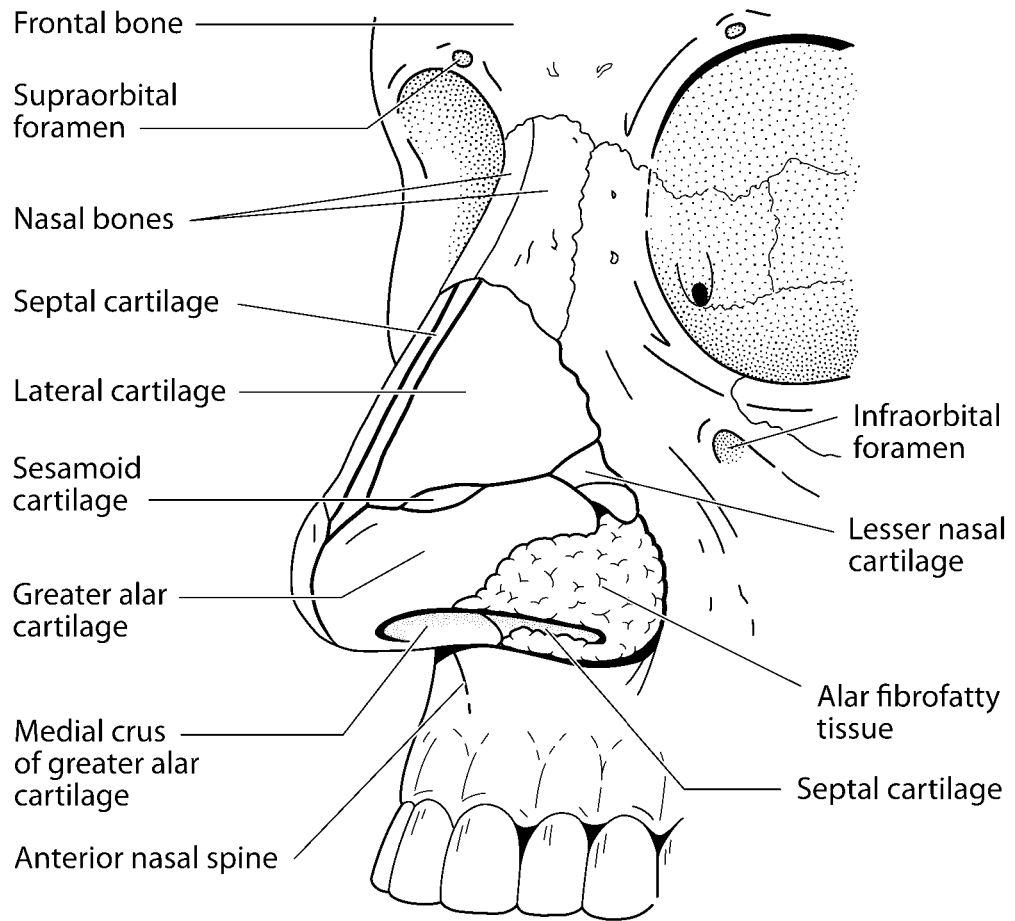

FIG. 2L shows an anterolateral view of a nose.

4.3 Patient Interface

Figure 3A:
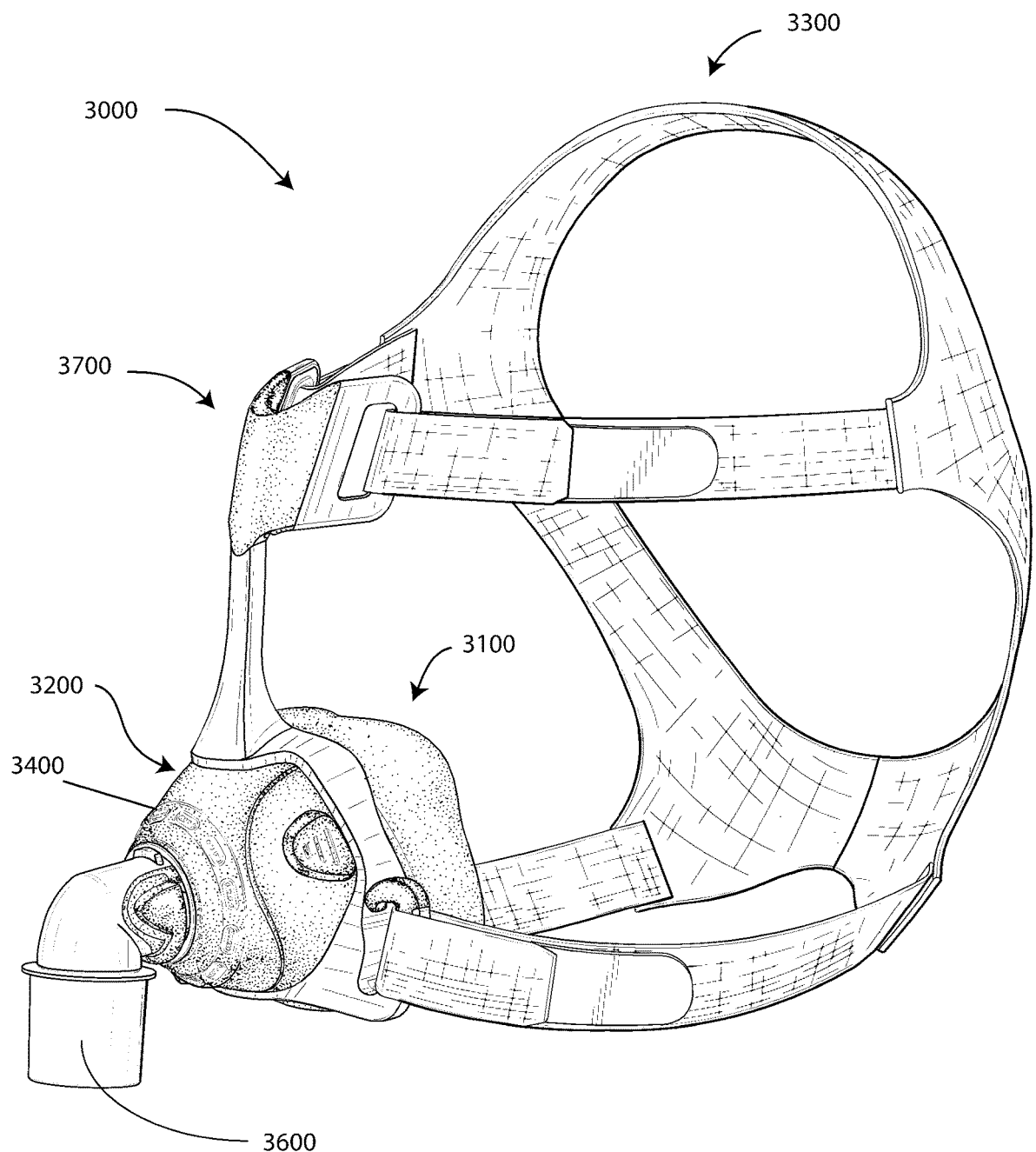

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
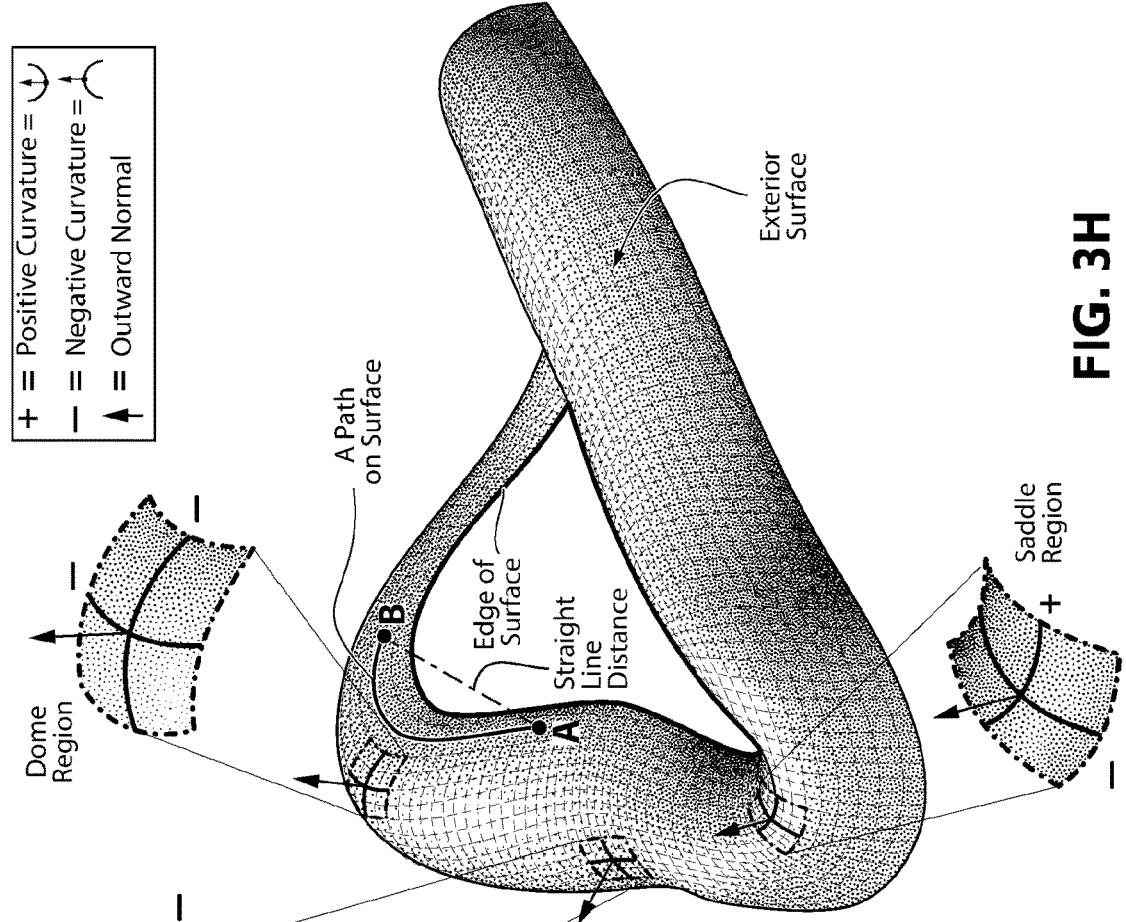
Figure 3G:
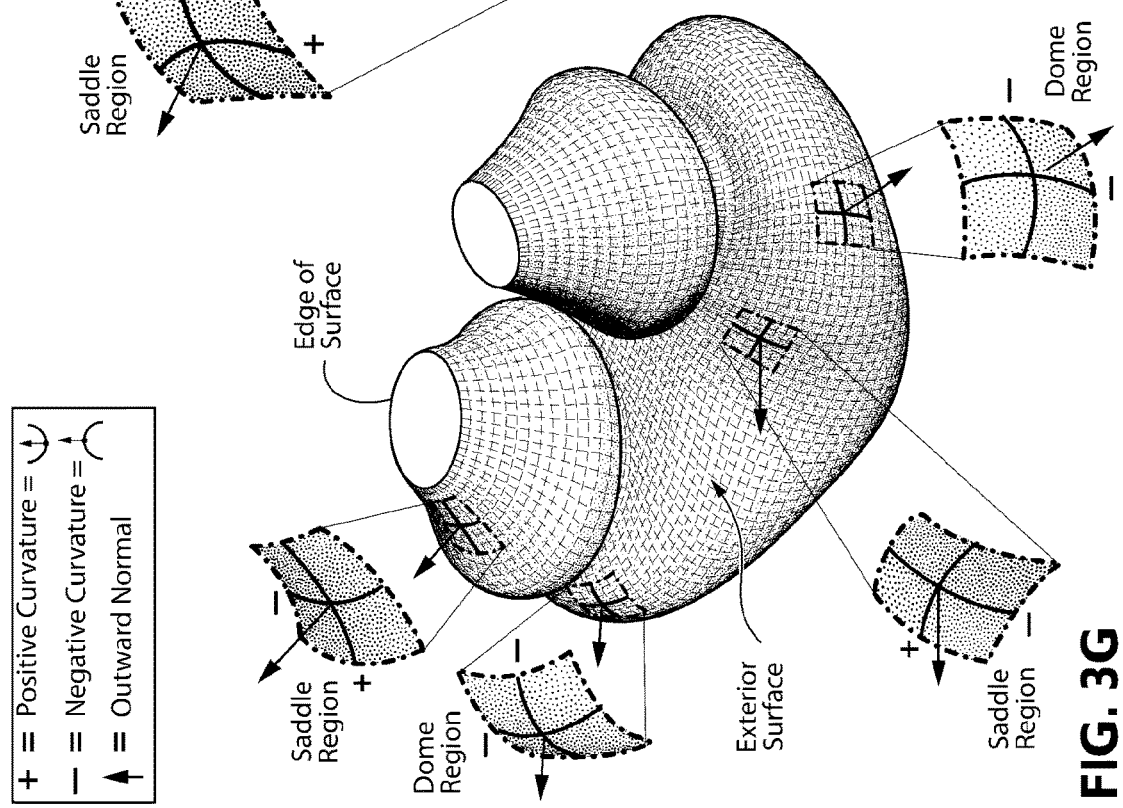

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
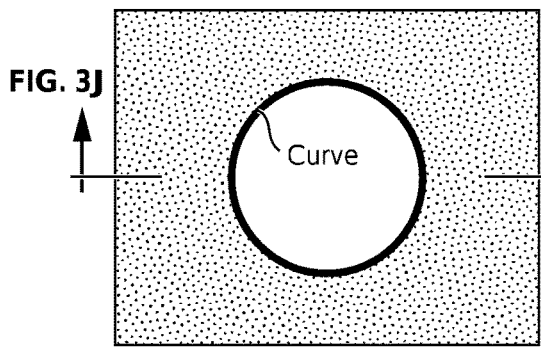

FIG. 3I shows the surface of a structure, with a one dimensional hole in the surface. The illustrated plane curve forms the boundary of a one dimensional hole.

Figure 3K:
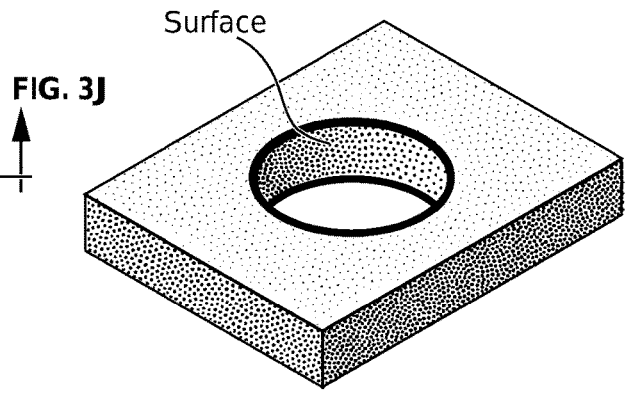
Figure 3J:
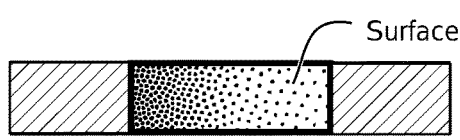

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
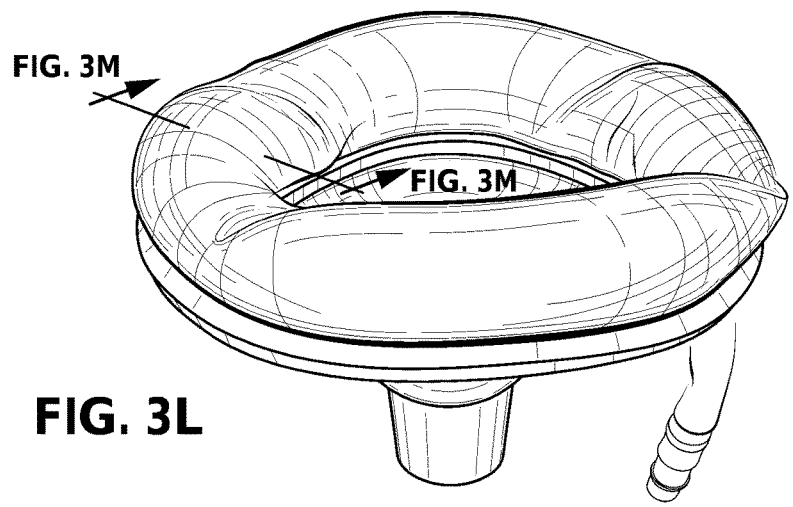

FIG. 3L shows a mask having an inflatable bladder as a cushion.

Figure 3M:
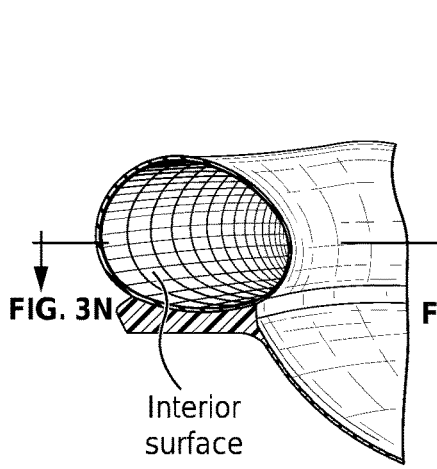

FIG. 3M shows a cross-section through the mask of FIG. 3L, and shows the interior surface of the bladder. The interior surface bounds the two dimensional hole in the mask.

Figure 3N:
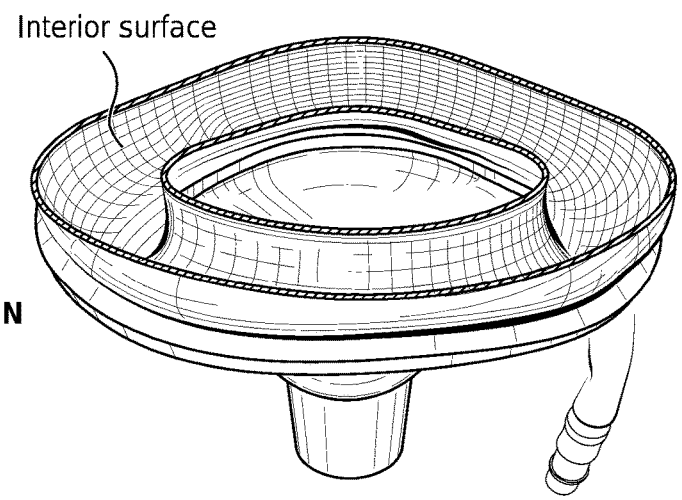

FIG. 3N shows a further cross-section through the mask of FIG. 3L. The interior surface is also indicated.

Figure 3O:
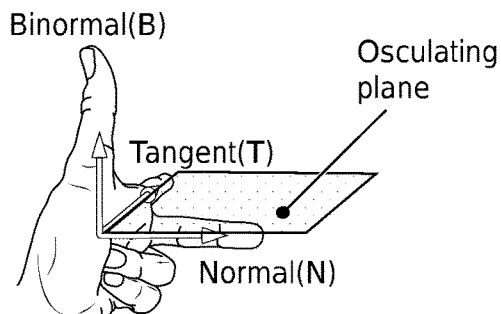

FIG. 3O illustrates a left-hand rule.

Figure 3P:
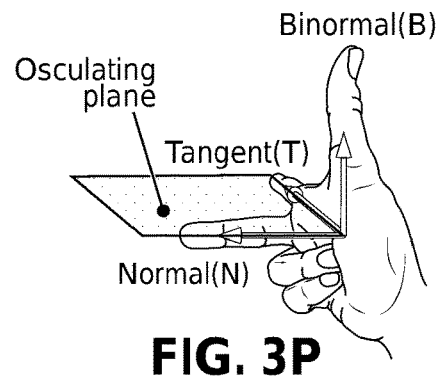

FIG. 3P illustrates a right-hand rule.

Figure 3Q:
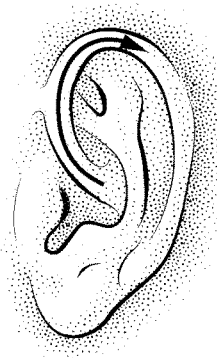

FIG. 3Q shows a left ear, including the left ear helix.

Figure 3S:
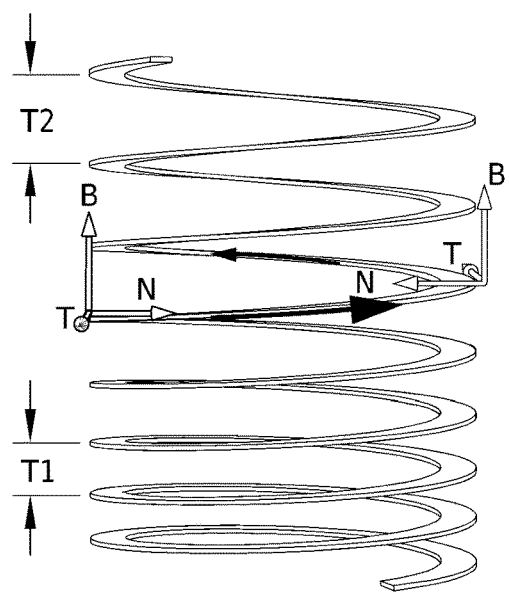
Figure 3R:
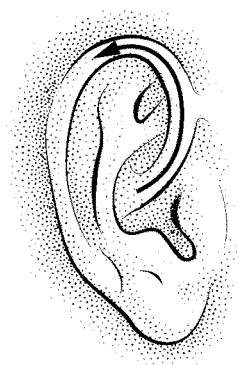

FIG. 3R shows a right ear, including the right ear helix.

FIG. 3S shows a right-hand helix.

Figure 3T:
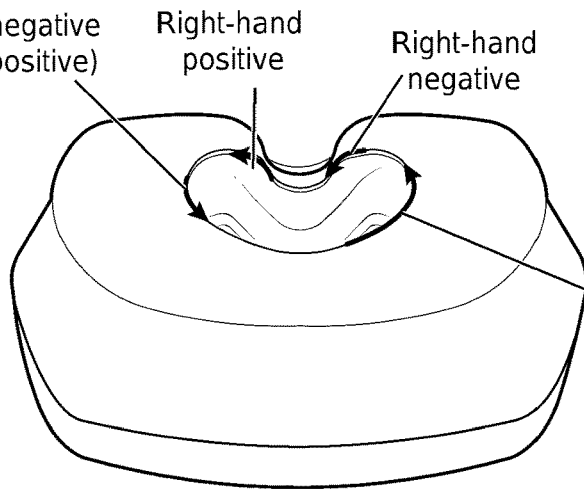

FIG. 3T shows a view of a mask, including the sign of the torsion of the space curve defined by the edge of the sealing membrane in different regions of the mask.

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 Rpt Device

Figure 4A:
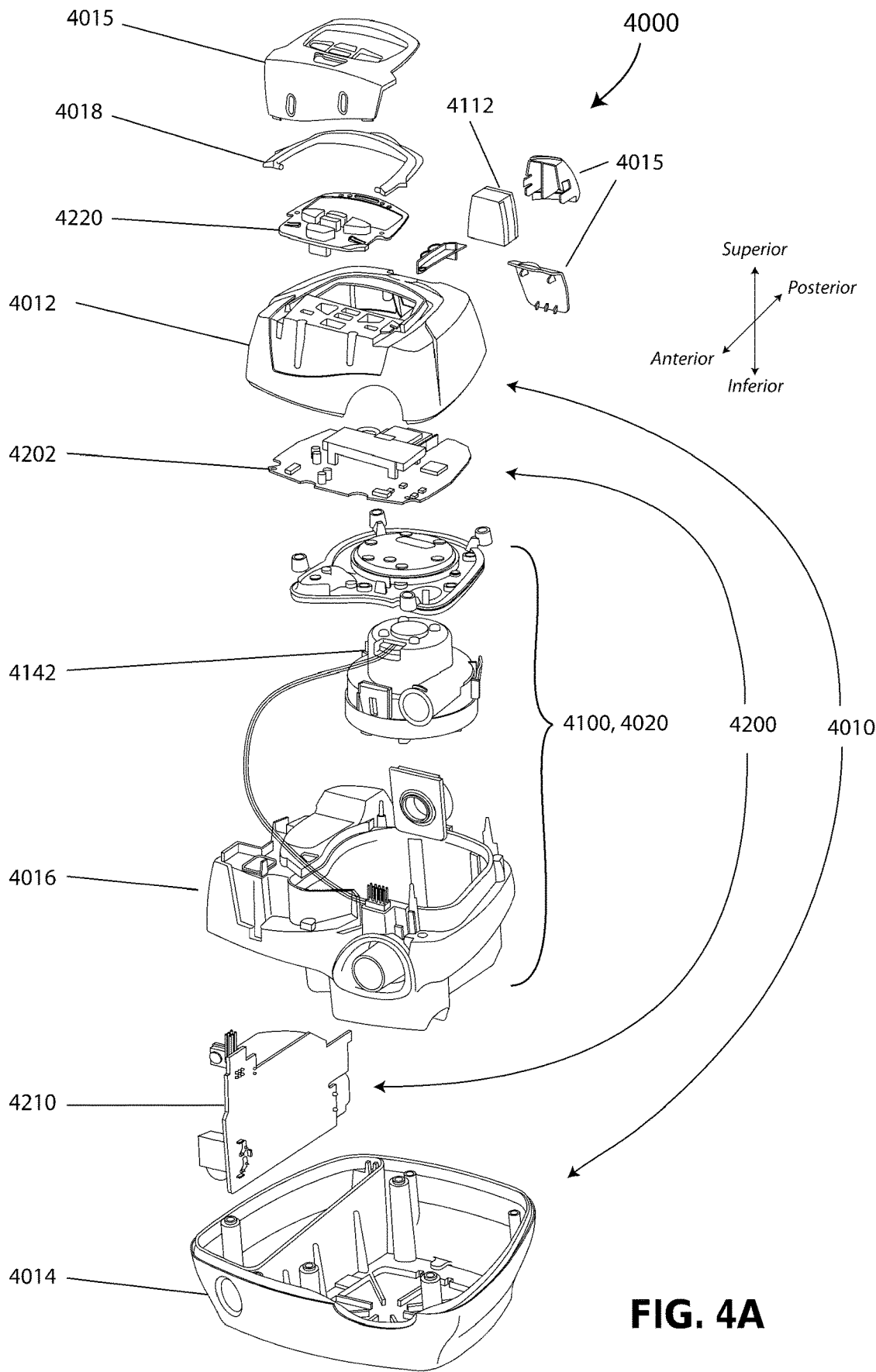

FIG. 4A shows an RPT device in accordance with one form of the present technology.

Figure 4B:
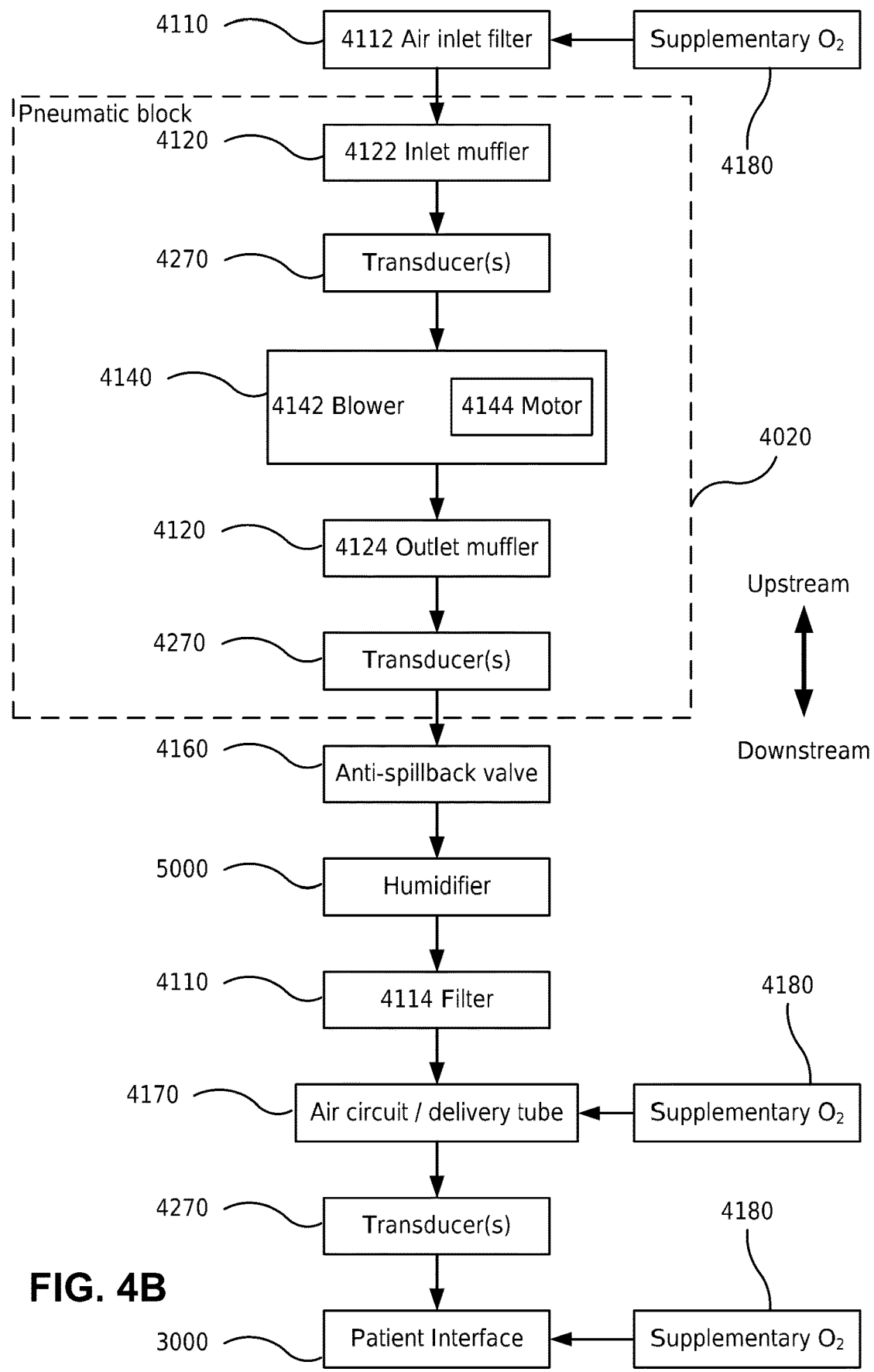

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Breathing Waveforms

Figure 5:
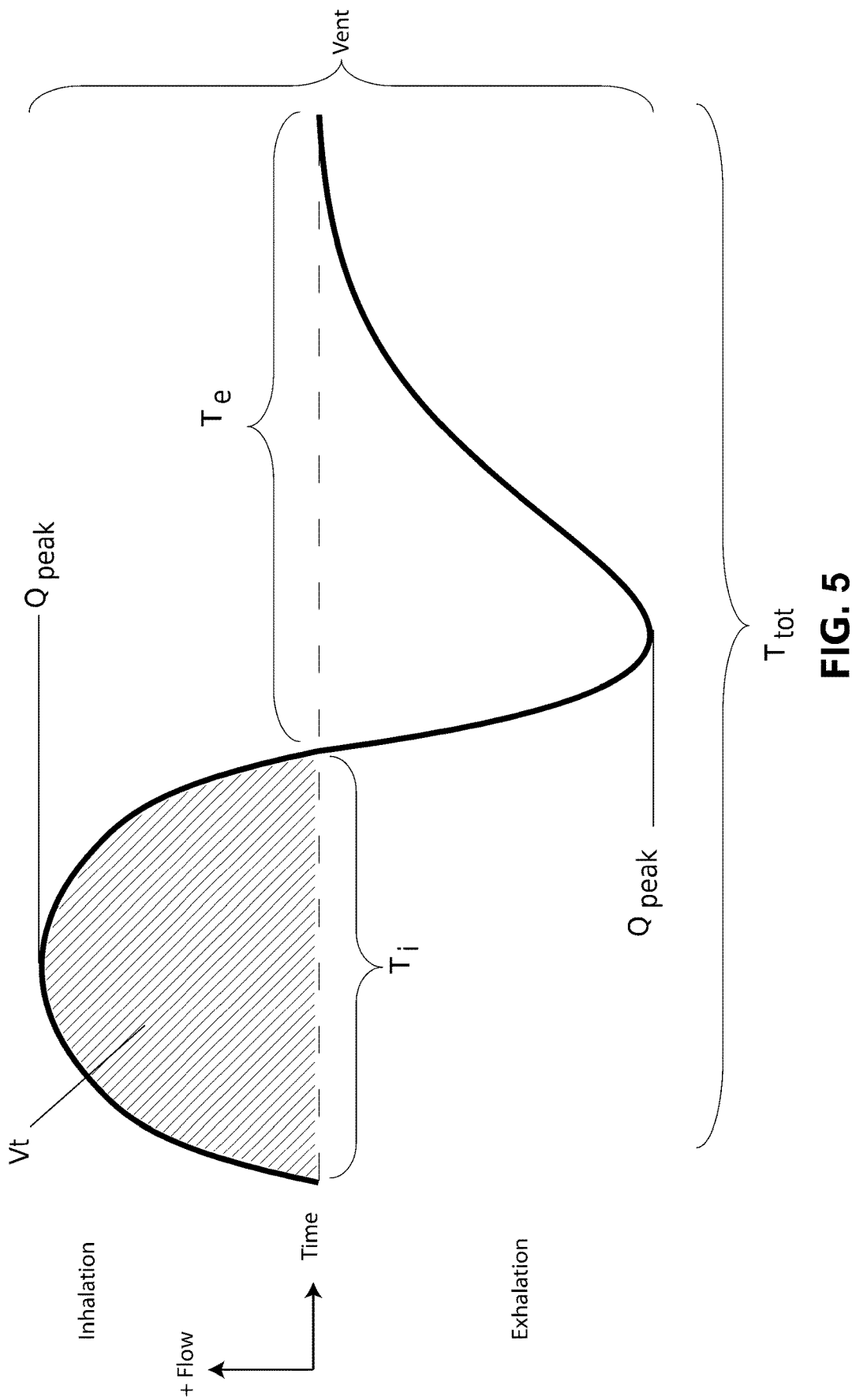

FIG. 5 shows a model typical breath waveform of a person while sleeping.

4.6 Heat and Moisture Exchanger (HME)

Figure 6A:
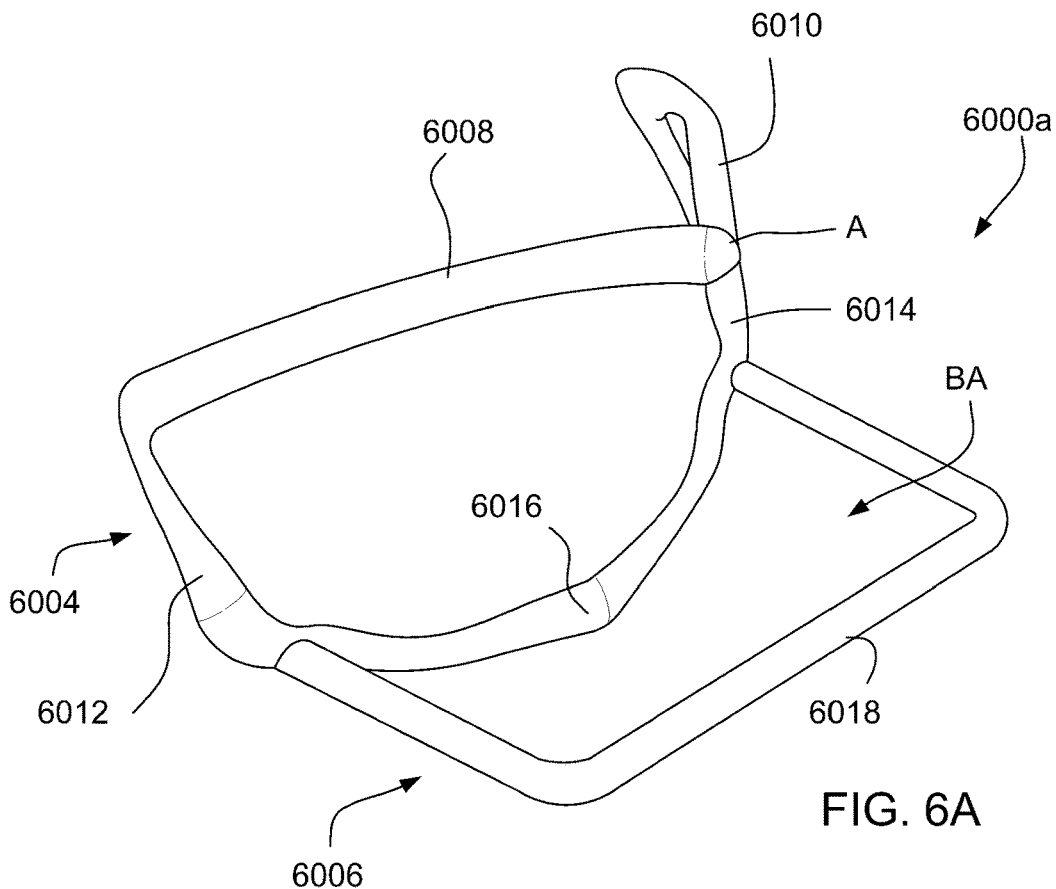

FIG. 6A is a perspective view of a first example of a frame for supporting heat and moisture exchanger (HME) material.

Figure 6B:
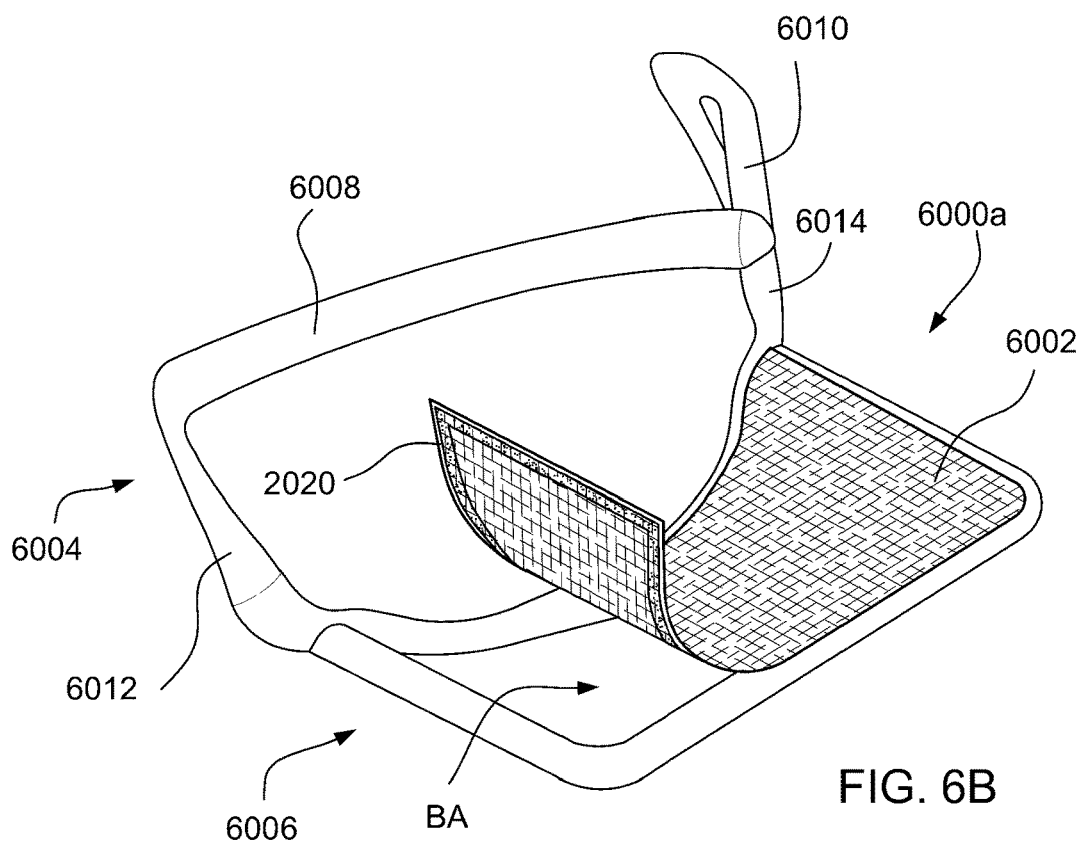
Figures 1, 6A:
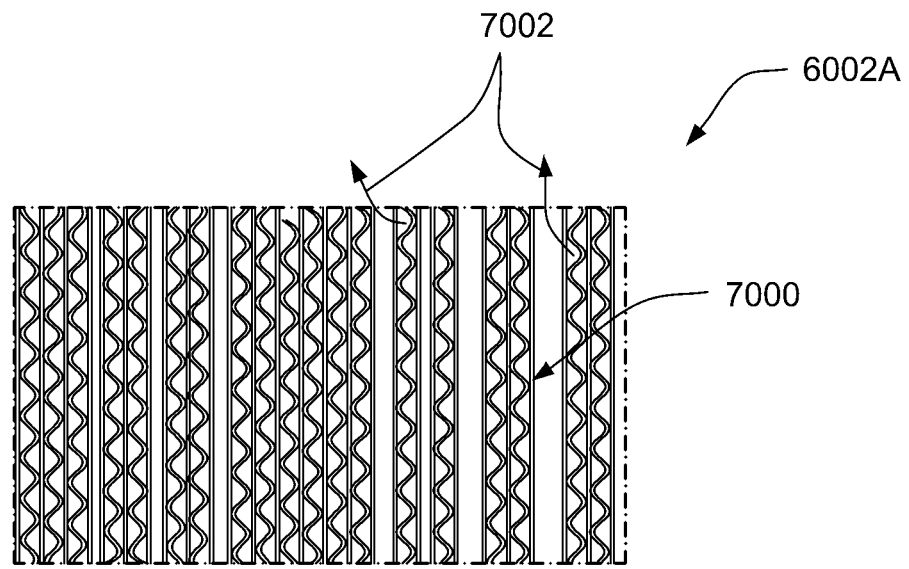

FIG. 6A-1 is an end view of corrugated paper used as an HME material.

Figures 2, 6A:
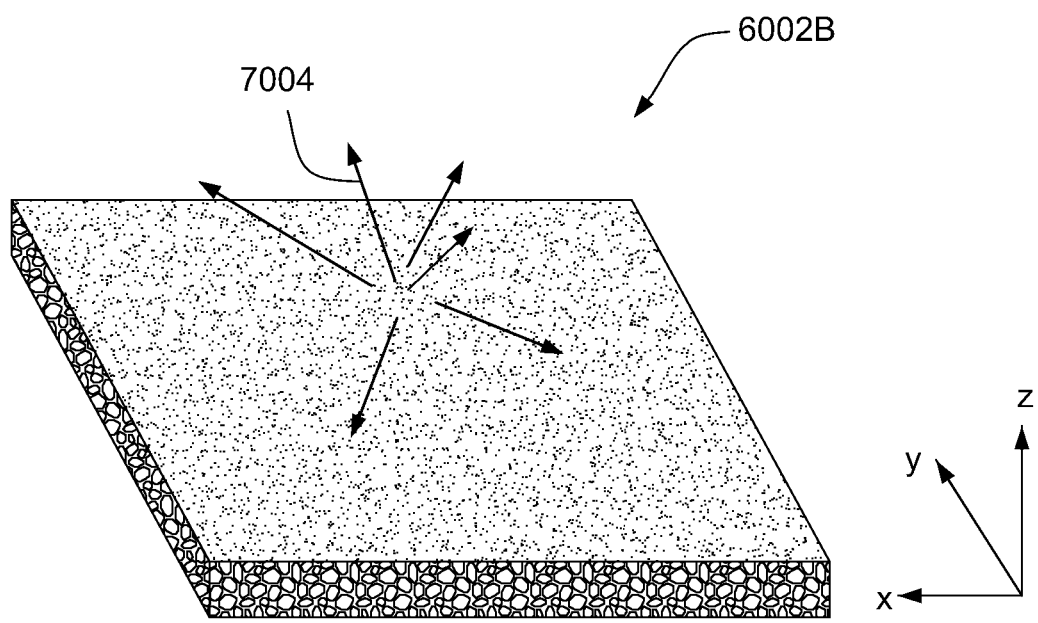

FIG. 6A-2 is a perspective view of foam used as an HME material.

FIG. 6B is a perspective view of the frame of FIG. 6A, illustrating the HME material being applied to the frame.

Figure 6C:
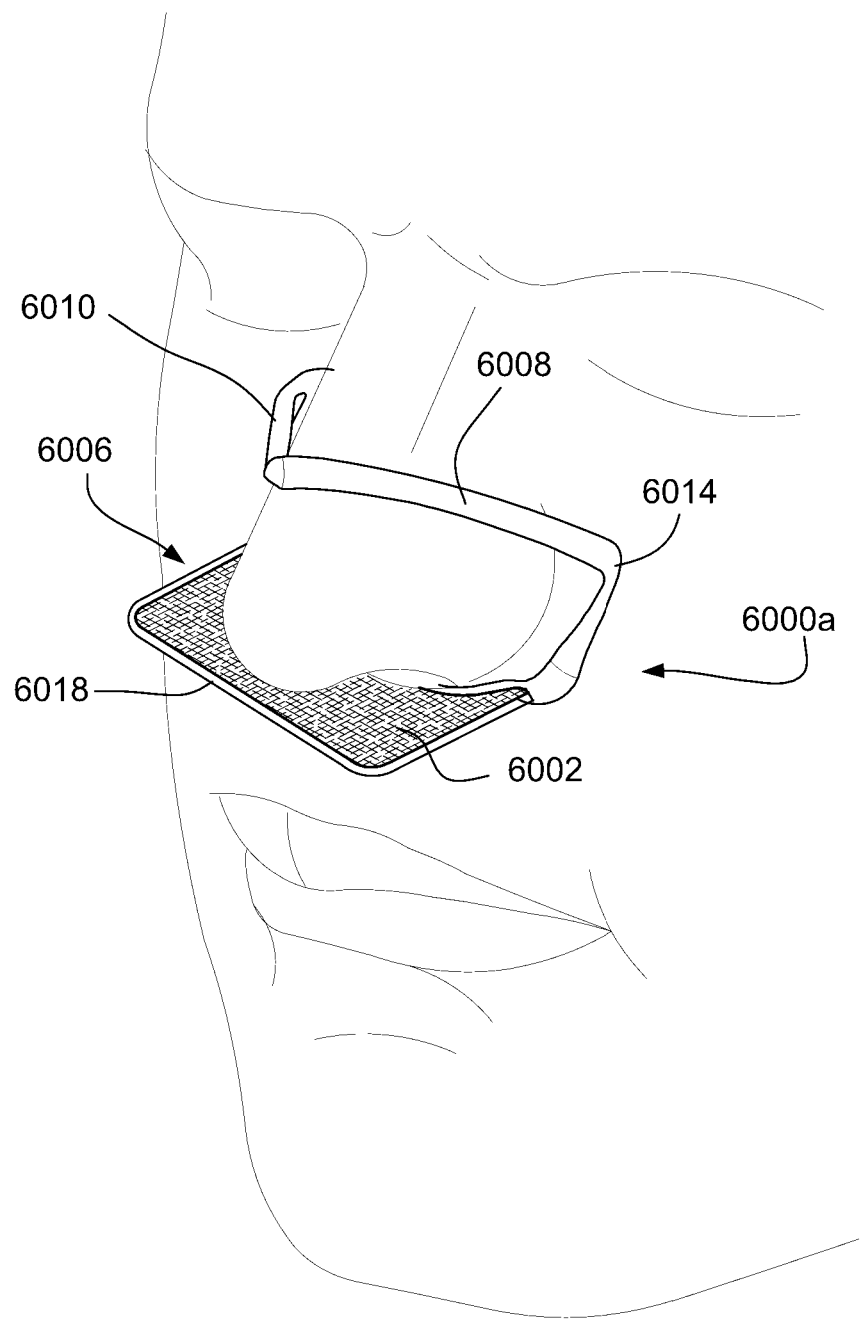

FIG. 6C is a perspective view of the frame of FIG. 6A worn by a patient.

Figure 7A:
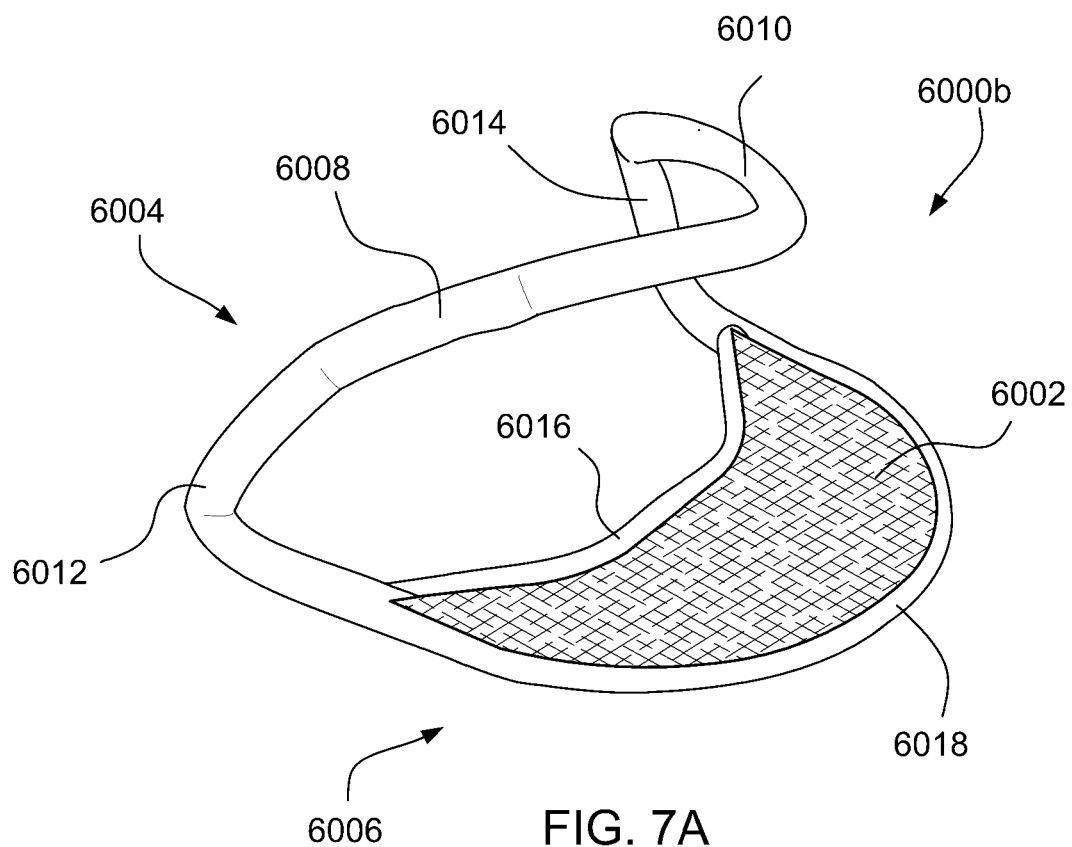

FIG. 7A is a perspective view of a second example of a frame supporting HME material.

Figure 7B:
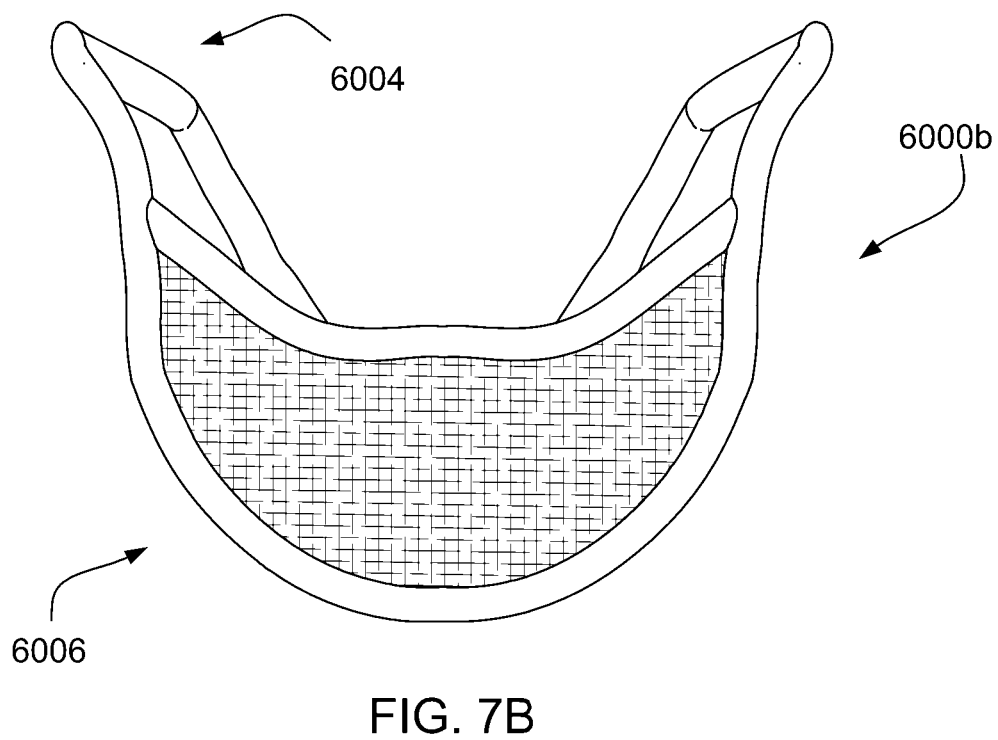

FIG. 7B is a bottom view of the frame of FIG. 7A supporting the HME material.

Figure 7C:
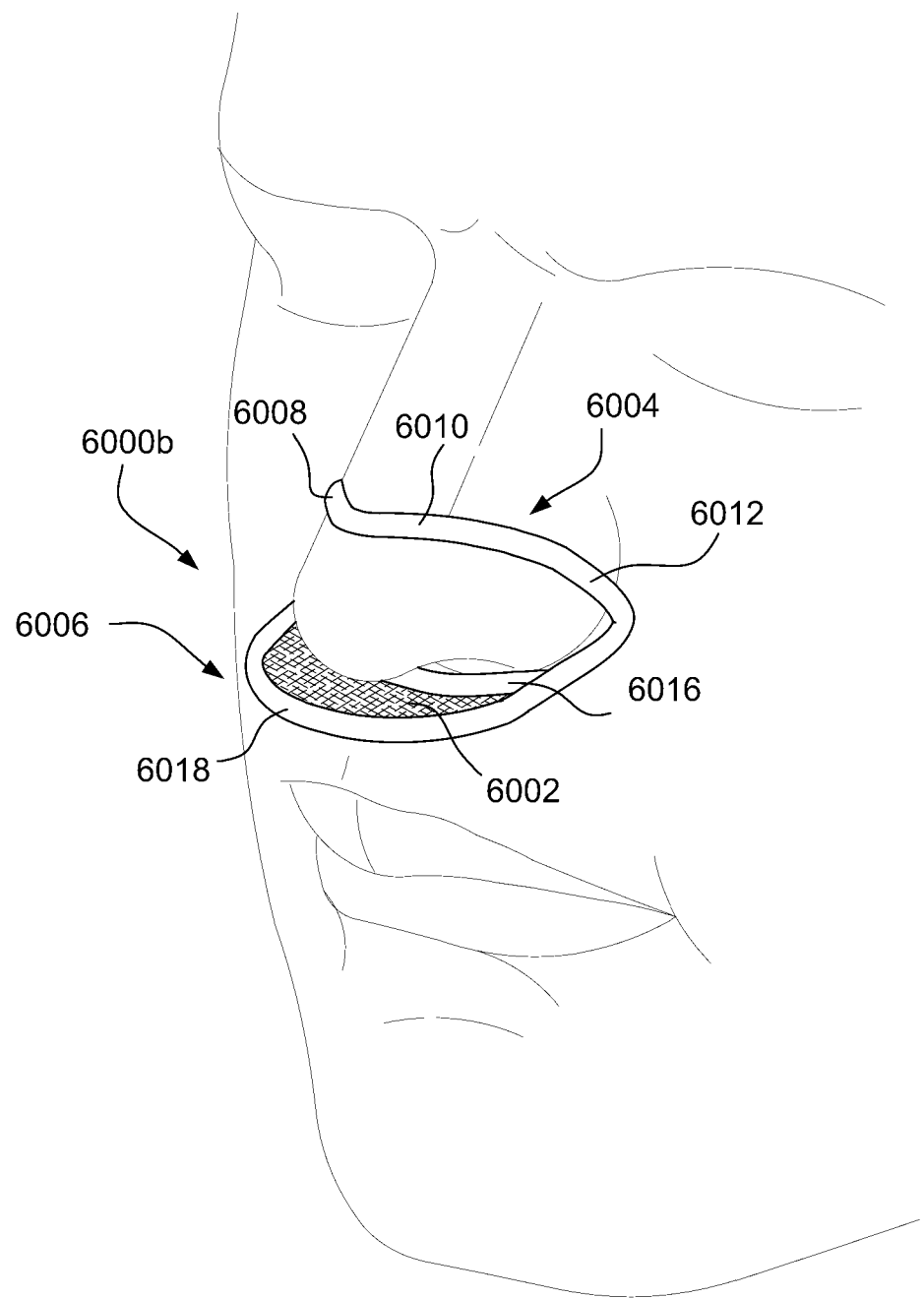

FIG. 7C is a perspective view of FIG. 7A worn by a patient.

Figure 8A:
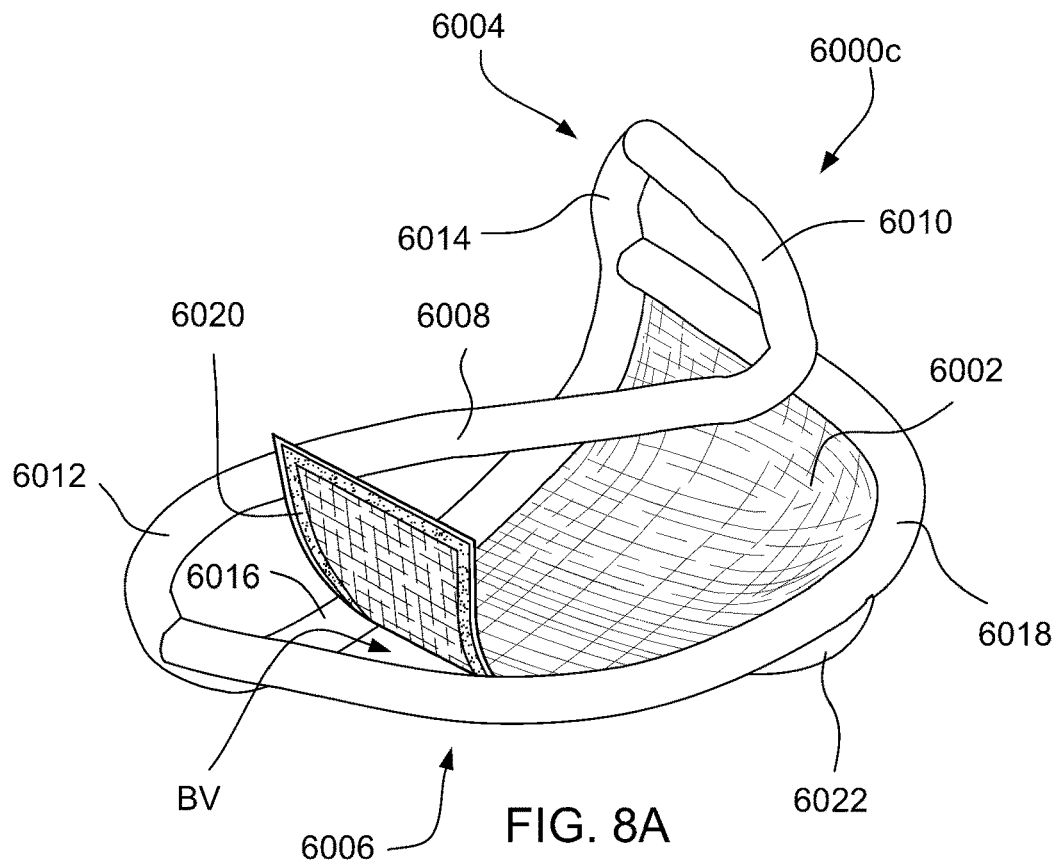

FIG. 8A is a perspective view of a third example of a frame, illustrating a single sheet of HME material being applied to the frame.

Figure 8B:
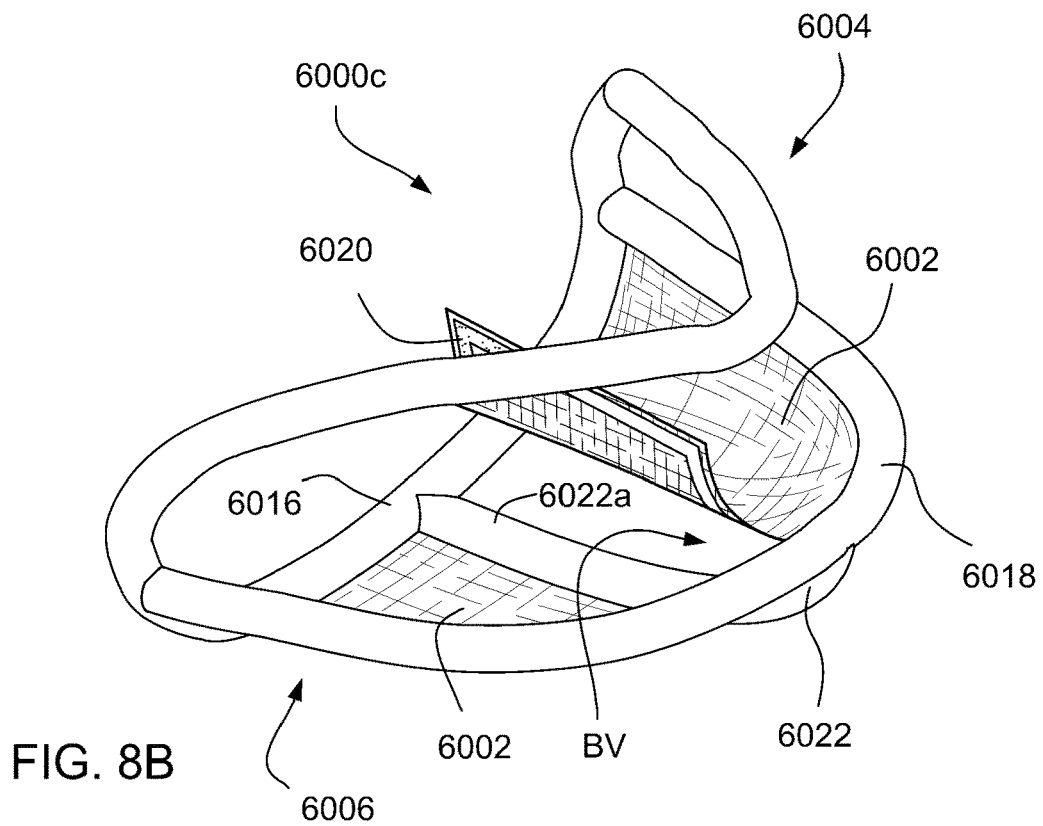

FIG. 8B is a perspective view of the frame of FIG. 8A, illustrating a pair of sheets of HME material being applied to the frame.

Figure 8C:
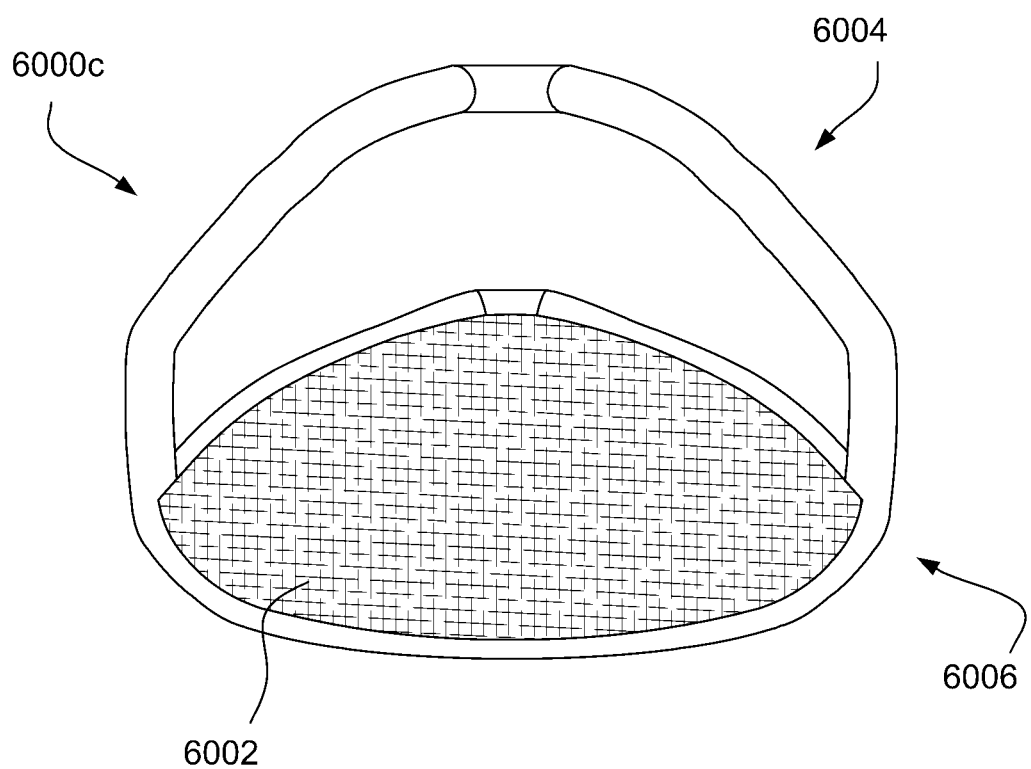

FIG. 8C is a rear view of the frame of FIG. 8A, illustrating the frame supporting the HME material.

Figure 8D:
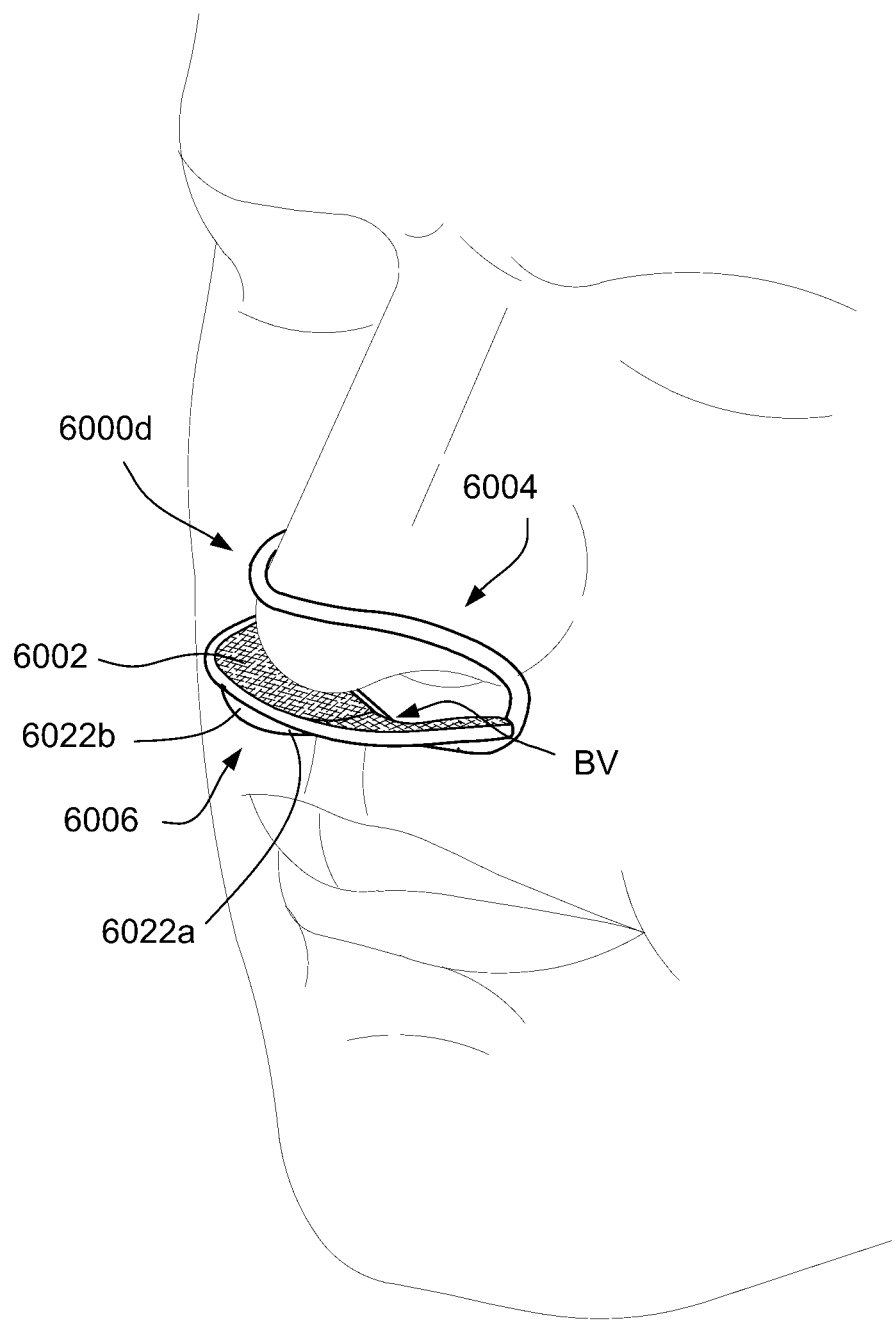

FIG. 8D is a perspective view of the frame of FIG. 8A worn by a patient.

Figure 9A:
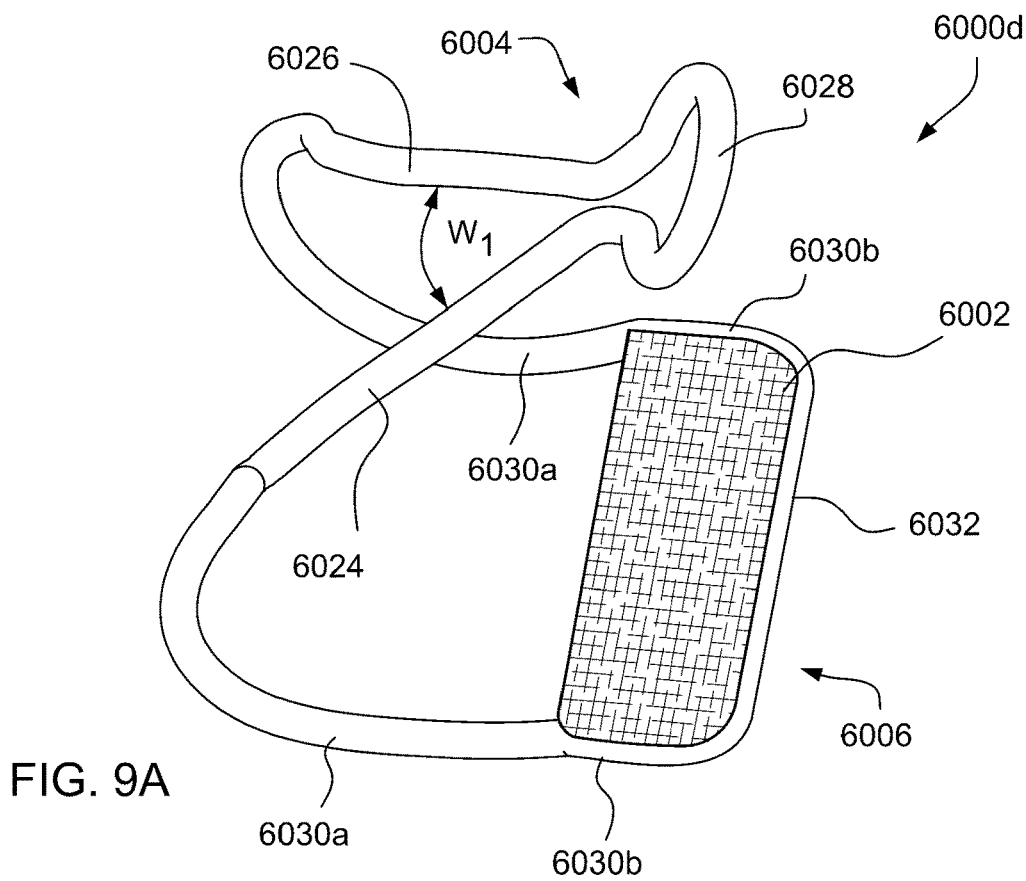

FIG. 9A is a perspective view of a fourth example of a frame supporting HME material, illustrating arms of the frame at a first width.

Figure 9B:
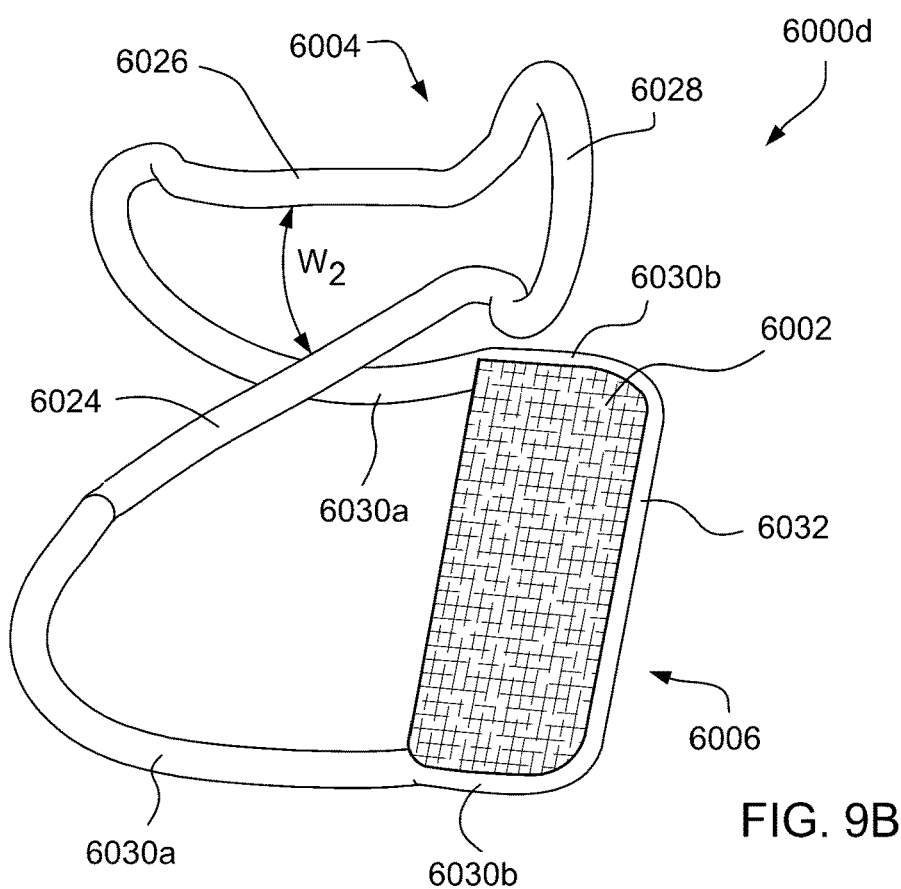

FIG. 9B is a perspective view of the frame of FIG. 9A, illustrating the arms of the frame at a second width greater than the first width.

Figure 9C:
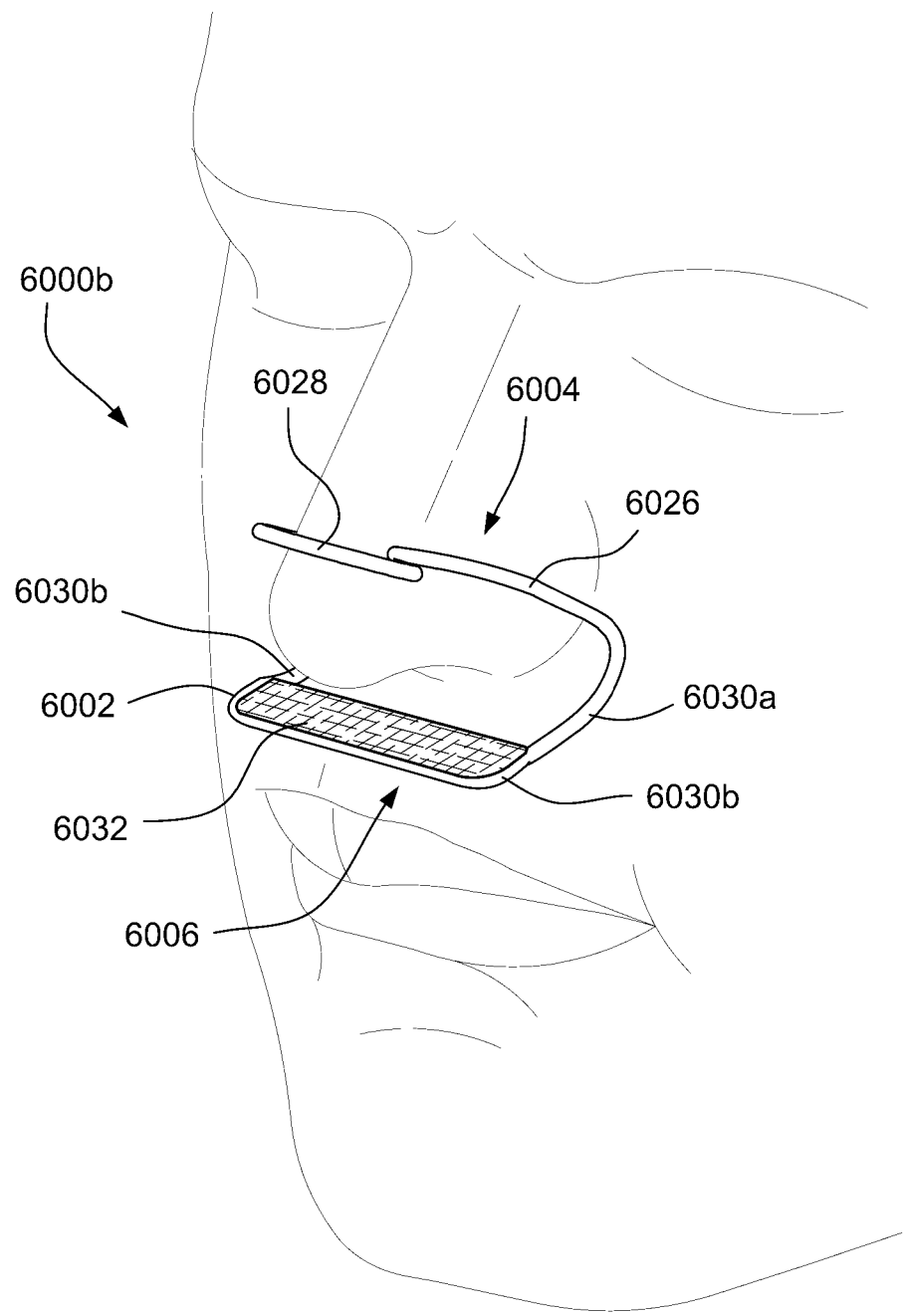

FIG. 9C is a perspective view of the frame of FIG. 9A worn by a patient.

Figure 10A:
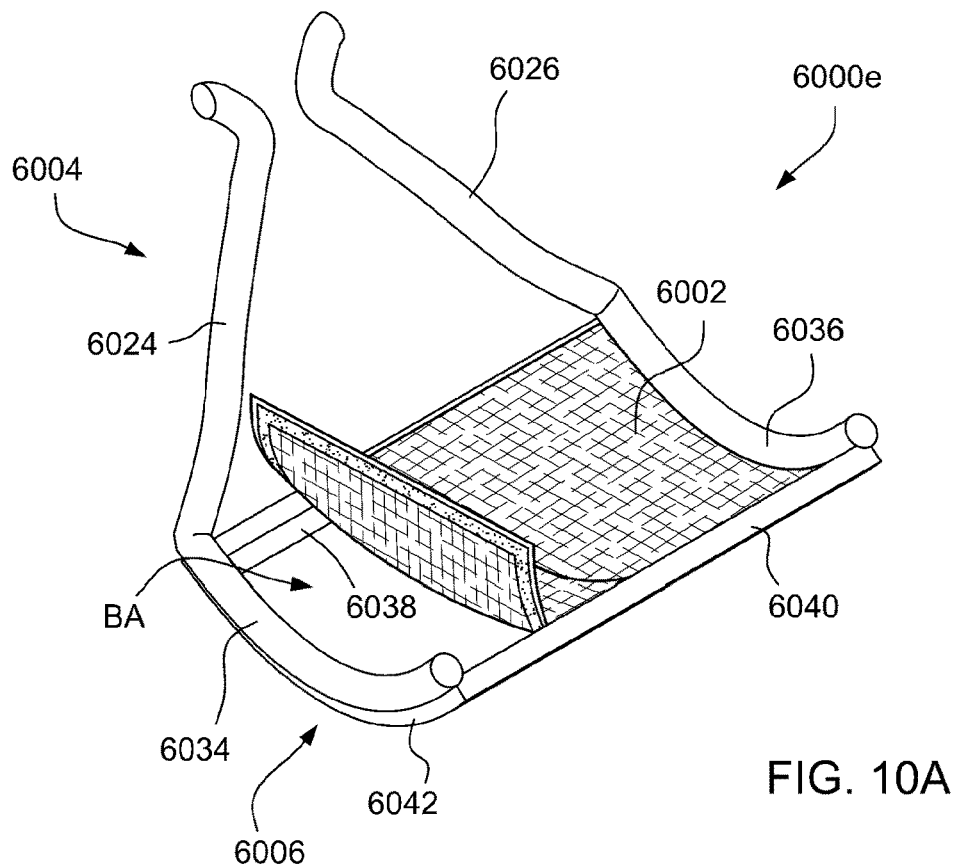

FIG. 10A is a perspective view of a fifth example of a frame, illustrating a single sheet of HME material being applied to the frame having frame arms in a first position.

Figure 10B:
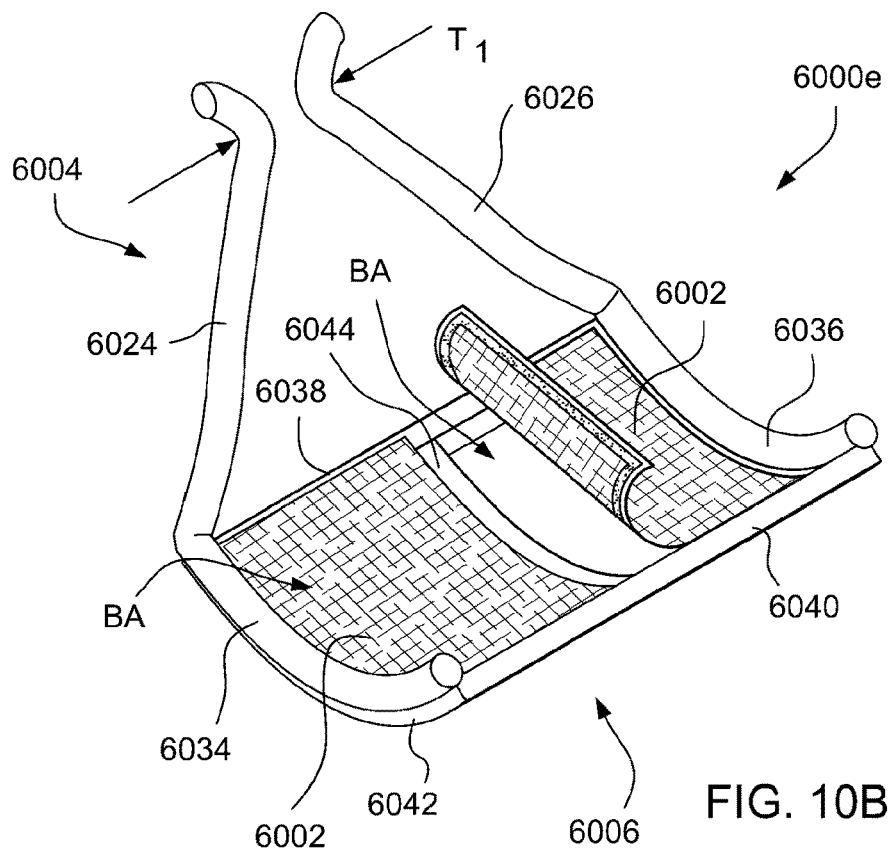

FIG. 10B is a perspective view of the frame of FIG. 10A, illustrating a pair of sheets of HME material being applied to the frame.

Figure 10C:
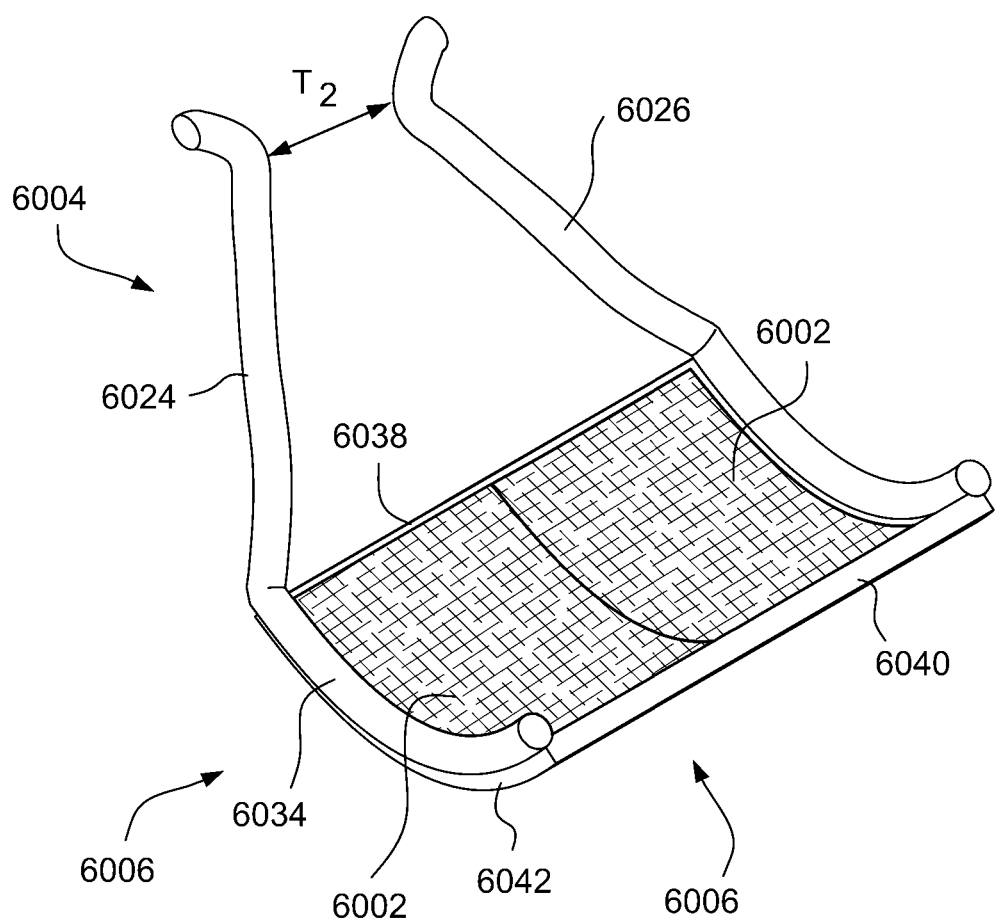

FIG. 10C is a perspective view of the frame of FIG. 10A, illustrating the frame arms in a second position where the frames are spaced further apart than in the first position.

Figure 10D:
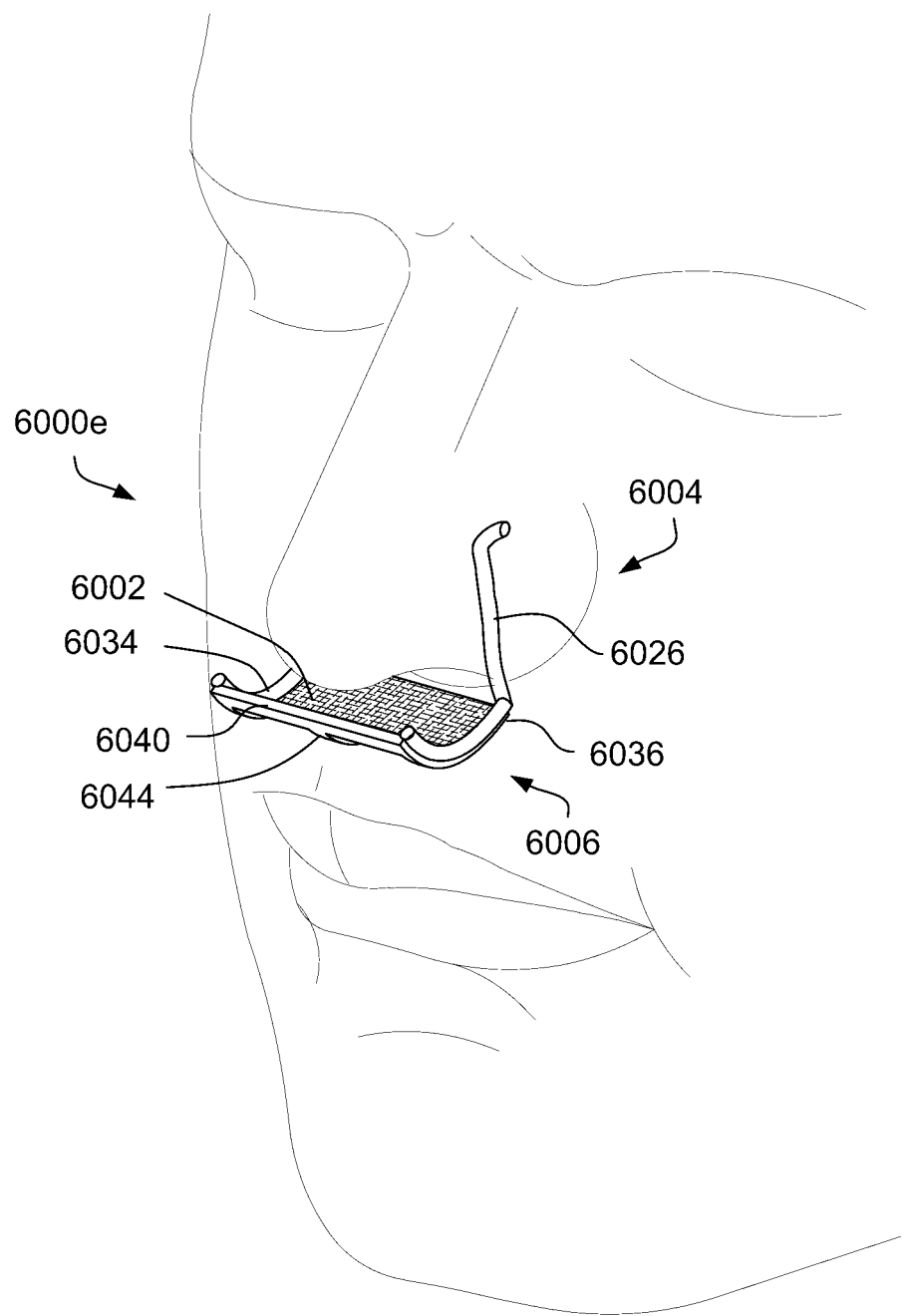

FIG. 10D is a perspective view of the frame of FIG. 10A being worn by a patient.

Figure 10E:
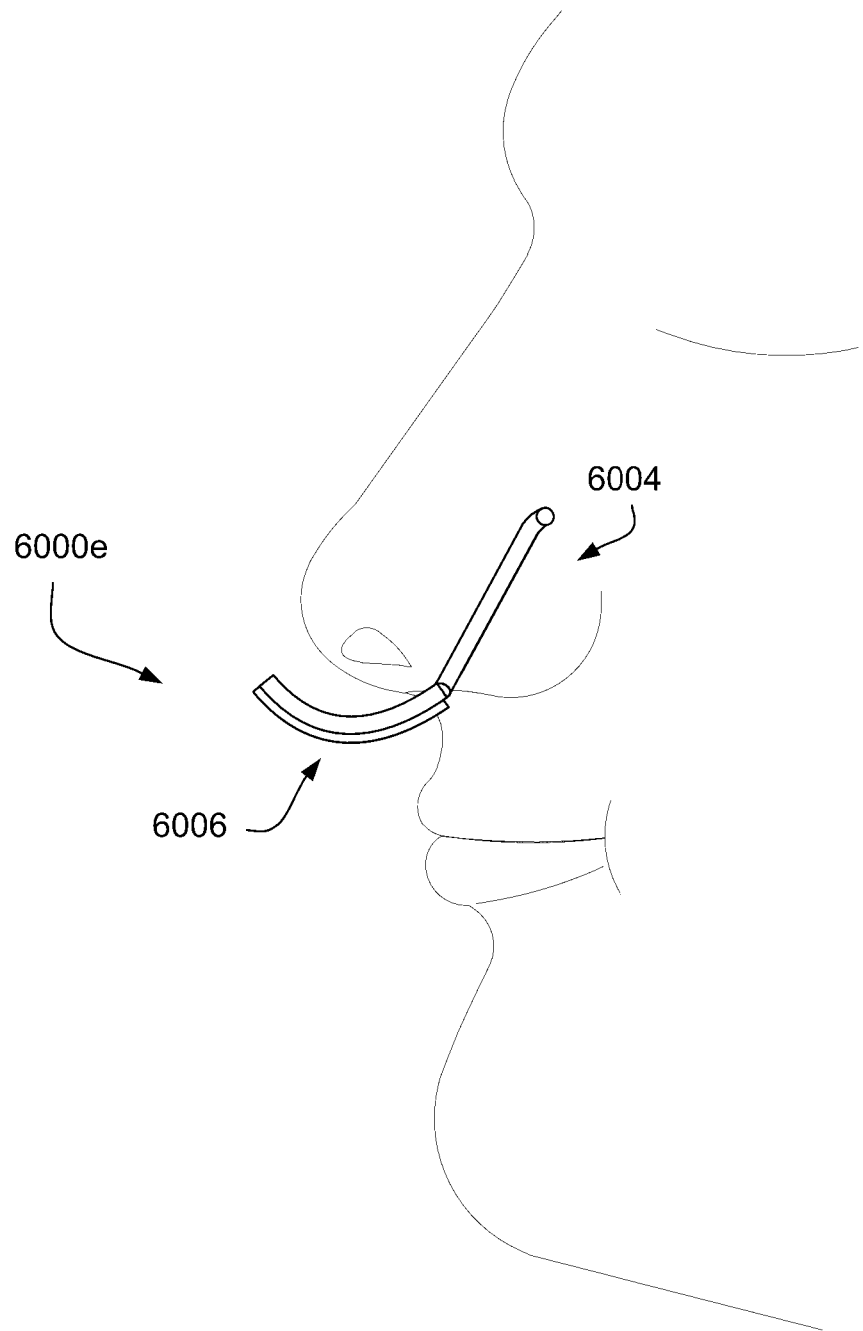

FIG. 10E is a side view of the patient of FIG. 10D wearing the frame.

Figure 11A:
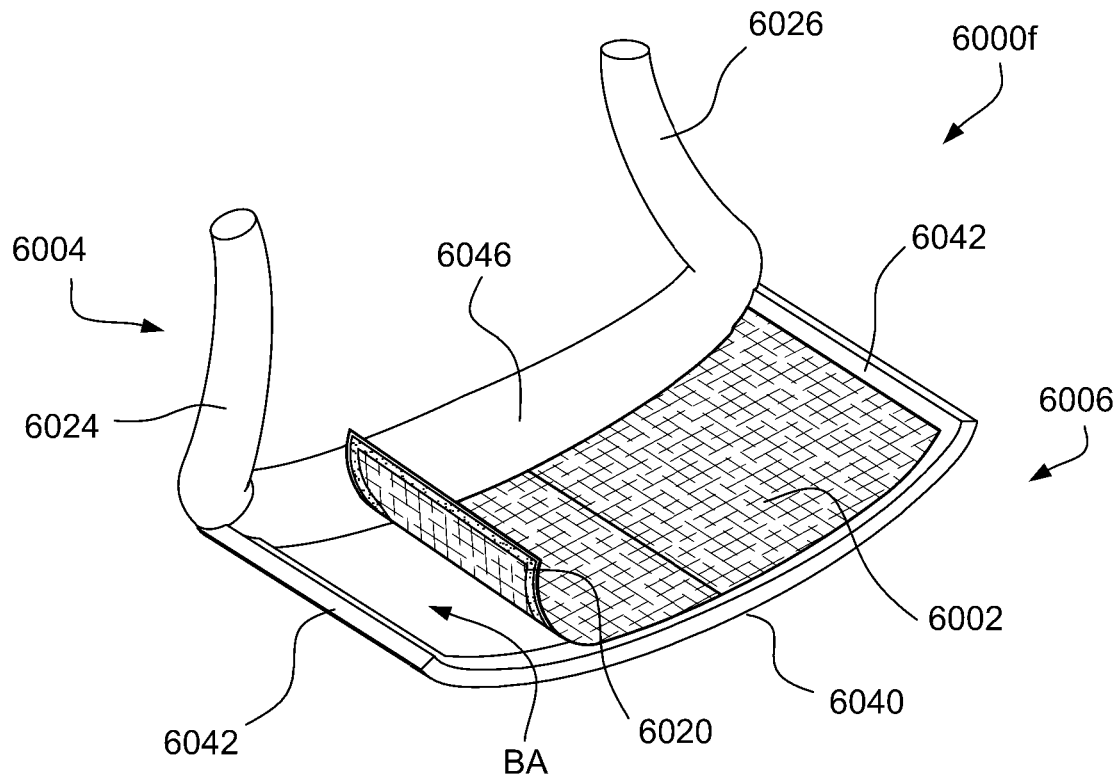

FIG. 11A is a perspective view of a sixth example of a frame, illustrating a single sheet of HME material being applied to the frame having frame arms in a first position.

Figure 11B:
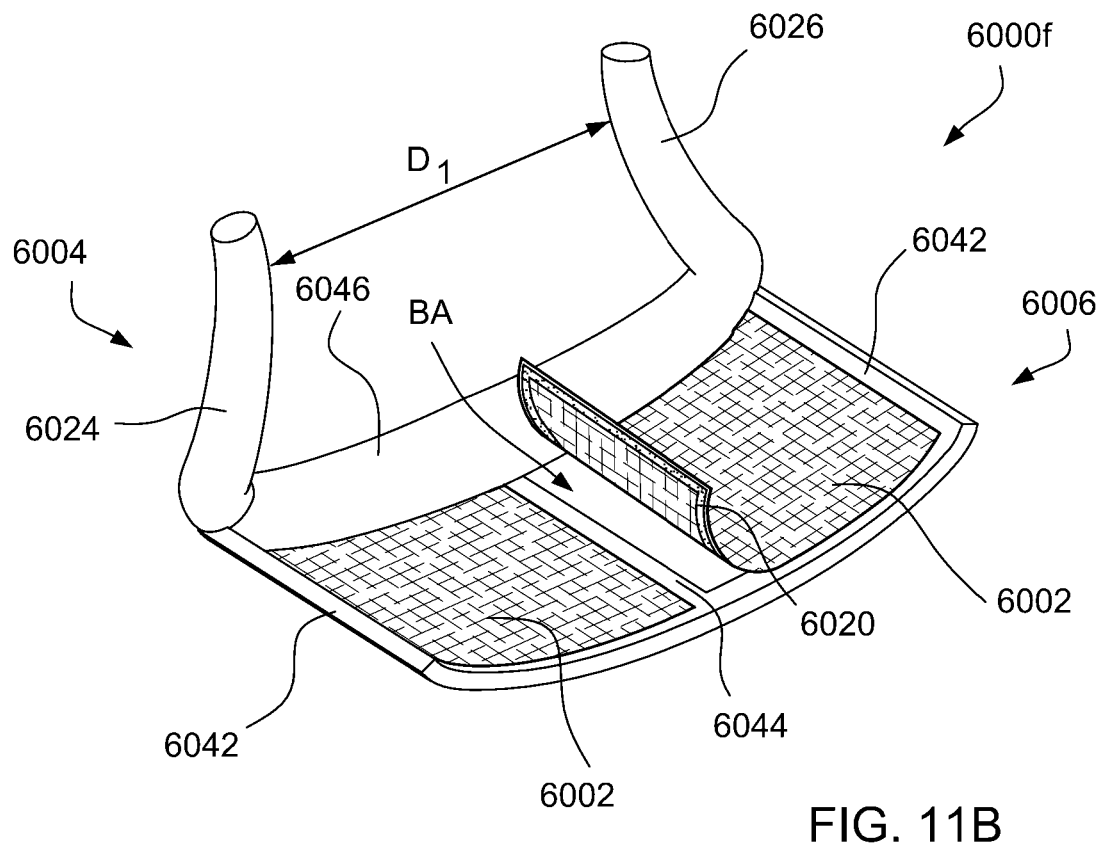

FIG. 11B is a perspective view of the frame of FIG. 11A, illustrating a pair of sheets of HME material being applied to the frame.

Figure 11C:
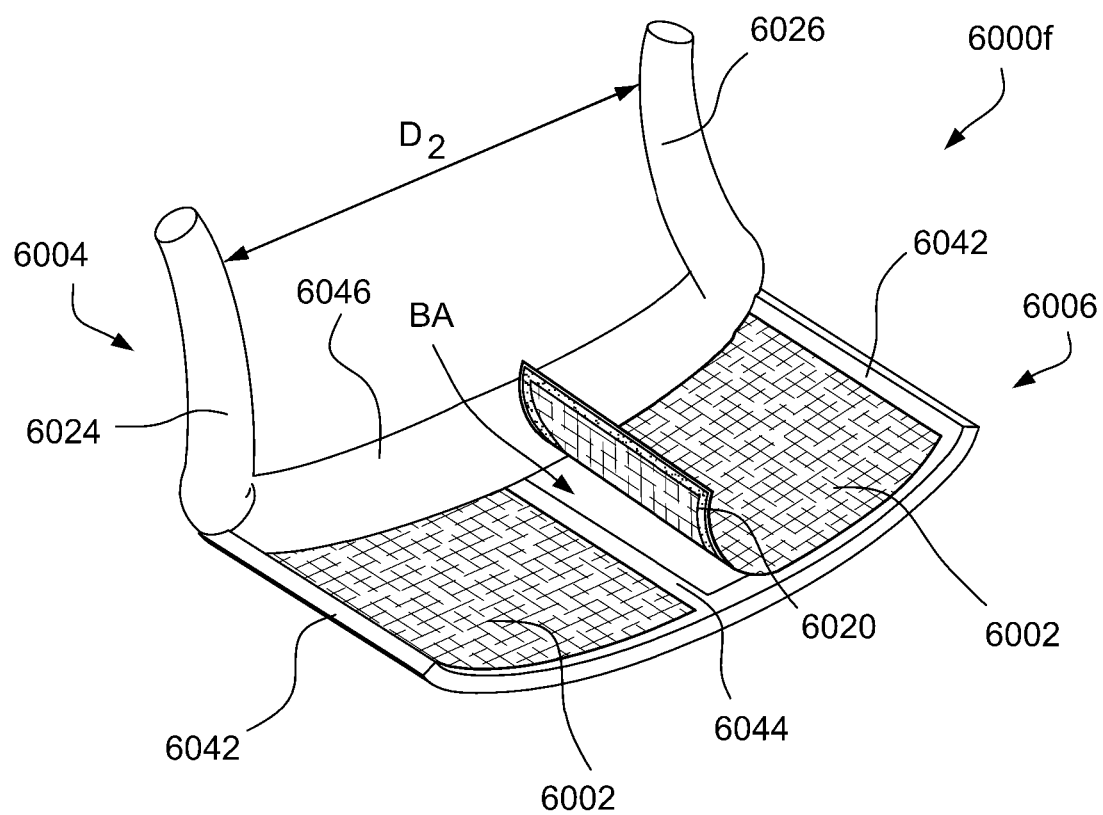

FIG. 11C is a perspective view of the frame of FIG. 11A, illustrating the frame arms in a second position where the frames are spaced further apart than in the first position.

Figure 11D:
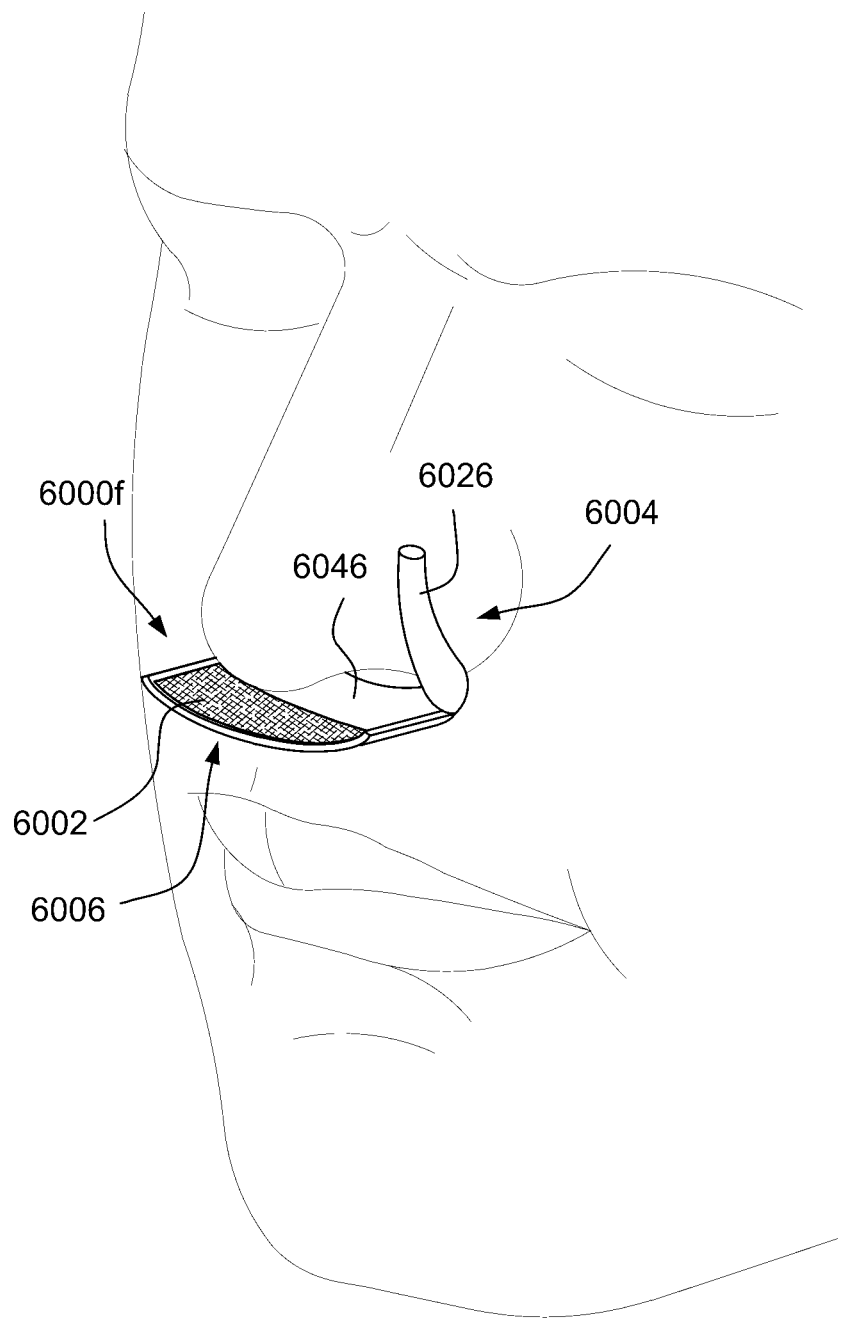

FIG. 11D is a perspective view of the frame of FIG. 11A being worn by a patient.

Figure 11E:
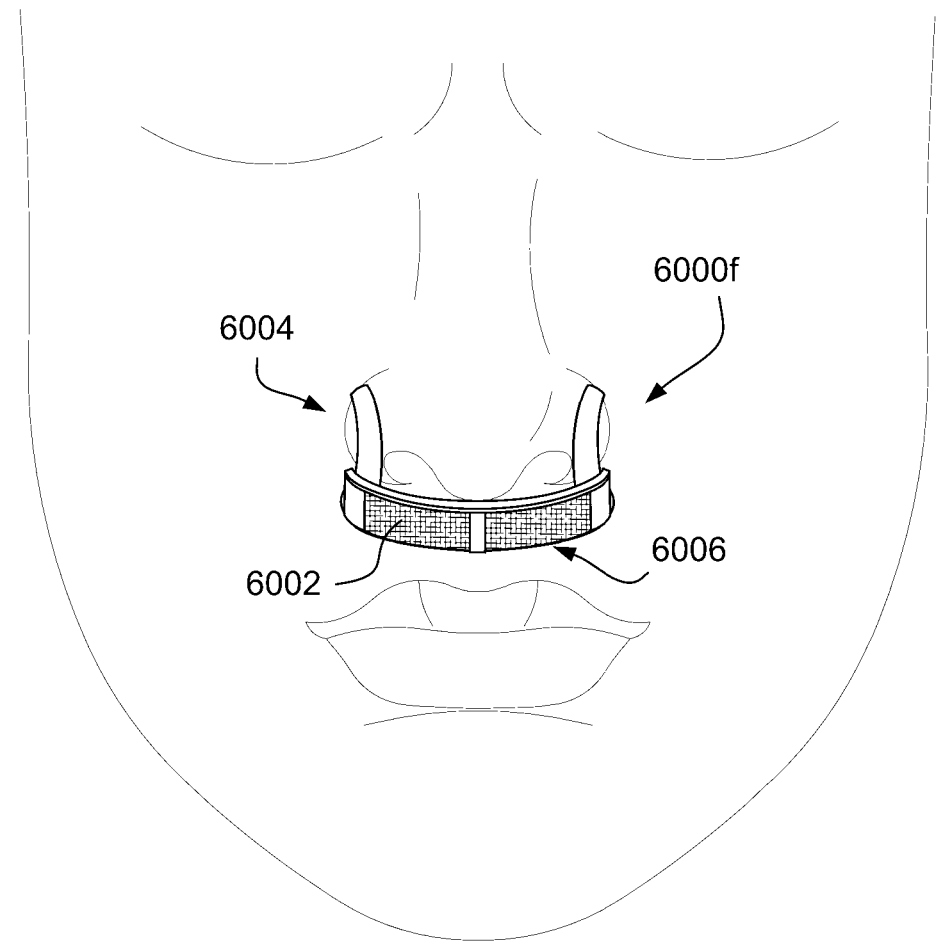

FIG. 11E is a front view of the patient of FIG. 11D wearing the frame.

Figure 12A:
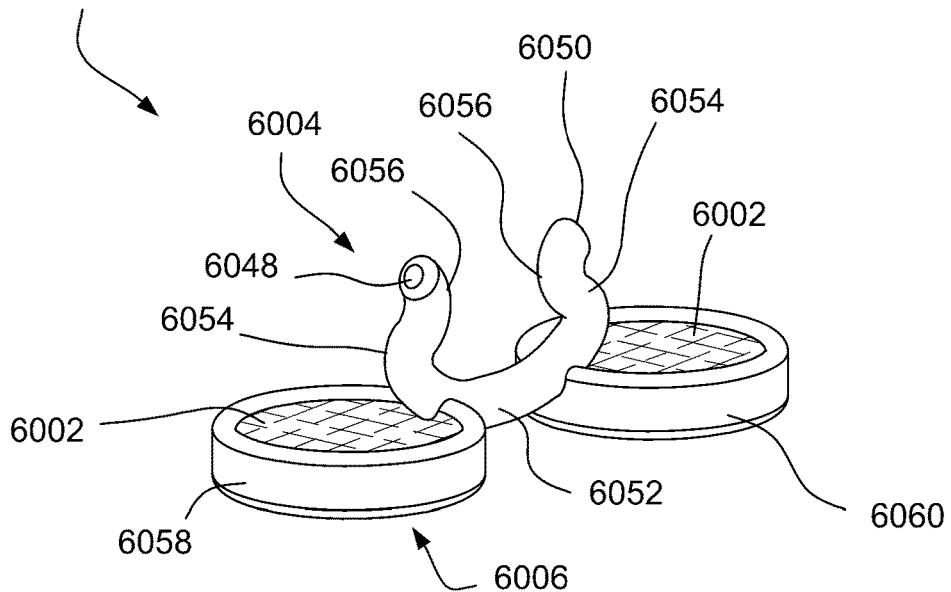

FIG. 12A is a perspective view of a seventh example of a frame, illustrating a pair of sheets coupled to the frame.

Figure 12B:
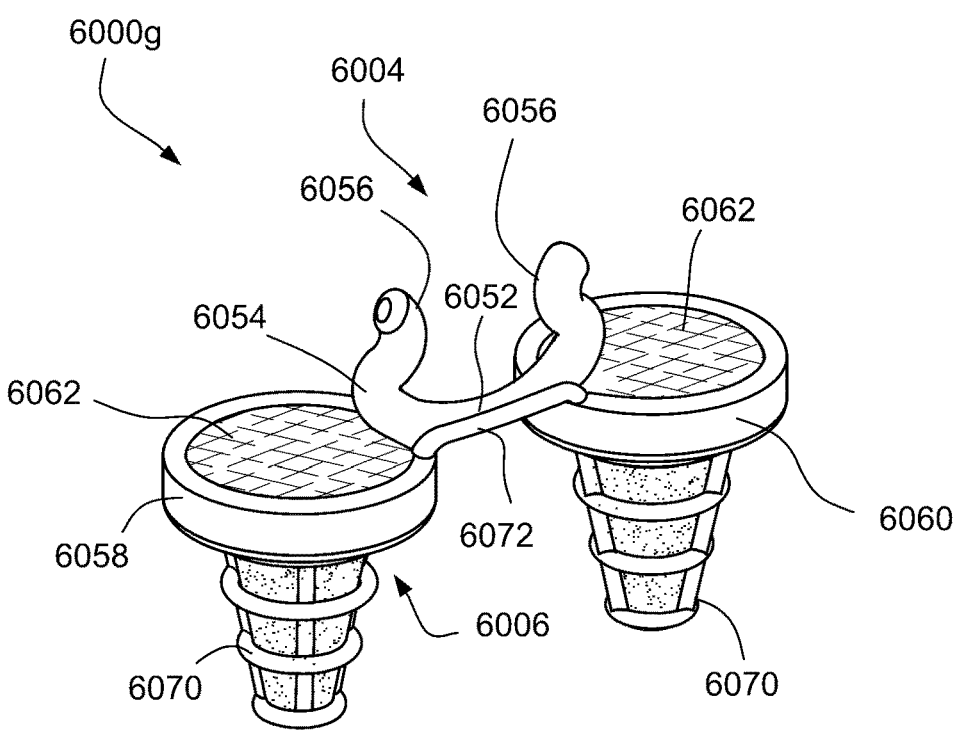

FIG. 12B is a perspective view of the frame of FIG. 12A, illustrating a pair of plugs coupled to the frame via a plug holder.

Figure 12C:
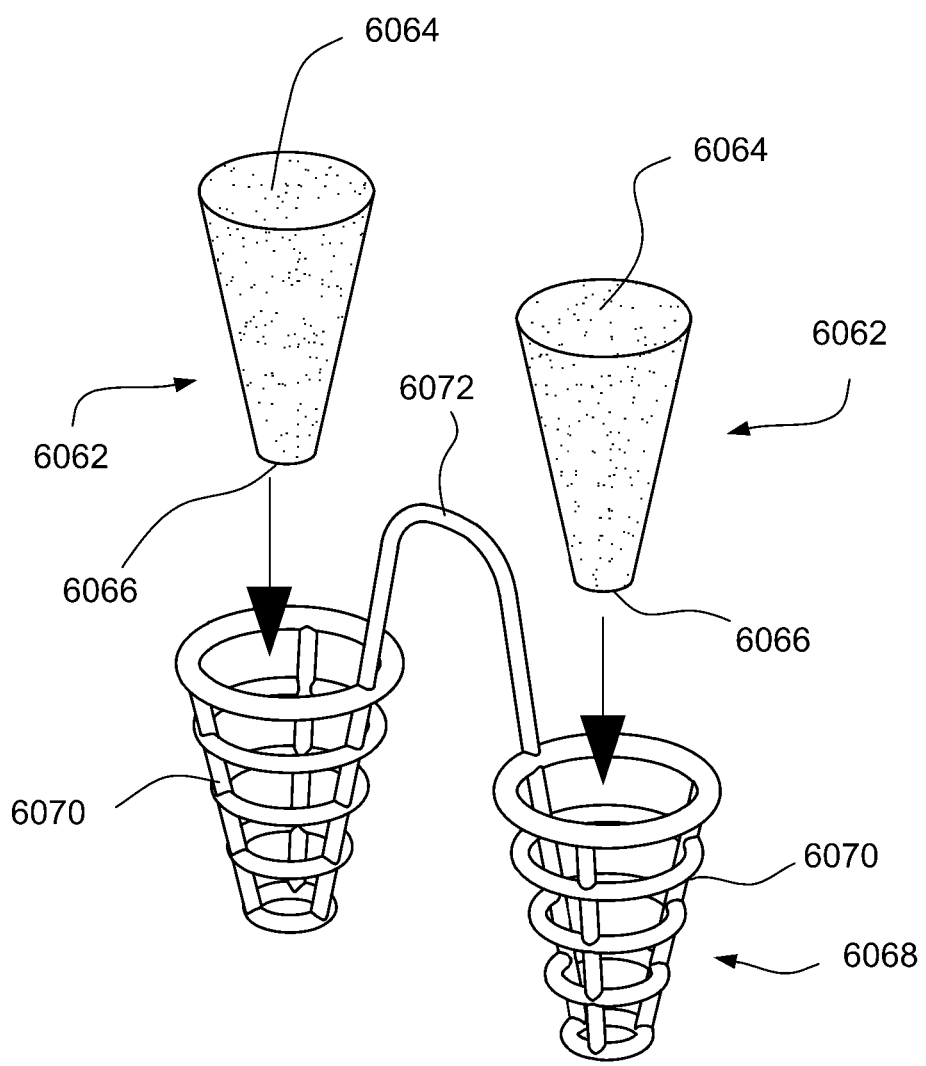

FIG. 12C is an exploded view of the plugs and plug holder of FIG. 12B.

Figure 12D:
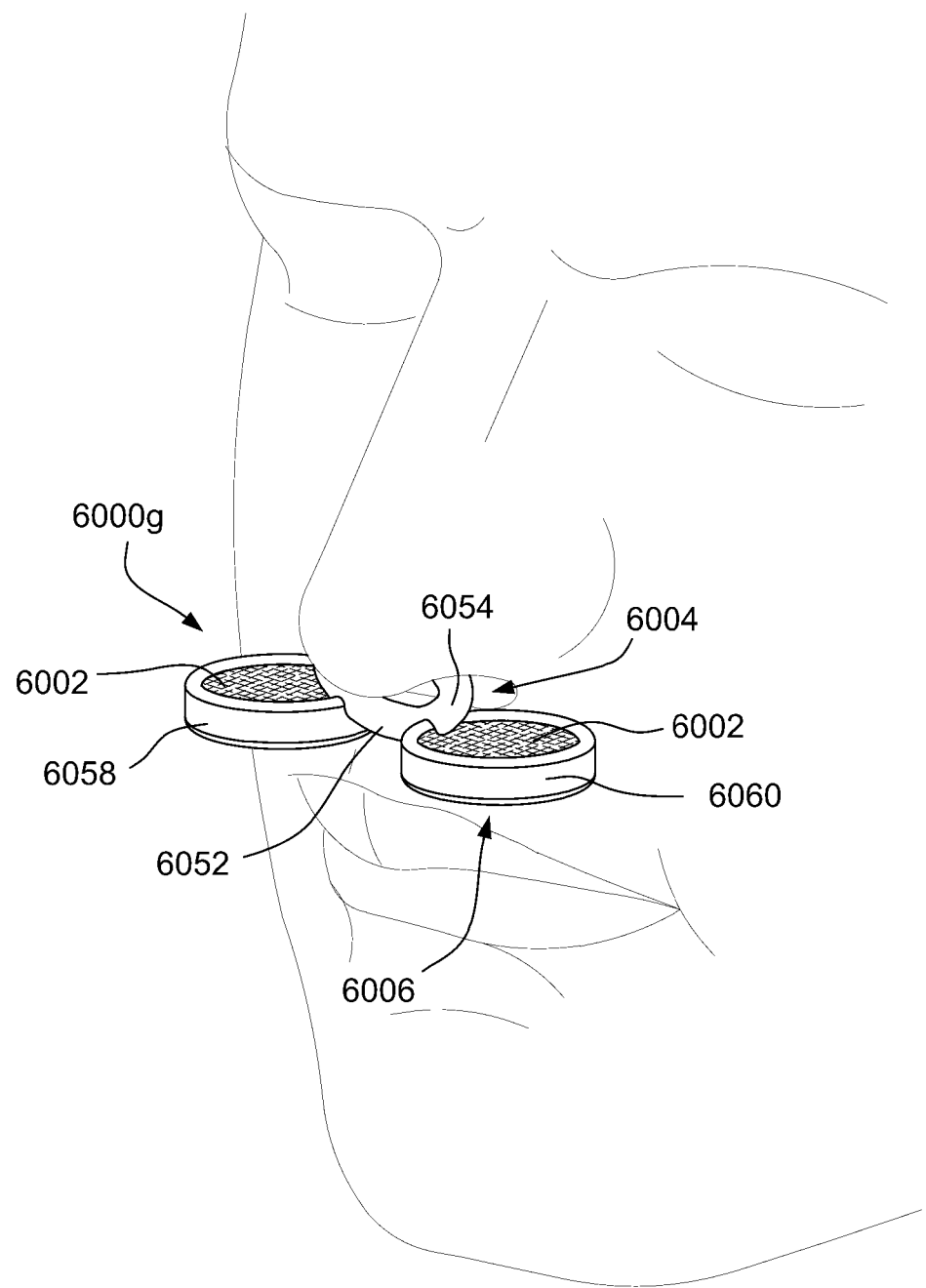

FIG. 12D is a perspective view of the frame of FIG. 12A being worn by a patient.

Figure 12E:
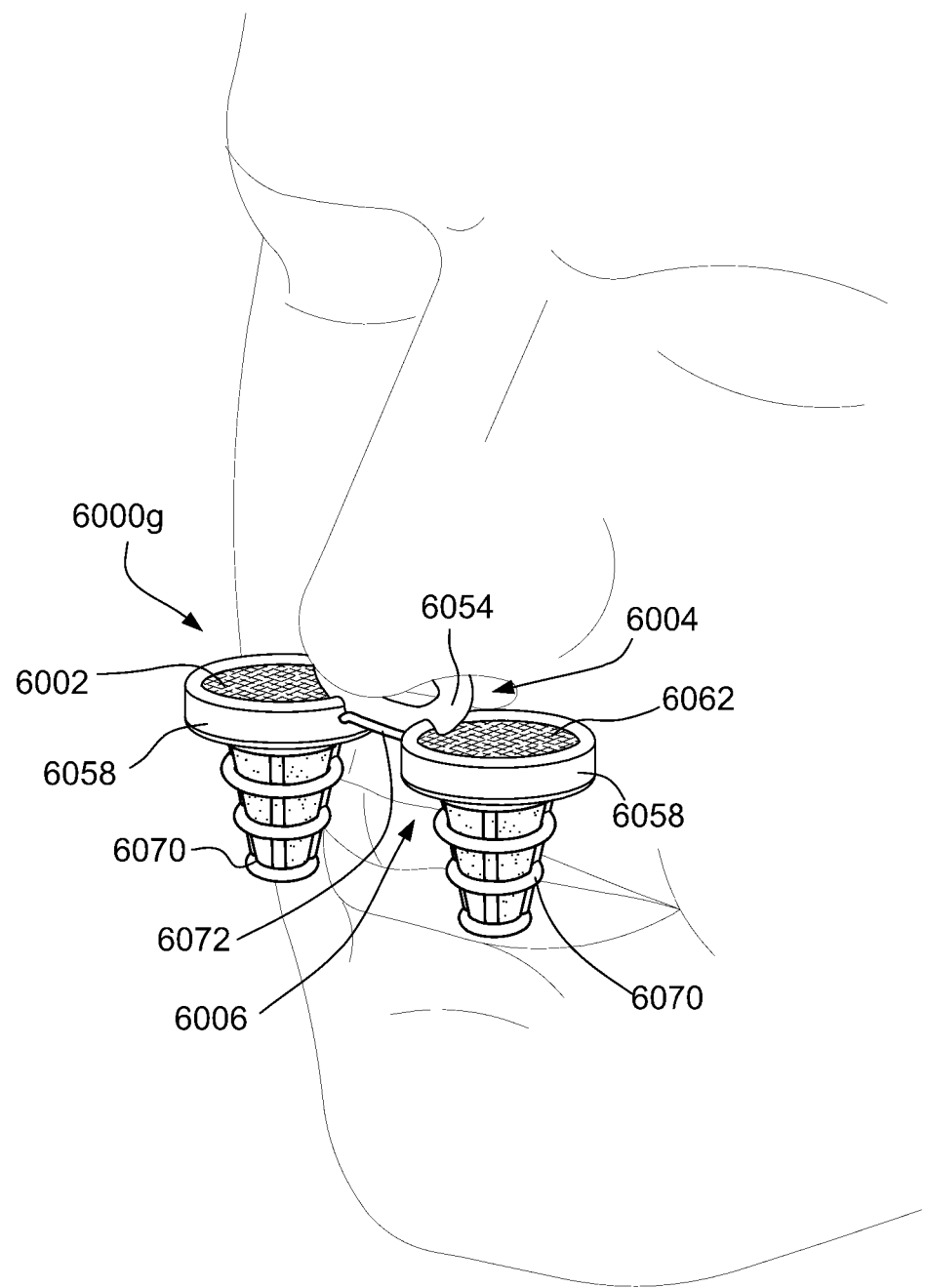

FIG. 12E is a perspective view of the frame of FIG. 12B being worn by a patient.

Figure 13A:
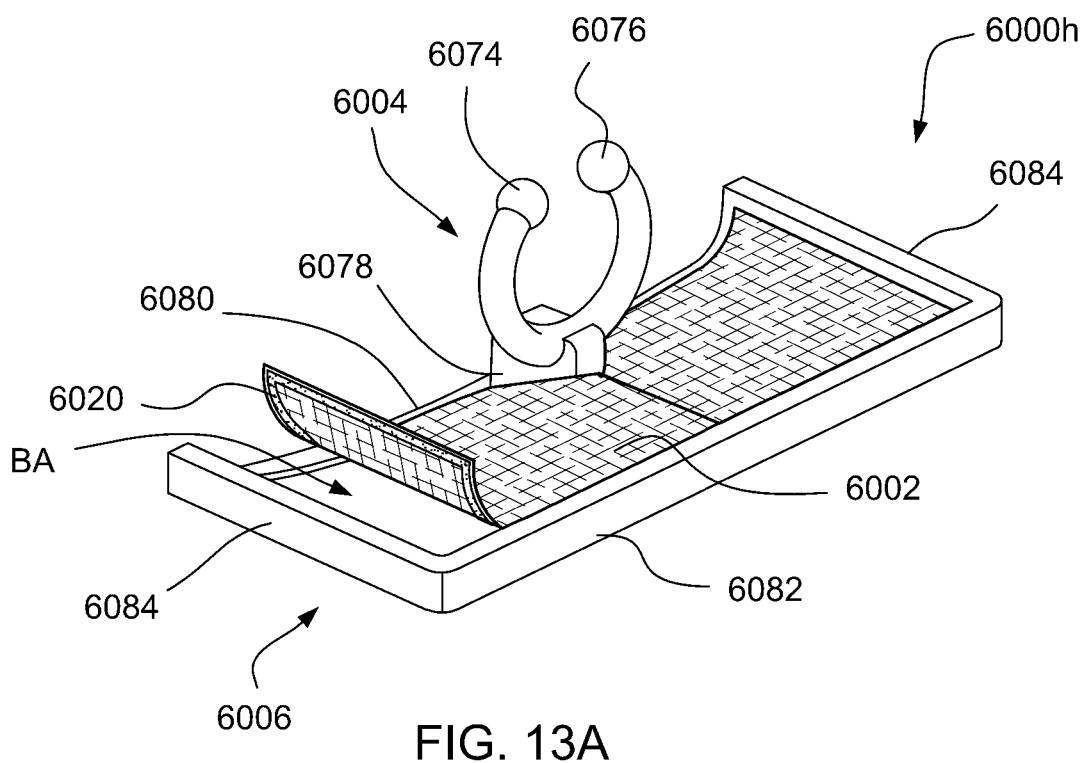

FIG. 13A is a perspective view of an eighth example of a frame supporting a single sheet of HME material.

Figure 13B:
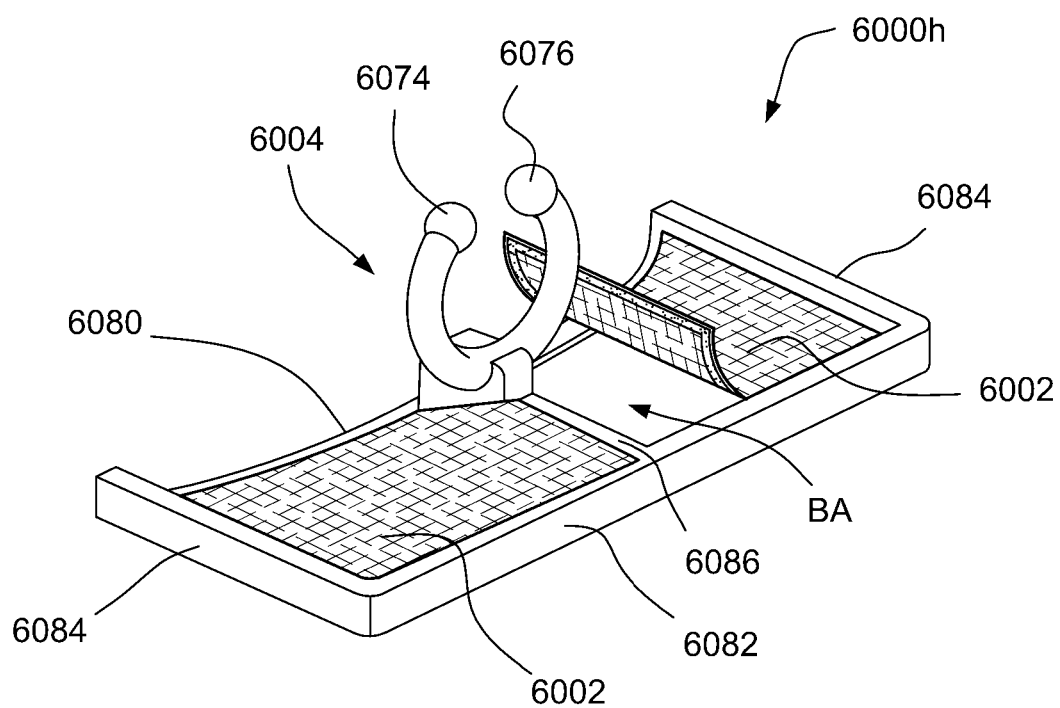

FIG. 13B is a perspective view of the frame of FIG. 13A, illustrating the frame supporting a pair of sheets of HME material.

Figure 13C:
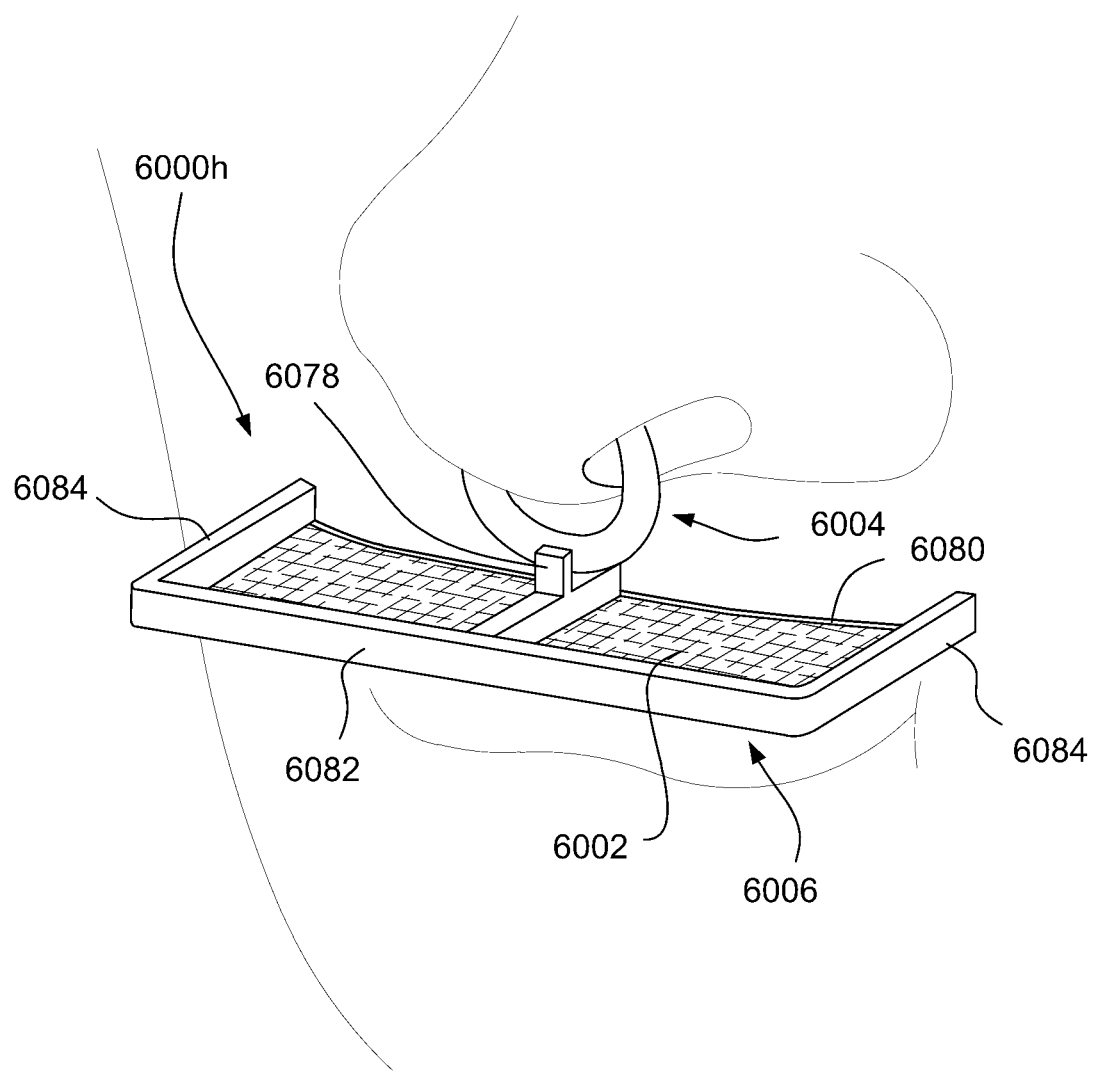

FIG. 13C is a perspective view of the frame of FIG. 13A being worn by a patient.

Figure 14A:
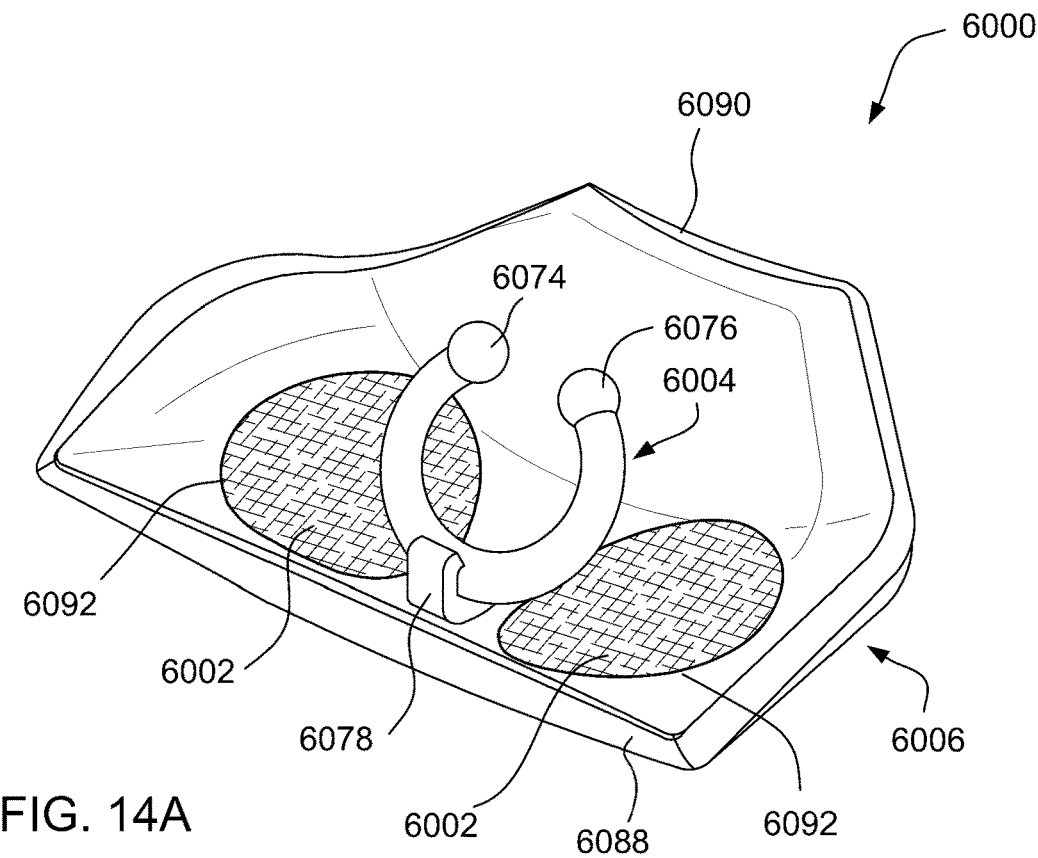

FIG. 14A is a perspective view of a ninth example of a frame, illustrating a pair of sheets coupled to the frame.

Figure 14B:
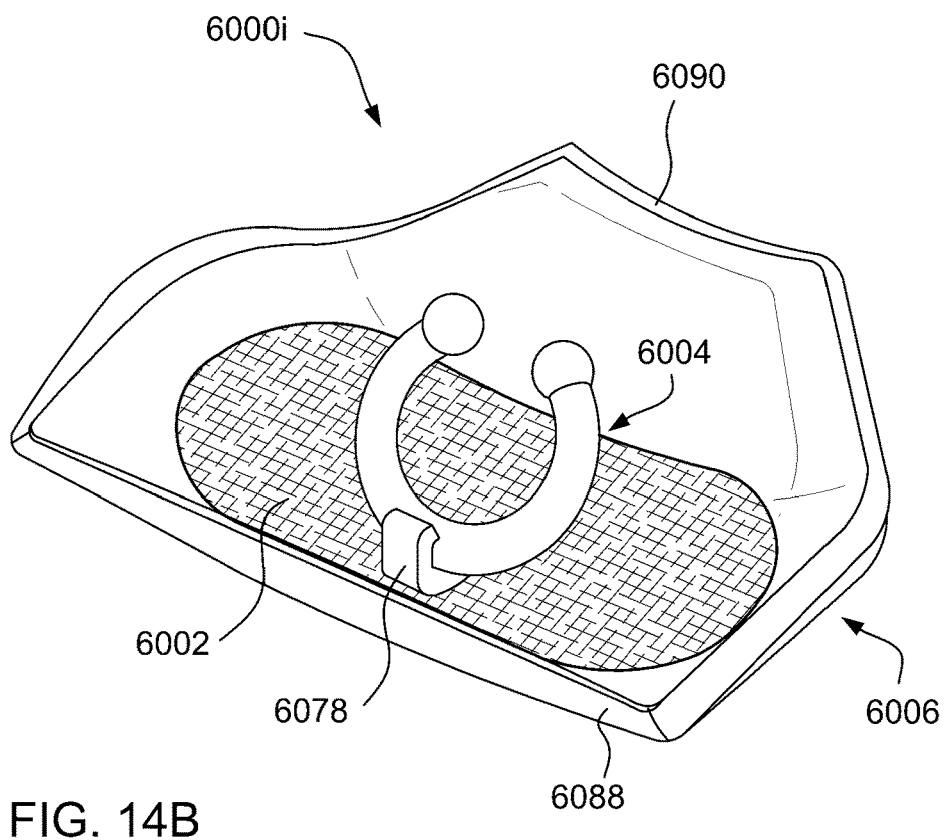

FIG. 14B is a perspective view of the frame of FIG. 14A, illustrating a single sheet coupled to the frame.

Figure 14C:
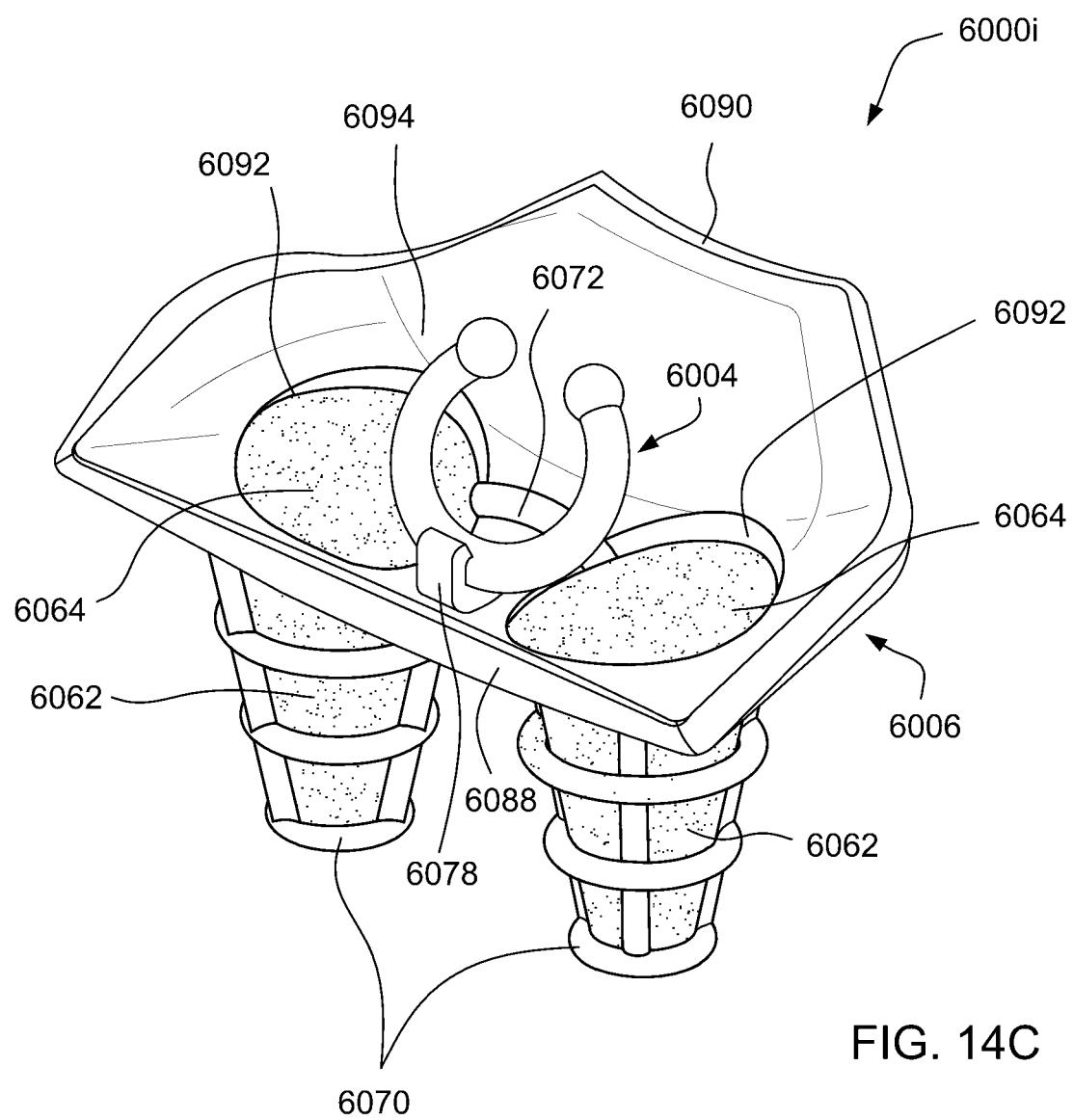

FIG. 14C is a perspective view of the frame of FIG. 14A, illustrating a pair of plugs coupled to the frame via a plug holder.

Figure 14D:
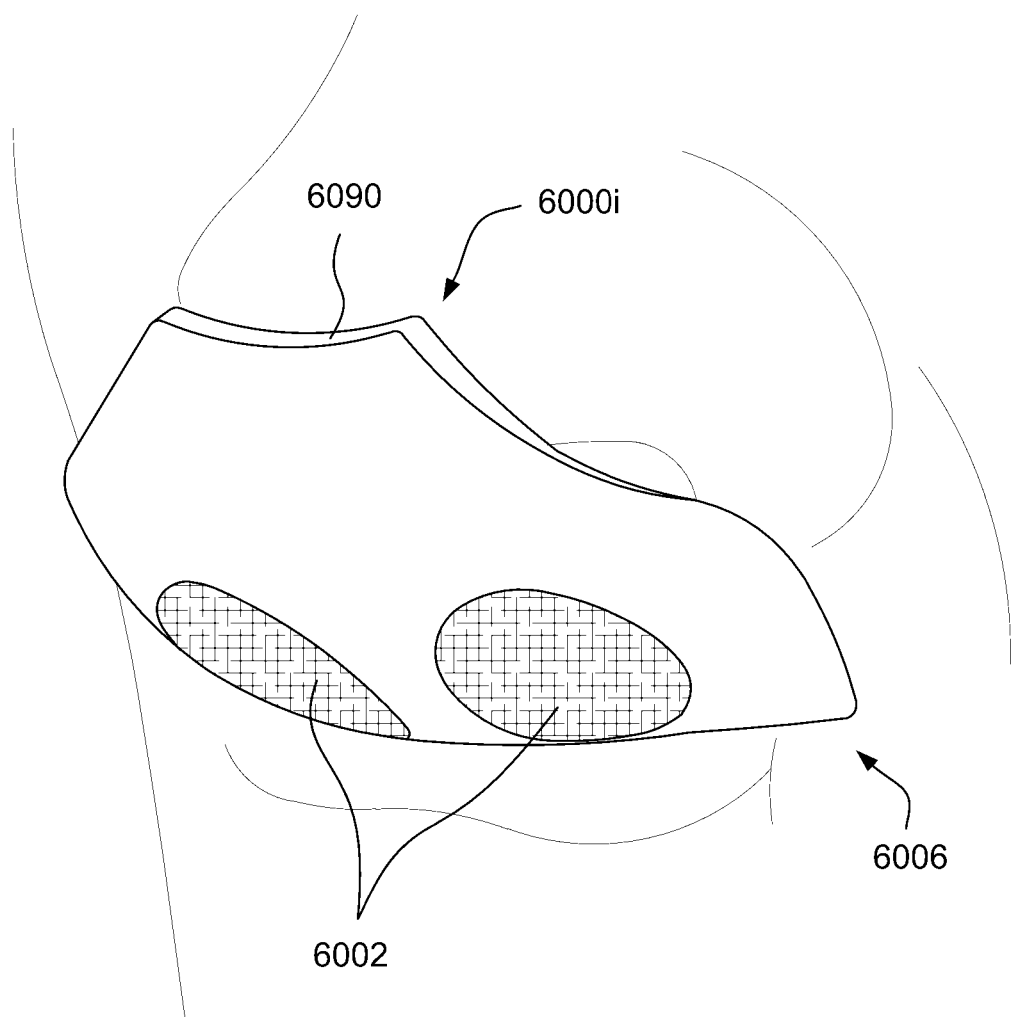

FIG. 14D is a perspective view of the frame of FIG. 14A being worn by a patient.

Figure 14E:
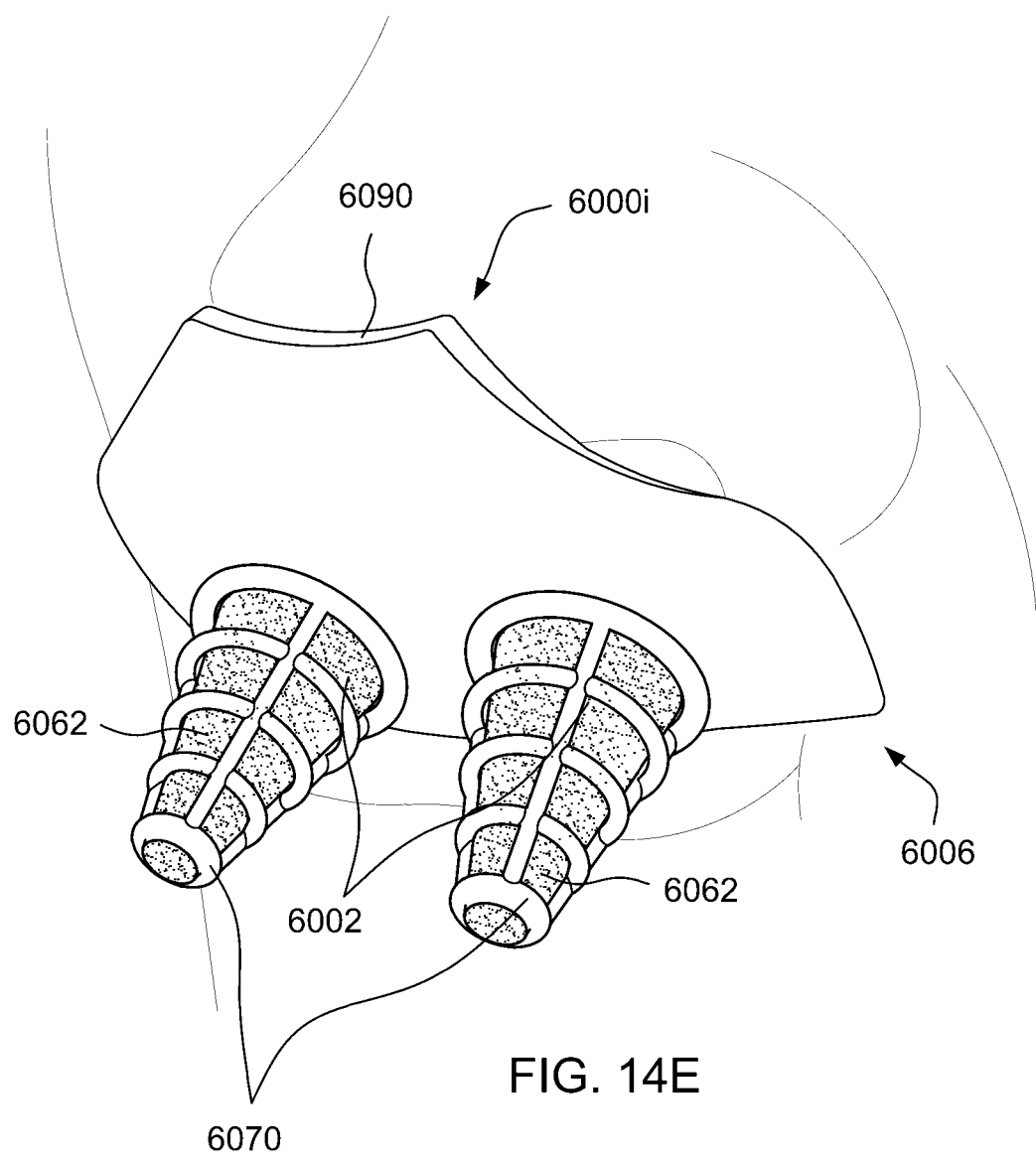

FIG. 14E is a perspective view of the frame of FIG. 14C being worn by a patient.

Figure 15A:
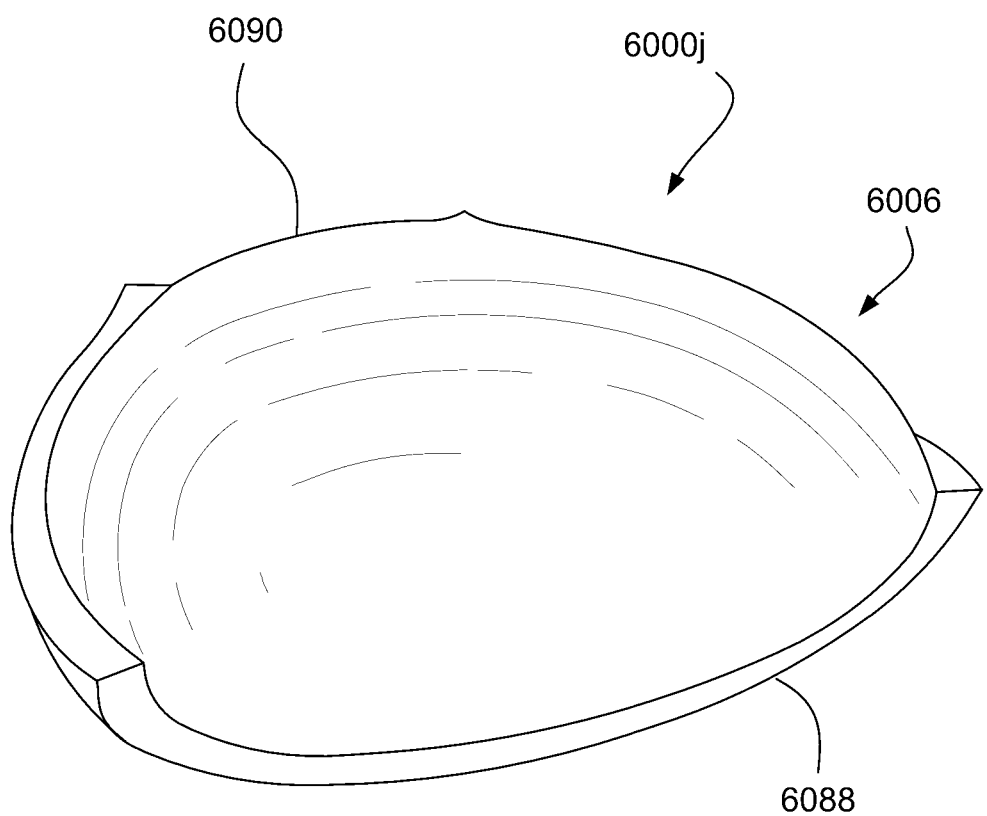

FIG. 15A is a perspective view of a tenth example of a frame.

Figure 15B:
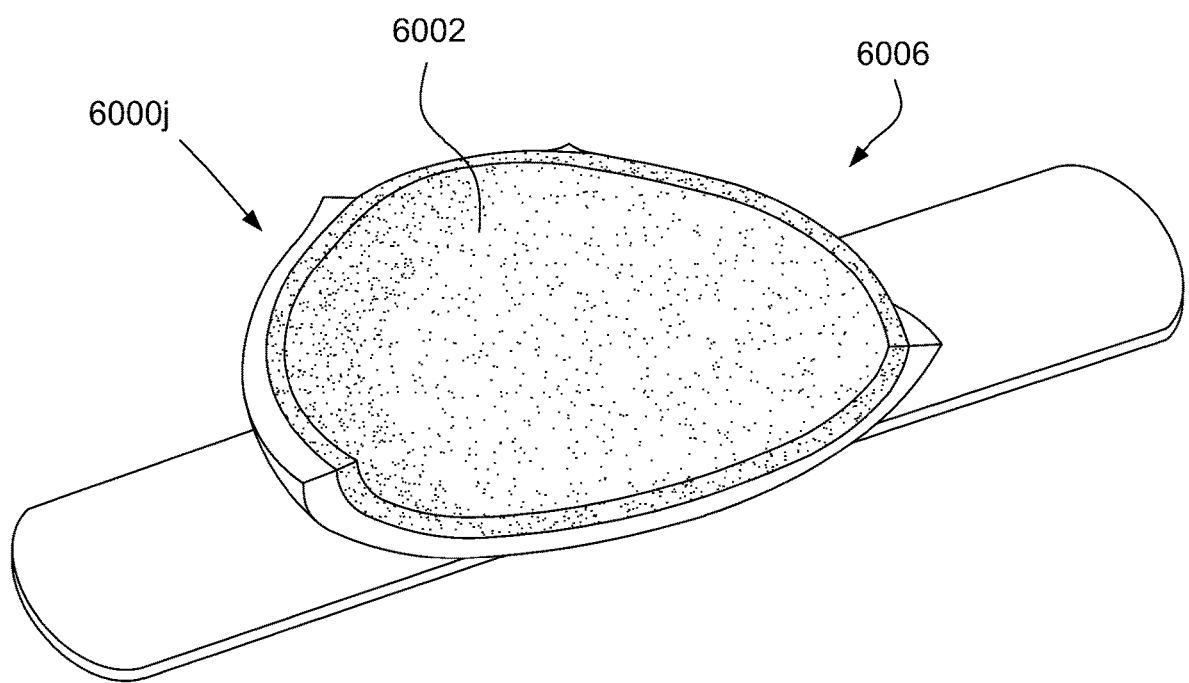

FIG. 15B is a perspective view of the frame of FIG. 15A, illustrating layers of HME material coupled to the frame.

Figure 15C:
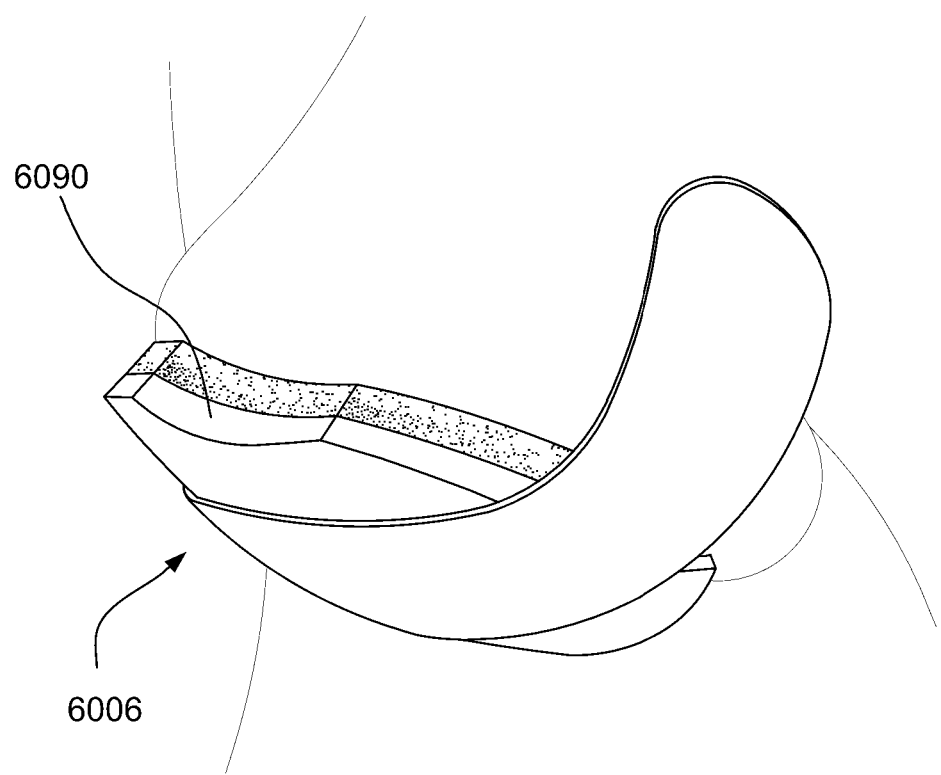

FIG. 15C is a perspective view of the frame of FIG. 15A being worn by a patient.

Figure 16A:
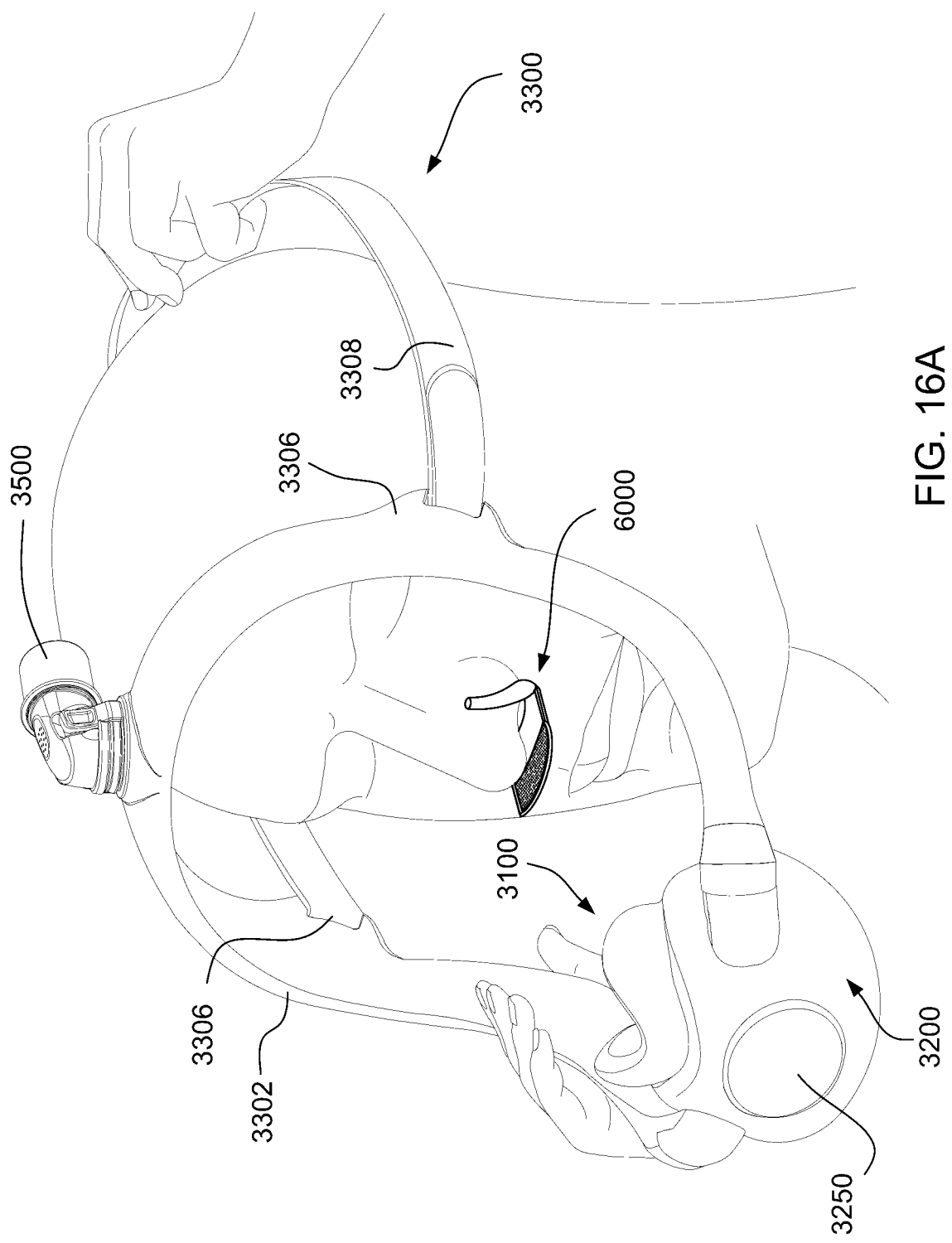

FIG. 16A is a perspective view of a patient wearing any one of the frames of FIGS. 6A-15C, and donning a first example of a patient interface.

Figure 16B:
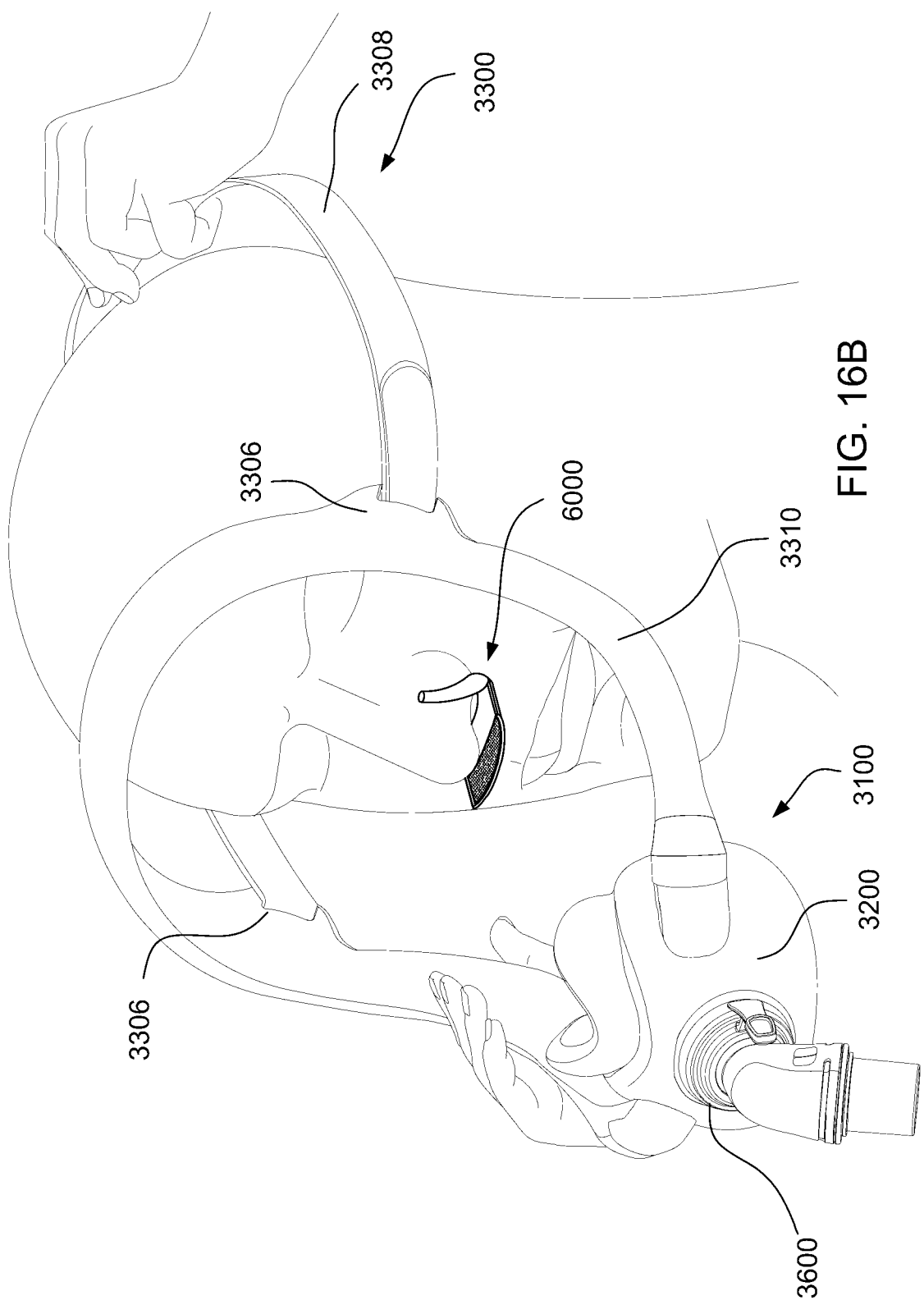

FIG. 16B is a perspective view of a patient wearing any one of the frames of FIG. 6A-15C, and donning a second example of a patient interface.

Figure 17A:
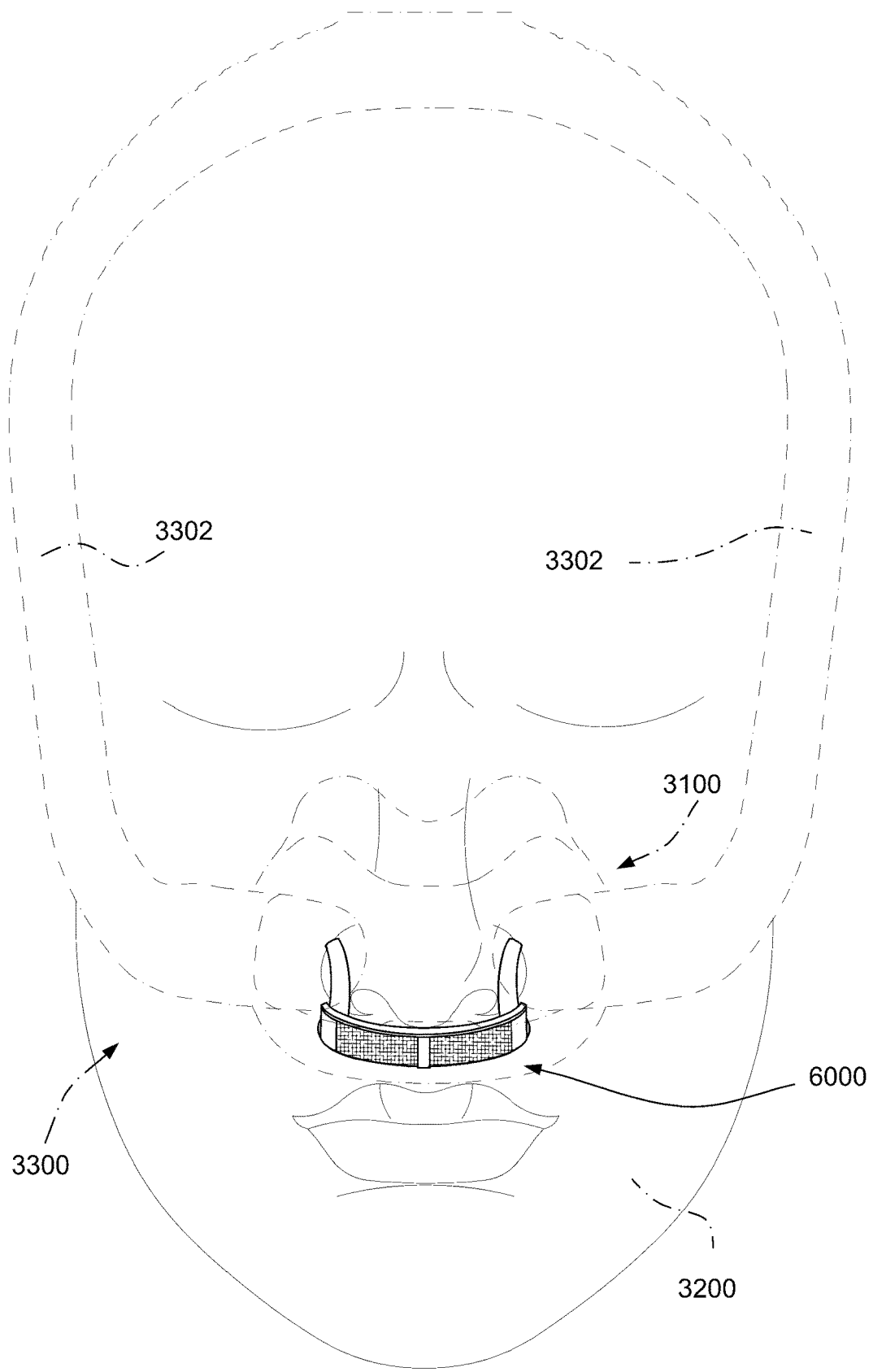

FIG. 17A is a perspective view of the patient of FIG. 16A wearing the patient interface.

Figure 17B:
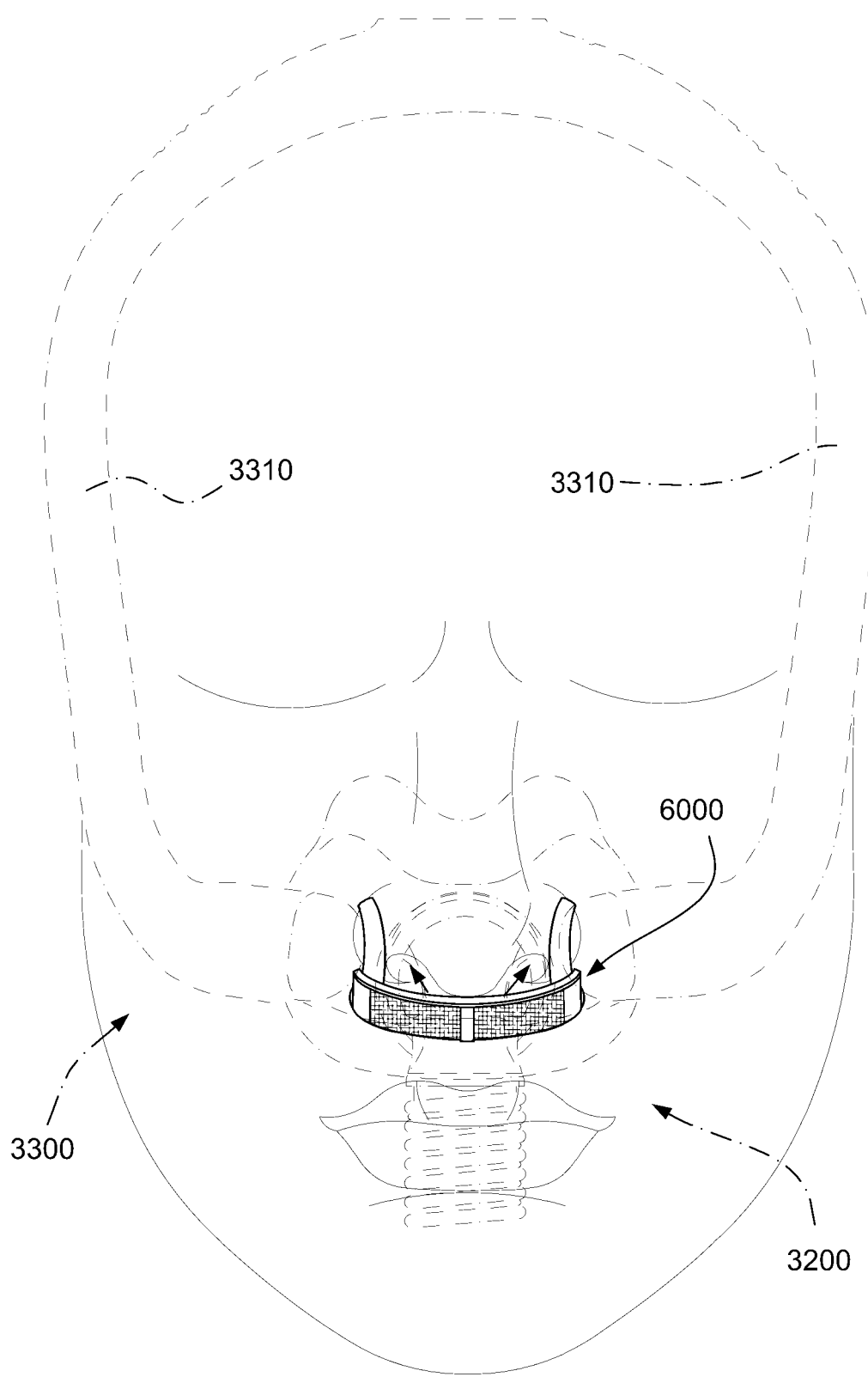

FIG. 17B is a perspective view of the patient of FIG. 16B, wearing the patient interface.

Figure 18A:
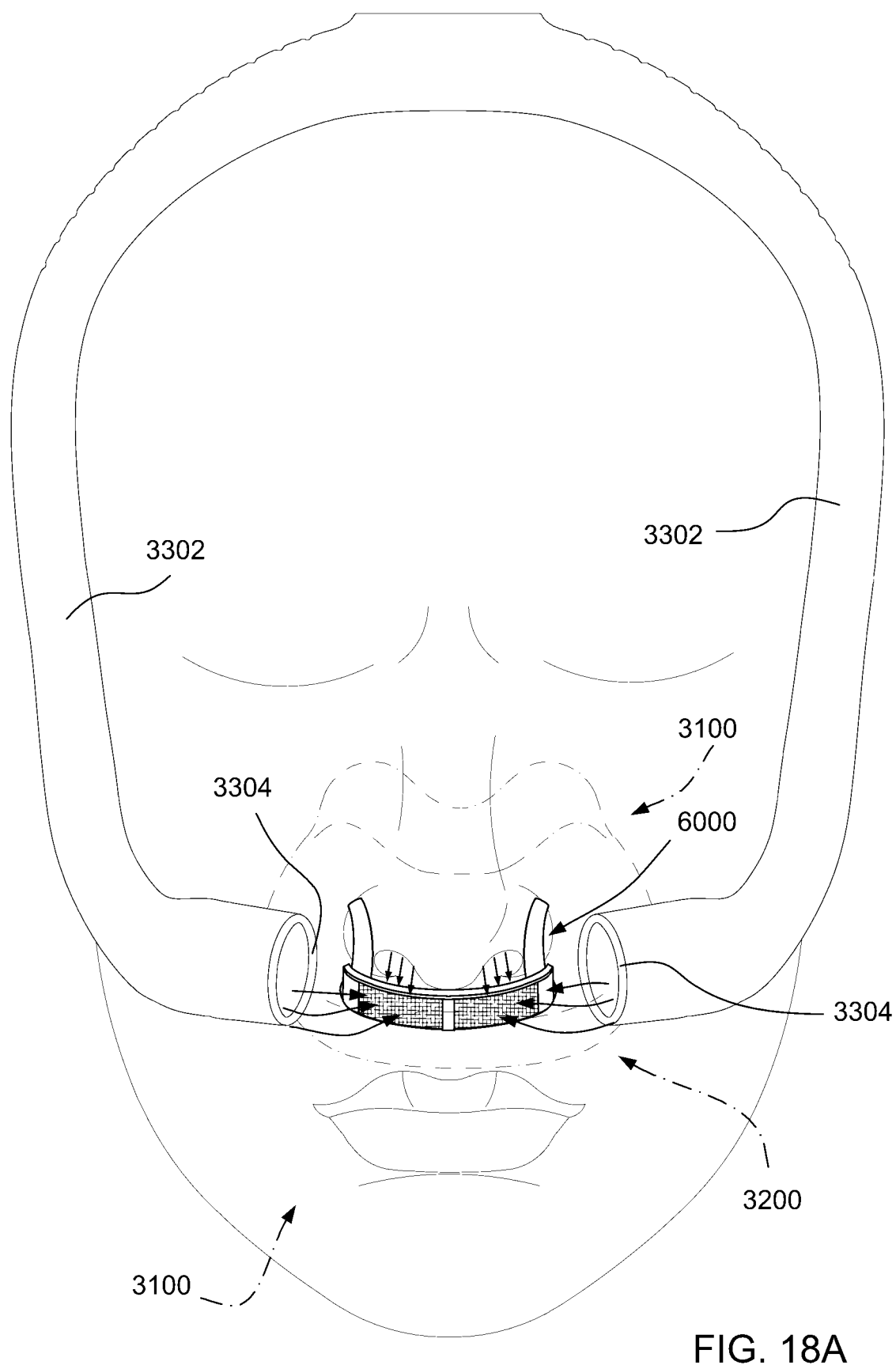

FIG. 18A is a cross-sectional view of FIG. 17A, illustrating a flow of air passing through the HME material prior to entering and exiting the patient's nares.

Figure 18B:
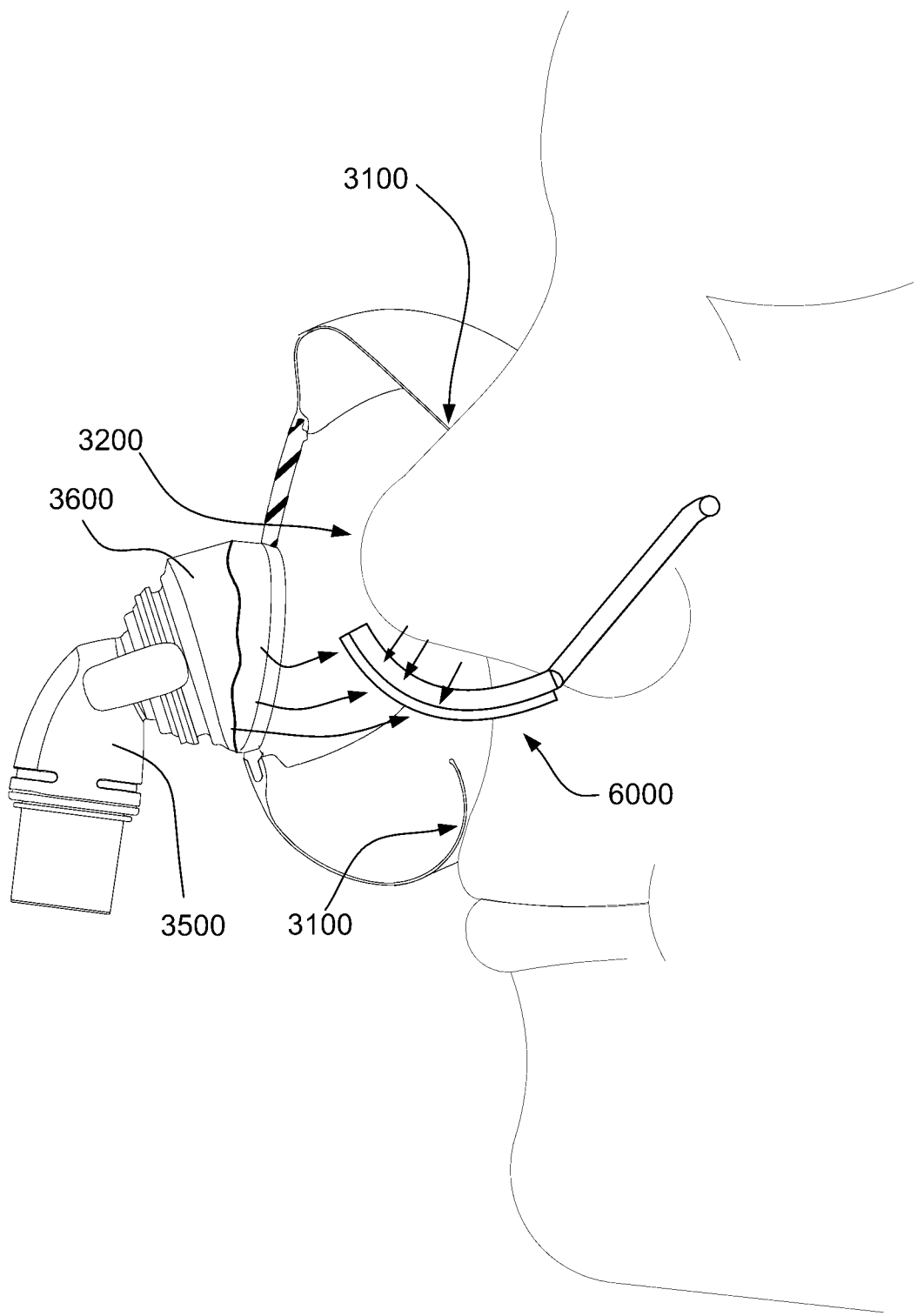

FIG. 18B is a cross-sectional view of FIG. 17B, illustrating a flow of air passing through the HME material prior to entering and exiting the patient's nares.

Figure 19A:
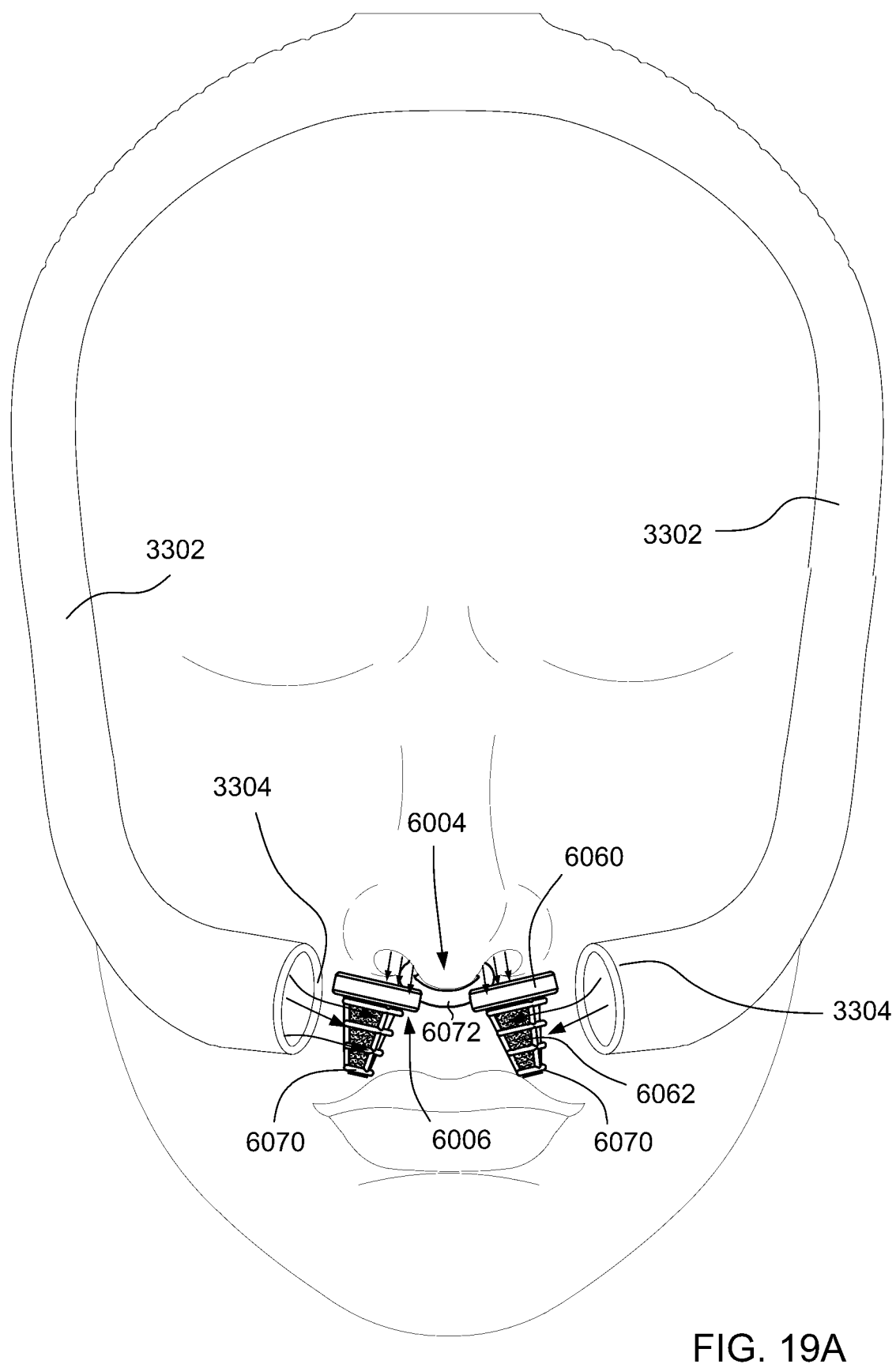

FIG. 19A is a cross-sectional view of a patient wearing the frame from FIG. 12B, illustrating a flow of air from a first patient interface passing through the HME material prior to entering and exiting the patient's nares.

Figure 19B:
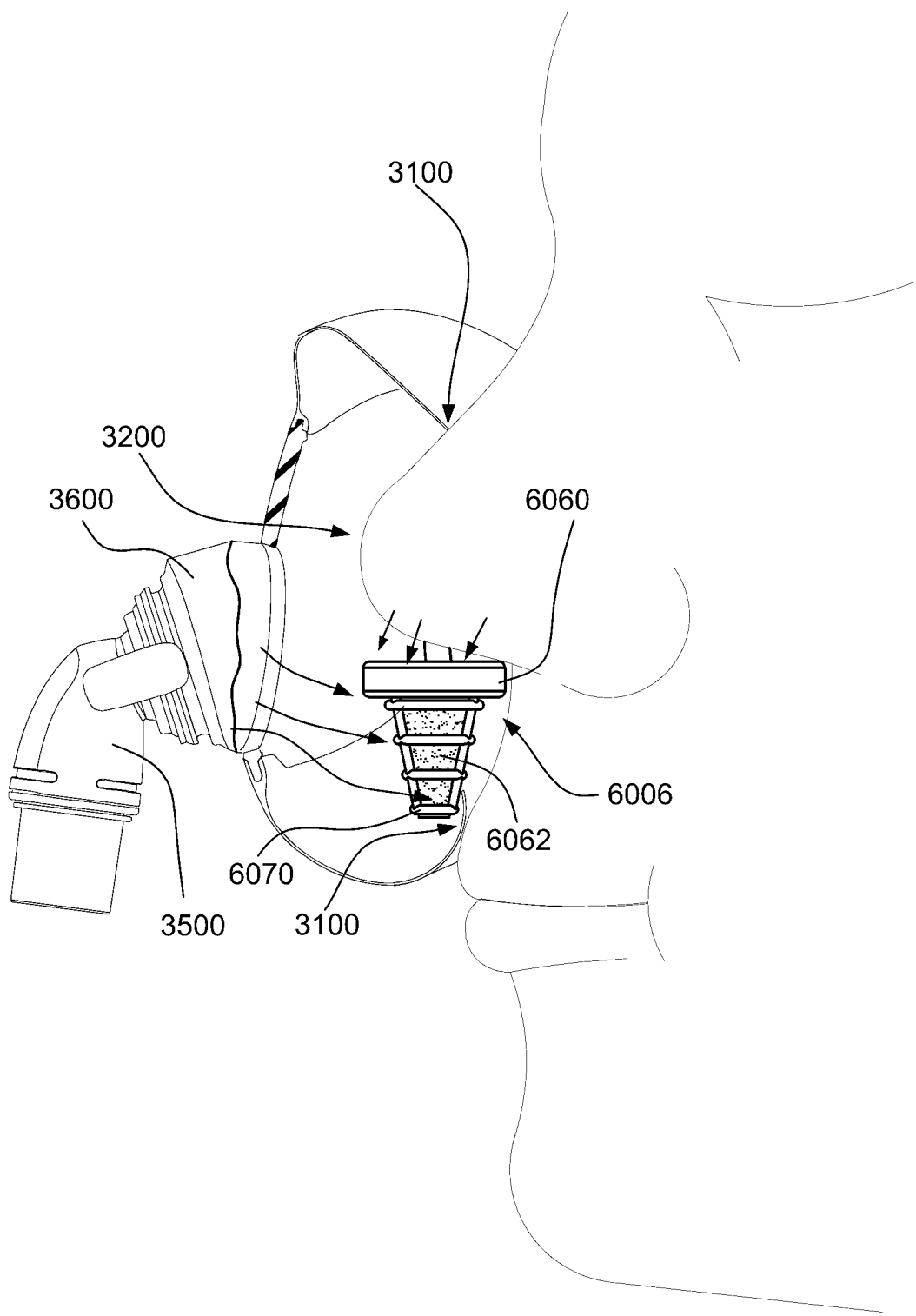

FIG. 19B is a cross-sectional view of a patient wearing the frame from FIG. 12B, illustrating a flow of air from a second patient interface passing through the HME material prior to entering and exiting the patient's nares.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cm1H$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs-the actual sealing surface-may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form (see e.g., FIG. 3A), the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure 3100 into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

In certain forms (see e.g., FIGS. 16A, 17A, 18A and 19A), the positioning and stabilizing structure 3300 includes hollow tubes or conduits 3302 that convey pressurized air toward the plenum chamber 3200. The hollow tubes 3302 extend along sides of the patient's face (e.g., the right and left cheek), toward a crown of the patient's head. The hollow tubes 3302 are constructed at least partially from an impermeable material in order to limit the pressurized air from escaping. The hollow tubes 3302 are coupled to the plenum chamber 3200, so that the air they convey is directed directly into the plenum chamber 3200, and toward the patient's airways. The hollow tubes 3302 may also assist in retaining the plenum chamber 3200 and seal-forming structure 3100 in a therapeutically effective position on the patient's head.

In some forms, the tubes 3302 may include a tab 3306 with an opening or eyelet. A strap 3308 (e.g., a textile strap) may be threaded through each of the tabs 3306, and extend around a posterior portion of the patient's head. For example, the strap 3308 may contact the patient's parietal bone and/or the occipital bone.

In certain forms, the positioning and stabilizing structure 3300 may still utilize hollow tubes 3302 even through the pressurized air is delivered to the plenum chamber 3200 through a connection port 3600. The plenum chamber 3200 may include a plug 3250 (see e.g., FIG. 16A) to selectively fill an opening. When the tubes 3302 are used to convey pressurized air, the plug 3250 is coupled to the plenum chamber 3200. When the connection port 3600 is used, the plug 3250 is removed and the tubes 3302 act as straps without conveying air. The plug 3250 may be used to fill the space previously occupied by the elbow 3500 between the tubes 3302.

In certain forms (see e.g., FIGS. 16B and 17B), the hollow tubes 3302 may be replaced with straps 3310 (e.g., textile straps) when the connection port 3600 is used to supply the plenum chamber with pressurized air. In other words, textile straps 3310 (e.g., flat and without a hollow center) are connected to the plenum chamber 3200. The straps 3310 may extend along substantially the same path as the tubes 3302. For example, the straps 3310 may extend toward a superior portion of the patient's head, and may overlay the masseter muscle, the temporal bone, parietal bone, and/or the frontal bone. The straps 3310 may also include the tabs 3306 with the eyelets that can receive the rear strap 3308.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket. For example, an elbow 3500 is shown connected to a connection port 3600 in FIGS. 18B and 19B.

5.3.6 Connection Port

Connection port 3600 allows for connection to the air circuit 4170. The connection port may be connected to the plenum chamber 3200 (see e.g., FIG. 16B), or may be connected to hollow tubes 3302 proximate to a top of the patient's head (see e.g., FIG. 16A).

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a pressure generator 4140, and transducers 4270. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to a central controller.

In one form, the input device 4220 may be constructed and arranged to allow a person to select a value and/or a menu option.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated therewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000.

5.6 Humidifier

In one form of the present technology there is provided a humidifier 5000 (e.g. as shown in FIG. 4B) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

5.7 Heat and Moisture Exchanger (Hme)

A heat and moisture exchanger (HME) 6000 can be used with the patient interface 3000 in order to provide the patient with a humidified flow of air without the use of a humidifier 5000. In other words, the HME 6000 allows the patient to inhale air with a greater humidity as compared to the ambient. Instead of heating a reservoir of water, the HME 6000 uses the patient's own body heat, and captures and stores the exhaled water vapor to be reused when the patient inhales. In other words, a flow of air picks up the moisture from the previously exhaled air, and reintroduces the moisture into the patient's lungs as they inhale.

The HME 6000 is ideally positioned between the connection port 3600 and an entrance to the patient's airways (e.g., the mouth, the nares). The HME 6000 is also ideally positioned between the vent 3400 and the patient's airways. This way, air introduced into the plenum chamber 3200 through the connection port 3600 passes at least partially through the HME 6000 prior to reaching the patient's airways. Similarly, air exhausted from the plenum chamber 3200 through the vent 3400 passes at least partially through the HME 6000 prior to reaching the ambient. In other words, at least one flow path of air at the therapeutic pressure passes through the HME 6000 before being inhaled by the patient. Similarly, at least one flow path of air exhale by the patient passes through the HME 6000 before venting to the ambient.

The HME 6000 of FIGS. 6A-18B may be positioned proximate to the patient's nose, and only intersect airflow into and out of the patient's nares. In other words, when the patient breathes through their nose (i.e., inhale or exhale), at least some of the airflow would pass through the HME 6000. However, little to no airflow would pass through the HME 6000 when the patient breathes through their mouth (i.e., inhale or exhale). Having the HME 6000 positioned in front of only the patient's nose would assist in providing a low profile look for the HME 6000. For example, the total area that the HME 6000 would need to cover is less than if the HME 6000 covered both the patient's nose and mouth. Additionally, the HME 6000 could be positioned close to the patient's nose, so as to not extend substantially into their view path. Creating this low profile look may give the HME 6000 a less clinical feel, or may provide the patient with a less obtrusive device. These and other reasons may assist with patient compliance, and encourage the patient to consistently wear the HME 6000 while using the patient interface 3000.

In some forms, the HME 6000 may be larger than the patient's nose. In other words, the HME 6000 may extend wider than the patient's nose (e.g., up to or exceeding a distance between the patient's nasal ala) and/or longer than the patient's nose (e.g., greater than a distance between the patient's subnasale and pronasale). Being larger than the patient's nose may provide a larger surface area to better assist with heat and moisture exchange. However, the HME 6000 may not be so large that low profile design is eliminated. For example, the HME 6000 may extend wider than the patient's nares but may not substantially exceed the patient's mouth width. The HME 6000 may also not extend substantially beyond the patient's pronasale in use. In either case, the HME 6000 may be larger than the patient's naris openings in order to capture a greater percentage of inhale and/or exhaled air, while not extending substantially beyond the patient's physical structures (e.g., the patient's nose). In this way, the HME 6000 may feel less intrusive to the patient since it is not overly large as compared to existing facial features, but the HME 6000 may also provide enough surface area to effectively produce heat and moisture exchange. As described below, the HME 6000 may also be curved to increase the surface area (e.g., as compared to a planar surface) while not eliminating the low profile shape.

In other examples (not shown), an HME may cover both the patient's nose and mouth, or may be disposed in a position such that air inhaled and exhaled through either orifice passes through the HME. This may not provide the same low profile look as the HME 6000, but may allow a greater number of patients the use on an HME device (e.g., because breaths from a patient who breathes through their mouth would pass through the HME 6000).

The HME 6000 includes an HME material 6002 (e.g., a paper, a foam, etc.) that captures the exhaled water vapor, while allowing the airflow to pass through. In other words, the HME material 6002 impedes the flow path of exhaled so that water vapor is captured, but carbon dioxide (and other exhaled gasses) may pass through and be exhausted through the vent 3400. Similarly, the HME material 6002 impedes the flow of oxygen (and other inhaled gasses) so that these inhaled gasses pick up the captured water vapor and reintroduce the water vapor to the patient's lungs. Impedance may be affected by the material itself (e.g., type of material, thickness of material, surface area of material, etc.), as well as by the position of the material (e.g., distance from the patient's nares, angle with respect to patient's nares, etc.). While a higher impedance may improve the amount of water vapor that the HME material 6002 is able to capture per breath (i.e., increase the efficiency of the HME material 6002), a higher impedance also reduces the flow rate of air into and out of the patient's airways. In other words, a higher impedance may make breathing more difficult for a patient. The HME material 6002 is therefore designed in order to maximize the efficiency of water capture while minimizing the impedance to the patient breathing.

The HME material 6002 may be a biocompatible material. In other words, the HME material 6002 may not negatively react with the patient when in contact with their skin. The HME material 6002 may also be flexible, and capable of conforming to various contours on the patient's face. In some examples, an intermediate material may be positioned between the HME material 6002 and the patient's skin. The intermediate material may be a gauze, or a similar material. The intermediate material may provide negligible impedance so as not to interfere with the effectiveness of the HME material 6002 and/or the patient's breathing.

In some forms (as shown in FIG. 6A-1), the HME material 6002 is constructed from a paper material 6002A. For example, the paper 6002A may be a corrugated paper, and include a plurality of channels or pipes 7000 extending along a length of the paper. Each pipe 7000 provides an airflow pathway along its length, so that air (e.g., pressurized air, exhaled air, etc.) may be conveyed through each individual pipe 7000 (see e.g., airflow 7002). In the illustrated form, the pipes 7000 limit airflow in a lateral direction. In other words, airflow 7002 in one pipe 7000 may not migrate to a separate pipe 7000 while contained within the corrugated paper 6002A. Thus, airflow 7002 through the corrugated paper 6002A is substantially constrained to an anterior-posterior direction (i.e., towards and away from the patient's face), and is limited from flowing in a lateral (e.g., left-right) direction. However, curving the corrugated paper 6002A may allow for airflow 7002 in the left-right direction (e.g., because individual pipes are oriented in the left-right direction).

The corrugations in the paper 6002A may provide increased stiffness and/or strength to the corrugated paper 6002A (e.g., as compared to non-corrugated paper). In other words, the corrugated paper 6002A may hold its shape and be limited from substantially bending and/or flexing (e.g., about axes transverse to the pipes 7000). For example, the corrugated paper 6002A may be able to hold its shape once assembled into the HME 6000, so that the pipes 7000 are properly oriented with respect to the patient's face in order to provide appropriate flow paths (e.g., for the pressurized inhaled air and/or the exhaled air).

In some forms (as shown in FIG. 6A-2), the HME material 6002 is constructed from a foam material 6002B. The foam material may be (i) reticulated polyurethane, (ii) reticulated polyurethane coated in Calcium Chloride salt, (iii) open cell polyurethane, (iv) open cell polyurethane with additives to enhance moisture capture, and/or, (v) any other suitable foam that allows for heat and moisture exchange. The chemistry and/or type of foam used may be selected based on the application of the HME 6000. For example, the flexibility, impedance, and/or other similar properties of the foam 6002B may influence which type of HME 6000 is used and/or how far the foam HME material 6002B is disposed from the patient's face.

Unlike corrugated paper 6002A, foam 6002B may allow airflow 7004 in any direction. For example, the airflow 7004 is not constrained along a longitudinal length in the foam 6002B as it is in the corrugated paper 6002A (e.g., along the length of the pipe 7000). In other words, there is not a structure that linearly conveys airflow through the length of the foam 6002B. Instead, airflow 7004 through the foam 6002B may flow in any direction (e.g., along the x-axis, the y-axis, and/or the z-axis), and/or may change directions as it flows through the foam 6002B. This expands the possible orientations for the HME material 6002 when a foam 6002B is used, because bending the foam 6002B will not necessarily preclude and/or obstruct different flow paths (e.g., flow paths may not be pinched shut). Additionally, foam 6002B may be more deformable than corrugated paper 6002A, and may be able to better conform to a patient's face and/or may be able to fit a wider range of patient's faces (e.g., with different contours or other facial features).

In certain forms, the HME 6000 is intended to couple to the patient separately from the patient interface 3000. In other words, the HME 6000 can be worn and supported by the patient's face independently of whether or not the patient is using the patient interface 3000. For example, the HME 6000 may be secured to the patient's nose in a low profile configuration, so that the patient interface 3000 may be donned and doffed without disturbing the position of the HME 6000. This may be useful in providing the HME 6000 as a retrofit to an existing patient interface 3000. In other words, a patient interface 3000 that may not include an HME, or any other way to provide moisture exchange, may be used with the HME 6000 so that a patient may still obtain the benefits of heat and moisture exchange, even when the patient interface 3000 (e.g., the plenum chamber 3200 and/or the seal-forming structure 3100) does not include a way to support an HME 6000.

An element of the low profile shape of the HME 6000 described above is its complementary shape to that of the patient interface 3000. Specifically, the HME 6000 may include a shape that is complementary to the shape of the plenum chamber 3200. Though the plenum chamber 3200 generally does not contact the patient's face, it is positioned relatively close to the patient's face (e.g., in order to reduce unnecessary projections from the patient's face). The HME 6000 therefore, has a shape that at least partially complements the shape of the plenum chamber 3200. For example, the plenum chamber 3200 and the HME 6000 may each include the same curvature. The complementary shape not only permits the HME 6000 to be retrofitted into the plenum chamber 3200 (e.g., a plenum chamber 3200 not originally intended to be used with an HME 6000), but limits contact between the plenum chamber 3200 and the HME 6000 in order to avoid irritation to the patient and/or damage to the plenum chamber 3200.

5.7.1 Nose Ridge

In certain forms (see e.g., FIGS. 6A-8D), the HME 6000 is coupled to a ridge of the patient's nose, and along the outer surface of the patient's nose toward the patient's nasal ala. The HME 6000 supports an HME material 6002 below the patient's nares, so that the HME material 6002 intersects flow paths associated with the patient breathing through their nose.

As illustrated in FIG. 2D, the ridge of the patient's nose extends from the sellion to the pronasale. The HME 6000 may be coupled along any length of the ridge, but may preferably be coupled closer to the pronasale. Specifically, it may be undesirable for the HME 6000 to be coupled adjacent to the patient's nasal bone. This may cause the patient discomfort, and may also not allow the patient interface 3000 room to couple to the patient's face. In other words, if the HME 6000 is coupled to the patient's nose at the sellion, there would be nowhere on the patient's nose that the seal-forming structure 3100 could be positioned so that the HME 6000 was retained within the plenum chamber 3200. Thus, the HME 6000 may be positioned adjacent to the lateral nasal cartilage and/or to the greater alar cartilage. The HME 6000 may not be positioned completely on the pronasale (e.g., because the HME 6000 may slip off of the patient's nose), but may be positioned proximate to the pronasale in order to allow the seal-forming structure 3100 room to couple to the patient's nose.

5.7.1.1 Rectangular Cradle

As shown in FIGS. 6A-6C, one form of the HME 6000*a* includes a frame 6004 and a cradle 6006. The frame 6004 includes a first superior bar portion 6008 and a second superior bar portion 6010. The superior bar portions 6008, 6010 are angled with respect to one another, and come together at an apex A.

In one form, the superior bar portions 6008, 6010 are formed from a single piece of material (e.g., metal, plastic, etc.). The superior bar portions 6008, 6010 may come together at the apex A in a rounded or curved shape. The curve at the apex A may substantially correspond to a curvature along the ridge of a patient's nose. In some examples, the superior bar portions 6008, 6010 may be formed from a flexible or semi-ridged material so that the curvature at the apex may be adjusted in order to correspond to a variety of different nose sizes.

The frame 6004 also includes a first inferior bar portion 6012 and a second inferior bar portion 6014. The first inferior bar portion 6012 is connected to the first superior bar portion 6008, and the second inferior bar portion 6014 is connected to the second superior bar portion 6010. The inferior bar portions 6012, 6014 extend along either side (e.g., right side or left side) of the patient's nose, and may be anchored behind the nasal ala on the respective side of the patient's face.

In one form, the inferior bar portions 6012, 6014 are formed as a single piece with the respective superior bar portions 6008, 6010. The entire frame 6004 may therefore be formed from a single piece of material. A transition between the respective inferior bar portions 6012, 6014 and superior bar portions 6008, 6010 may be adjustable, allowing an angle of the transition to change. This may allow the frame 6004 to have a better fit for each individual patient, which may improve patient comfort, and therefore patient compliance.

The cradle 6006 includes a posterior bar portion 6016 and an anterior bar portion 6018. The posterior bar portion 6016 is positioned proximate to the patient's lip superior when the HME 6000*a* is worn by the patient. The anterior bar portion 6018 extends beyond the posterior bar portion 6016 in a direction away from the patient's face. In other words, the anterior bar portion 6018 is disposed more distal to the patient's lip superior than the posterior bar portion 6016. In the illustrated example, the anterior bar portion 6018 is integrally formed with the frame 6004 (e.g., the inferior bar portions 6012, 6014, superior bar portions 6008, 6010, and anterior bar portion 6016 are formed from a single piece of material). The posterior bar portion 6016 may be formed from a separate piece of material, and coupled to the frame 6004 (e.g., via welding, fastening, adhesive, etc.). In other examples, the posterior bar portion 6016 may be integrally formed with the frame 6004 and/or the anterior bar portion 6018 may be coupled to the frame 6004.

The posterior and anterior bar portions 6016, 6018 may extend along the patient's face, and create a breathing area BA that is substantially orthogonal with respect to the nares of the patient. In other words, the breathing area BA is substantially orthogonal with respect to the patient's lip superior, so that the breathing area BA extends in a direction away from the patient's lip superior.

In the illustrated example, the breathing area BA defines a generally rectangular shape. The breathing area BA may extend beyond the extent of the patient's nares, which enables a greater percentage of airflow into and out of the patient's nares pass through the breathing area BA (e.g., as compared to a breathing area BA that did not extend beyond the patient's nares). The rectangular shape of the breathing area BA may also assist in maximizing the total area.

While the breathing area BA generally defines a rectangular shape, the posterior bar portion 6016 may have a curved shape, so that at least one side of the breathing area is not straight. The curved shape of the posterior bar portion 6016 may correspond to a shape of the patient's lip superior. For example, the posterior bar portion 6016 may follow the contour of the patient's lip superior. This may provide a more comfortable fit for the patient (e.g., by reducing sharp edges). The curvature of the posterior bar portion 6016 may be slightly adjustable so that the posterior bar portion 6016 may better correspond to the contour of the lip superior. Adjusting the curvature of the posterior bar portion 6016 may also adjust the breathing area BA (e.g., adjusting the posterior bar portion 6016 to be more concave with respect to the patient's lip superior reduces the breathing area BA).

As shown in FIG. 6B, the HME material 6002 is coupled to the cradle 6006 of the HME 6000*a*. Specifically, the HME material 6002 is secured to the posterior and anterior bar portions 6016, 6018 in order to cover the breathing area BA. In other words, the HME material 6002 may be slightly larger than the breathing area BA. The HME material 6002 is coupled to the cradle 6006 in a generally taut configuration. For example, the HME material 6002 is stretched across the breathing area BA so that there is minimal sag in the HME material 6002.

In one form, the HME material 6002 is secured to the cradle 6006 during manufacturing of the HME 6000*a*. The HME material may be secured using an adhesive, or any other similar securing means. The patient may be unable to remove and replace the HME material 6002. Instead, the patient may have to replace the entire HME 6000*a*. Since the HME material 6002 is pre-attached in a taut position, the patient may not be able to make significant adjustments to the shape of the frame 6004 and or the shape of the cradle 6006 (e.g., because doing so may disrupt the connection between the HME material 6002 and the cradle). The HME 6000*a* may come in different sizes (e.g., small, medium, large) in order to correspond to patients with different sized noses.

In one form, the HME material 6002 may be separate from the cradle 6006, and may be applied by the patient. The HME material 6002 may be constructed to have an area larger than the breathing area BA. The patient may be able to make any necessary adjustments to the frame 6004 and/or to the cradle 6006 prior to coupling the HME material 6002 to the cradle. The patient may then attach the HME material, and if necessary, may trim any access material so that the shape of the HME material substantially mirrors the breathing area BA. An adhesive region 6020 may be included along an outer perimeter of the HME material 6002. The adhesive region 6020 may be used to secure the HME material 6002 to the cradle 6006. A patient may also be able to peel away the HME material 6002 in order to replace an old sheet of HME material 6002 with a new, clean sheet of HME material 6002. The frame 6004 and cradle 6006 may be reusable, and may not need to be discarded with the HME material 6002.

As shown in FIG. 6C, the HME 6000*a* is supported on the ridge of the patient's nose so that the HME material 6002 extends anterior to the patient's nose. Specifically, the frame 6004 may be positioned adjacent to the septum cartilage, in addition to the lateral nasal cartilage and/or to the greater alar cartilage. The frame 6004 may not be biased, and therefore may not substantially press against the patient's nose. This type of fit may improve patient compliance because the HME 6000a is not tight against the patient's nose and constricting the patient's airways. However, contact between the frame 6004 and the patient's nasal ridge may produce a frictional force that may help maintain the HME 6000a in the in use position. Additionally, the force of gravity may pull the frame 6004 into the patient's nasal ridge in certain sleeping orientations (e.g., on the patient's stomach) to provide further assistance in retaining the HME 6000a in the in use position.

When worn by the patient, the HME material 6002 extends more laterally than (e.g., to the right and left of) and more anterior than (e.g., in front of) the patient's nose. The HME material 6002 therefore substantially covers the patient's nares, so that inhaled and exhaled air is directed through the HME material 6002. By extending beyond the outer extents of the patient's nose, additional flow paths may intersect (i.e., pass through) the HME material 6002. Additionally, a larger breathing area BA may enable to HME material 6002 to hold more water vapor before becoming completely saturated.

5.7.1.2 Curved Cradle

FIGS. 7A-7C illustrate an HME 6000b that is a variation of the HME 6000a shown in FIGS. 6A-6C, and described above. Only some similarities and differences between the HME 6000a and the HME 6000b are described below.

The HME 6000b includes a frame 6004 and a cradle 6006. The frame is constructed from a first superior bar portion 6008, a second superior bar portion 6010, a first inferior bar portion 6012, and a second superior bar portion 6014. The superior bar portions 6008, 6010 and inferior bar portions 6012, 6014 are arranged in substantially the same manner as in the HME 6000a.

The cradle 6006 includes a posterior bar portion 6016 and an anterior bar portion 6018. In the illustrated example, the anterior bar portion 6018 is formed as a single piece with the frame 6004 (e.g., with the inferior bar portions 6012, 6014), and the posterior bar portion 6016 is coupled to the frame 6004 (e.g., via welding, fastening, adhesive, etc.). In other examples, the posterior bar portion 6016 may be integrally formed with the frame 6004 and/or the anterior bar portion 6018 may be coupled to the frame 6004.

As shown in FIG. 7B, the breathing area BA of the HME 6000b has a rounded shape (i.e., not rectangular). In the illustrated example, the posterior bar portion 6016 has substantially the same shape as the posterior bar portion 6016 of the HME 6000a (e.g., because the patient's lip superior has the same curvature). The anterior bar portion 6018 also is curved. The total breathing area BA formed between the posterior and anterior bar portions 6016, 6018 is less than the breathing area BA of the HME 6000a.

As shown in FIG. 7C, the cradle 6006 of the HME 6000b may extend beyond the patient's nose in the lateral and anterior directions. Inhaled and exhaled air still pass through the HME material 6002, but fewer flow paths may intersect with the HME material 6002. However, the curved shape of the cradle 6006 may provide a more low profile look to the HME 6000b, as compared to a rectangular cradle 6006. Specifically, the curved shape of the anterior bar portion 6018 may cause the cradle 6006 to sit closer to the patients face (e.g., not extend as far from the patient's face). This may limit the amount of the cradle 6006 within the patient's line of sight, which may reduce any obstructions caused by wearing the HME 6000b. Specifically, this may increase patient compliance if the HME is less obtrusive (e.g., has a low profile) while being worn.

The HME 6000b is supported on the ridge (e.g., in a similar manner to that of the HME 6000a) of the patient's nose so that the HME material 6002 extends anterior to the patient's nose. The frame 6004 may not be biased, and therefore may not substantially press against the patient's nose. This type of fit may further improve patient compliance because the HME 6000b is not tight against the patient's nose and constricting the patient's airways. However, contact between the frame 6004 and the patient's nasal ridge may produce a frictional force that may help maintain the HME 6000b in the in use position. Additionally, the force of gravity may pull the frame 6004 into the patient's nasal ridge in certain sleeping orientations (e.g., on the patient's stomach) to provide further assistance in retaining the HME 6000b in the in use position.

5.7.1.3 Curved Cradle with Support

FIGS. 8A-8D illustrate an HME 6000c that is a variation of the HME 6000a shown in FIGS. 6A-6C, and the HME 6000b shown in FIGS. 7A-7C. Only some similarities and differences between the HME 6000a, 6000b and the HME 6000c are described below.

The cradle 6006 of the HME 6000c includes a posterior bar portion 6016 and an anterior bar portion 6018. In the illustrated example, the anterior bar portion 6018 is formed as a single piece with the frame 6004 (e.g., with the inferior bar portions 6012, 6014), and the posterior bar portion 6016 is coupled to the frame 6004 (e.g., via welding, fastening, adhesive, etc.). In other examples, the posterior bar portion 6016 may be integrally formed with the frame 6004 and/or the anterior bar portion 6018 may be coupled to the frame 6004.

In the illustrated example, the posterior bar portion 6016 and the anterior bar portion 6018 are coupled to the frame 6004 on different planes. In other words, the posterior bar portion 6016 is inferior to the anterior bar portion 6018 when the HME is worn by the patient (see e.g., FIG. 8D). Therefore, the posterior and anterior bar portions 6016, 6018 define a breathing volume BV instead of a breathing area BA. For example, the curvature of the anterior bar portion 6018 at least partially forms a face of the breathing volume BV, and the posterior bar portion 6016 at least partially forms a depth of the breathing volume BV.

The HME material 6002 is coupled to the cradle 6006 of the HME 6000c. Specifically, the HME material 6002 is secured to the posterior and anterior bar portions 6016, 6018. In other words, the HME material 6002 is positioned within the breathing volume BV, but does not fill the entire breathing volume BV. Rather, the HME material 6002 extends in a superior/inferior direction, as well as in a posterior/anterior direction (e.g., diagonally) in order to contact both the posterior and anterior bar portions 6016, 6018.

The HME material 6002 is coupled to the cradle 6006 in a generally taut configuration. For example, the HME material 6002 is stretched through the breathing area BV so that there is minimal sag in the HME material 6002. However, since the length of the HME material 6002 is longer (e.g., as compared to a length used with the HME 6000a or 6000b), the HME material 6002 used with the HME 6000c may experience some sag.

A support bar 6022 extends between the posterior bar portion 6016 and the anterior bar portion 6018. The support bar 6022 may separate from and coupled to the posterior and anterior bar portions 6016, 6018 (e.g., via welding, fastening, adhesive, etc.). In the illustrated example, the support bar includes a straight section 6022a and a curved section 6022b, which may be constructed as a single piece. The straight section 6022a extends from the posterior bar portion 6016, and may be generally orthogonal with respect to the posterior bar portion 6016 (e.g., the straight section 6022a extends only in the posterior/anterior direction). The curved section 6022b spans the depth of the breathing volume BV, and may connect to the anterior bar portion 6018 generally orthogonally to the straight section 6022a and to the anterior bar portion 6018.

The HME material 6002 is also coupled to the support bar 6022. The HME material 6002 adapts a curvature of the breathing volume BV (e.g., via the support bar 6022). For example, the HME material 6002 does not extend linearly between the posterior and anterior bar portions 6016, 6018. Instead, the HME material curves through three-dimensional space (e.g., parabolically).

As shown in FIG. 8A, a single sheet of the HME material 6002 is coupled to the cradle 6006. In the illustrated example, the HME material 6002 is coupled to the cradle 6006 using an adhesive region 6020 (e.g., by the patient, by a clinician, etc.), although patient and/or clinician may receive the HME 6000c with the HME material 6002 pre-assembled. The HME material 6002 may be coupled to the HME 6000c by using the support bar 6022 as a guide (e.g., to establish placement, curvature, etc.). The HME material 6002 may also include a central adhesive section (not shown), or the patient/clinician may apply an adhesive (e.g., glue) to the HME material 6002 in order to couple the HME material to the support bar 6022. This may limit a central section of the HME material 6002 (e.g., proximate to the support bar 6022) from moving away from the support bar 6022 and out of its assembled position (e.g., when the patient inhales).

As shown in FIG. 8B, multiple sheets of HME material 6002 may be coupled to the cradle 6006. The illustrated example shows a pair of sheets, although any number may be used. Each sheet of HME material 6002 extends from one lateral side (e.g., left or right) of the cradle 6006 to the support bar 6022. In other words, both sheets of the HME material 6002 are coupled to the support bar 6022. In this configuration, the area of each sheet of HME material 6002 is less than both the single sheet used in FIG. 8A, as well as the single sheet used in with the HMEs 6000a and 6000b. Utilizing a smaller piece of HME material 6002 may allow the sheet to be under more tension while coupled to the cradle 6006.

As shown in FIG. 8C, the HME material 6002 curves through the breathing volume BV. The HME material 6002 is positioned on the outer face of the breathing volume BV. In other words, the total volume of the breathing volume BV does not substantially change when the HME material 6002 is coupled to the cradle 6006. Additionally, the HME material 6002 has substantially the same shape while coupled to the cradle 6006, regardless of the number of sheets used.

As shown in FIG. 8D, the HME 6000c is coupled to the patient's nose (e.g., in a similar location to the HMEs 6000a, 6000b) so that at least some of the patient's nose sits within the breathing volume BV. For example, while the patient is wearing the HME 6000c, the lip superior and the subnasale are positioned within the breathing volume BV. Additionally, an upper surface of the anterior bar portion 6018 may be more superior to a portion of the patient's nares. This helps reduce airflow that enters or exits the patient's nose without passing through the HME material 6002 (e.g., by traveling alongside the patient's nose). For example, the HME 6000c more completely surrounds the patient's nose (e.g., as compared to the HMEs 6000a, 6000b), so that a greater percentage of exhaled moisture may be captured and reintroduced into the system.

The support bar 6022 is curved in order to substantially correspond to the subnasale of the patient. In other words, the curvature of the curved section 6022b includes a curvature similar to the subnasale. The support bar 6022 is spaced apart from the subnasale so that the support bar does not contact the patient's nose. In this way, the HME material 6002 is spaced apart from the patient's nose and does not create unnecessary impedance on the patient breathing.

The HME 6000c is supported on the ridge (e.g., in a similar manner to that of the HME 6000a and/or HME 6000b) of the patient's nose so that the HME material 6002 extends anterior to the patient's nose. The frame 6004 may not be biased, and therefore may not substantially press against the patient's nose. This type of fit may further improve patient compliance because the HME 6000c is not tight against the patient's nose and constricting the patient's airways. However, contact between the frame 6004 and the patient's nasal ridge may produce a frictional force that may help maintain the HME 6000c in the in use position. Additionally, the force of gravity may pull the frame 6004 into the patient's nasal ridge in certain sleeping orientations (e.g., on the patient's stomach) to provide further assistance in retaining the HME 6000c in the in use position.

5.7.2 Side of Nose

In certain forms (see e.g., FIGS. 9A-11E), the HME 6000 is coupled along the sides of the patient's nose. The HME 6000 includes arms biased inwardly, which press against an outer surface of the patient's nose. The biasing force is sufficient to maintain the position of the HME 6000 relative to the patient's nose. The HME 6000 supports an HME material 6002 below the patient's nares, so that the HME material 6002 intersects flow paths associated with the patient breathing through their nose.

5.7.2.1 Adjustable Nose Ridge

As shown in FIGS. 9A-9C, an HME 6000d includes a frame 6004 and a cradle 6006. The frame 6004 includes a first arm 6024 and a second arm 6026. Each arm 6024, 6026 is adapted to contact a respective lateral side (e.g., left or right side) of the patient's nose.

In the illustrated example, the first and second arms 6024, 6026 are constructed from a single piece of material. The first and second arms 6024, 6026 are angled with respect to one another, and come together at narrow end in the form of a loop 6028 (e.g., the loop 6028 is formed proximate to the narrowest point between the arms 6024, 6026). An angle between the arms 6024, 6026 may substantially correspond to an angle of a patient's nose.

The frame 6004 may be constructed from a rigid or semi-rigid material (e.g., metal, plastic, etc.), and may allow flexion between the arms 6024, 6026. For example, the arms 6024, 6026 may be able to pivot apart and increase the angle between them. As shown in FIGS. 9A and 9B, the HME 6000d may include a first position, with an angle $W_1$ between the arms 6024, 6026, and a second position, with an angle $W_2$ between the arms 6024, 6026. The first position (see e.g., FIG. 9A) may be a relaxed position, while the second position (see e.g., FIG. 9B) may be an extended position. The angle $W_2$ may be greater than the angle of $W_1$.

The cradle 6006 includes a pair of lateral arm portions 6030 and an anterior arm portion 6032. In the illustrated example, the arm portions 6030, 6032 of the cradle 6006 are formed from a single piece of material. Additionally, the cradle 6006 and the frame 6004 may be formed from a single piece of material. Thus, the HME 6000*d* may include a single continuous loop of material. Although in other examples, the cradle 6006 and the frame 6004 may be separate and coupled together (e.g., via welding, fastening, adhesive, etc.).

A transition between the first and second arms 6024, 6026 and the respective lateral arm portion 6030 may be curved (e.g., convex relative to the patient) around an axis orthogonal with respect to the anterior arm portion 6032. The lateral arm portions 6030 are on a lower plane than the first and second arms 6024, 6026.

In the illustrated example, each of the lateral arm portions 6030 includes a first or posterior section 6030*a* and a second or anterior section 6030*b*. The posterior section 6030*a* extends directly from the respective transition toward the anterior arm portion 6032. The posterior sections 6030*a* may have a slight curvature, and may also extend in a superior direction (e.g., the posterior sections 6030*a* curve upwardly from first and second arms 6024, 6026 toward the anterior arm portion 6032. The anterior sections 6030*b* extend from an end of a respective posterior section 6030*a*, and connect to the anterior arm portion 6032. The anterior sections 6030*b* do not include a curvature, and extend generally horizontally (e.g., when worn by the patient). The anterior sections 6030*b*, as well as the anterior arm portion 6032 are more superior to the posterior sections 6030*a* (e.g., when worn by the patient).

Since the frame 6004 and the cradle 6006 may be formed as a single piece, the first and second arms 6024, 6026 may be limited by the cradle 6006 in an amount that they are capable of flexing. In other words, the first and second arms 6024, 6026 do not have a free end, and are therefore limited in the amount that they can flex at least in part by the cradle 6006. Constraining the ability of the first and second arms 6024, 6026 to move limits a difference between the first and second angles $W_1$ and $W_2$. The HME 6000*d* may include different sizes (e.g., small medium, large) in order to allow the HME 6000*d* to be positioned on different sized noses. By limiting the degree of adjustment for the individual HME 6000*d*, a patient may be able to more easily determine that a proper size for their specific nose. For example, if there angular adjustment is not sufficient on one sized HME 6000*d*, the patient may be alerted to choose a different size in order to achieve a sufficiently proper fit.

Returning to FIG. 9A, the cradle 6006 does not define a specific breathing area, as the HMEs 6000*a*-6000*c* did. In other words, the HME 6000*d* lacks a posterior bar, so there is no obstruction between the patient's lip superior and the anterior arm portion 6032. This may improve the comfort for a patient because a section of the cradle 6006 is not adjacent to, or in contact with, the patient's lip superior. Removing a posterior bar may improve patient compliance doing so reduces patient irritation.

The HME material 6002 is coupled to the cradle 6006 in any of the manners described above. Since there is no posterior bar, the HME material 6002 is supported by the cradle 6006 on only three sides. In other words, the HME material 6002 is unsupported proximate to the patient (see e.g., FIG. 9C). In the illustrated example, the HME material 6002 is supported by the anterior arm portion 6032 and the anterior sections 6030*b*. However, the HME material 6002 may also extend along the posterior sections 6030*a*.

As shown in FIG. 9C, the HME 6000*d* is coupled to an outer surface of the patient's nose. The patient may move the first and second arms 6024, 6026 for the relaxed position to the extended position in order to space the arms apart a sufficient distance to fit around the patient's nose. As described above, the difference between the relaxed and extended positions may be minimal (e.g., limited angular displacement). As the first and second arms 6024, 6026 move toward the extended position, the loop 6028 may represent the pivot point for the arms 6024, 6026. Once the HME 6000*d* is positioned around the patient's nose, the first and second arms 6024, 6026 attempt to return to their relaxed state. The loop 6028 may assist in providing the biasing force needed to return the frame 6004 to the relaxed state. The arms 6024, 6026 press against an outer surface of the patient's nose in order to affix the HME 6000*d* thereon. The gripping force caused by the arms 6024, 6026 pressing against the patient's nose may limit the frame 6004 from slipping along the patient's nose (e.g., as a result of the gravitational force). Additionally, contact between the frame 6004 and the patient's nasal ridge may produce a frictional force that may help maintain the HME 6000*d* in the in use position. The force of gravity may pull the frame 6004 into the patient's nasal ridge in certain sleeping orientations (e.g., on the patient's stomach) to provide further assistance in retaining the HME 6000*d* in the in use position. In this position, the loop 6028 is spaced apart from at least a portion of the ridge of the patient's nose. For example, the loop 6028 may be spaced apart from the septum cartilage, but the arms 6024, 6026 may still be positioned adjacent to the lateral cartilage and/or the greater alar cartilage.

The curved portion of the transition between the frame 6004 and the cradle 6006 may curve behind the nasal ala on either side of the patient's nose. The transition may hook around the respective nasal ala, and may provide a secondary point of attachment to the patient's nose.

The HME material 6002 is supported in front of and below the patient's nose. The anterior sections 6030*b* are raised from the posterior sections 6030*a* in order to bring the HME material 6002 closer to the patient's nares (e.g., in order to capture a greater percentage of water vapor). The lateral arm portions 6030 are also wider than the patient's nose in order to assist in limiting exhaled air from escaping around edges of the HME material 6002.

5.7.2.2 Long Arms

FIGS. 10A-10E illustrate an HME 6000*e* that is a variation of the HME 6000*d* shown in FIGS. 9A-9C, and described above. Only some similarities and differences between the HME 6000*d* and the HME 6000*e* are described below.

The HME 6000*e* includes a frame 6004 and a cradle 6006. The frame 6004 is constructed from a first arm 6024 and a second arm 6026. The arms 6024, 6026 are formed from separate pieces of material, and do not connect to one another. Each arm 6024, 6026 may be movable independently of the other arm 6024, 6026. The arms 6024, 6026 may also be angled with respect to one another. In the illustrated example, the angle between the arms 6024, 6026 in a relaxed position is substantially the same as the angle $W_1$. A distance $T_1$ between the arms 6024, 6026 may be a minimum while the arms 6024, 6026 are in the relaxed position.

The frame 6004 also includes a first connector arm 6034 and a second connector arm 6036. Each connector arm 6034, 6036 is formed as a single piece with the respective arm 6024, 6026. While the first and second arms 6024, 6026 are substantially linear, the connector arms 6034, 6036 are curved. In the illustrated example, the connector arms 6034, 6036 are curved in a concave upward direction about an axis generally parallel to the patient's lip superior (see e.g., FIGS. 10D and 10E). The first and second arms 6024, 6026 are movable relative to one another about the respective connector arm 6034, 6036. In other words, a pivot point for each arm 6024, 6026 is on the respective connector arm 6034, 6036.

Returning to FIG. 10A, the connector arms 6034, 6036 are coupled to the cradle 6006 in order to couple the frame 6004 to the cradle 6006. The frame 6004 and cradle 6006 may be separate pieces and may be connected together (e.g., via welding, fastening, adhesive, etc.), although the frame 6004 and the cradle 6006 may be a single piece. The cradle 6006 includes a complementary curve to each of the connector arms 6034, 6036. In other words, the cradle curves around the same axis as the connector arms 6034, 6036, and with substantially the same radius of curvature.

The cradle 6006 has a generally rectangular shape with a posterior arm 6038 and an anterior arm 6040. The posterior and anterior arms 6038, 6040 are generally parallel to one another, and generally linear (e.g., not curved). A pair of outer support arms 6042 extend between the posterior and anterior arms 6038, 6040 and form the breathing area BA for the HME 6000e. A central support arm 6044 is disposed between the pair of support arms 6042, and also extends between the posterior and anterior arms 6038, 6040.

The HME material 6002 is coupled to the cradle 6006 and substantially covers the breathing area BA. The HME material 6002 is positioned on the cradle 6006 in order to curve with substantially the same curvature as the support arms 6042, 6044. A single sheet of HME material 6002 (see e.g., FIG. 10A) or multiple sheets of HME material (see e.g., FIG. 10B) may be coupled to the cradle 6006. In either case, the central support arm 6044 assists in supporting the sheet(s) of HME material 6002.

As shown in FIG. 10C, the first and second arms 6024, 6026 may move relative to one another. The arms 6024, 6026 may have greater freedom of movement than the arms 6024, 6026 of the HME 6000d because each includes a free end. As the arms 6024, 6026 move relative to one another, the narrowest distance between the arms 6024, 6026 widens to a distance $T_2$, which is greater than $T_1$. In the extended position, the distance $T_2$ may allow the patient to position the HME 6000e around their nose. Once the HME 6000e is positioned in a desired location, the patient may release the arms 6024, 6026 so that they return to their relaxed position, and press against an outer surface of the patient's nose. The gripping force caused by the arms 6024, 6026 pressing against the patient's nose may limit the frame 6004 from slipping along the patient's nose (e.g., as a result of the gravitational force). Additionally, contact between the frame 6004 and the patient's nasal ridge may produce a frictional force that may help maintain the HME 6000e in the in use position. The force of gravity may pull the frame 6004 into the patient's nasal ridge in certain sleeping orientations (e.g., on the patient's stomach) to provide further assistance in retaining the HME 6000e in the in use position.

As shown in FIGS. 10D and 10E, when the HME 6000e is coupled to the patient's nose, the cradle 6006 curves away from the patient's nose so that the anterior arm 6040 extends beyond the tip of the patient's nose. Extending beyond the patient's nose, and curving in the superior direction, may assist in capturing a greater percentage of water vapor in the exhaled gas. The pair of outer support arms 6042 may also extend beyond the outer edges of the patient's nose to further assist in limiting the amount of water vapor that escapes to the side of the HME 6000e.

5.7.2.3 Short Arms

FIGS. 11A-11E illustrate an HME 6000f that is a variation of the HMEs 6000d and 6000e described above. Only some similarities and differences between the HMEs 6000d, 6000e and the HME 6000f are described below.

The HME 6000f includes a frame 6004 and a cradle 6006. The frame 6004 is constructed from a first arm 6024 and a second arm 6026. The arms 6024, 6026 are formed from a single piece of material, and connect to one another along a posterior arm 6046. Each arm 6024, 6026 may be movable independently of the other arm 6024, 6026. The arms 6024, 6026 may also be angled with respect to one another. In the illustrated example, the angle between the arms 6024, 6026 in a relaxed position is substantially the same as the angle $W_1$. A distance $D_1$ between the arms 6024, 6026 may be a minimum while the arms 6024, 6026 are in the relaxed position.

The arms 6024, 6026 of the HME 6000f are shorter than the corresponding arms of the HME 6000e. Therefore, the arms 6024, 6026 of the HME 6000f do no extend as far along the patient's nose. This may be more comfortable to a patient, because the frame 6004 contacts less of the patient's nose.

In the illustrated example, the arms 6024, 6026 of the HME 6000f are thicker than the arms 6024, 6026 of the HME 6000e. This may limit the amount that they are able to bend. For example, the thicker piece of material forming the arms 6024, 6026 of the HME 6000f may provide more resistance to moving either of the arms 6024, 6026.

The cradle 6006 includes a pair of outer support arms 6042 connected to the posterior arm 6046. The cradle 6006 also includes a central support arm 6044 that is disposed between, and is generally parallel to, the outer support arms 6042. An anterior arm 6040 is coupled to each of the support arms 6042, 6044. In the illustrated example, the support arms 6042, 6044 and the anterior arm 6040 are formed as a single piece, although in other examples, they may be formed as multiple pieces.

The HME material 6002 is coupled to the cradle 6006 and substantially covers the breathing area BA (e.g., defined between the posterior arm 6046, the support arms 6042, and the anterior arm 6040). The HME material 6002 is positioned on the cradle 6006 in order to curve with substantially the same curvature as the support arms 6042, 6044. A single sheet of HME material 6002 (see e.g., FIG. 11A) or multiple sheets of HME material (see e.g., FIG. 11B) may be coupled to the cradle 6006. In either case, the central support arm 6044 assists in supporting the sheet(s) of HME material 6002.

As shown in FIG. 11C, the arms 6024, 6026 are flexed outwardly into an extended position, and are spaced apart by a distance $D_2$, which is greater than $D_1$. Each arm 6024, 6026 may be independently pivotable relative to the posterior arm 6046. The greater thickness of the arms 6024, 6026 (e.g., as compared to the thickness of the arms 6024, 6026 of the HME 6000e) may minimize the difference between $D_2$ and $D_1$.

As shown in FIGS. 11D and 11E, when the HME 6000f is coupled to the patient's nose, the cradle 6006 curves around from the patient's nose in a lateral direction (e.g., right to left). In other words, the cradle 6006 curves between the outer support arms 6042 about an axis orthogonal with respect to the patient's lip superior. The support arms 6042, and therefore the HME material 6002, extends wider (e.g., further left and right) of the patient's nares. Additionally, since the arms 6024, 6026 are shorter (e.g., as compared to the HME 6000e), the cradle 6006 and the HME material 6002 sit closer to the patient's nares. Extending laterally to the side of the patient's nose, and being positioned closer to the patient's nose, may assist in capturing a greater percentage of water vapor in the exhaled gas. For example, the positioning of the HME material 6002 on the cradle 6006 may assist in limiting the amount of gas that passes around the HME material 6002, and not through the HME material 6002. Positioning the HME material 6002 may increase the impedance (e.g., and also the collection of water vapor), but may not substantially negatively affect breathing.

Similar to the arms 6024, 6026 in the HME 6000e (see e.g., FIGS. 10D and 10E), the arms 6024, 6026 in the HME 6000f may provide a gripping force against the patient's nose. The gripping force caused by the arms 6024, 6026 pressing against the patient's nose may limit the frame 6004 from slipping along the patient's nose (e.g., as a result of the gravitational force). Additionally, contact between the frame 6004 and the patient's nasal ridge may produce a frictional force that may help maintain the HME 6000f in the in use position. The force of gravity may pull the frame 6004 into the patient's nasal ridge in certain sleeping orientations (e.g., on the patient's stomach) to provide further assistance in retaining the HME 6000f in the in use position.

5.7.3 Within the Nose

In certain forms (see e.g., FIGS. 12A-14D), the HME 6000 is coupled to the patient's nose within the patient's nares (e.g., against the patient's septum). The HME 6000 includes arms biased inwardly, which press against a surface within the patient's nose. The biasing force is sufficient to maintain the position of the HME 6000 relative to the patient's nose. The HME 6000 supports an HME material 6002 below the patient's nares, so that the HME material 6002 intersects flow paths associated with the patient breathing through their nose. In order to maintain a low profile, the HME 6000 may also be positioned proximate to, or in contact with, the patient's subnasale and/or columella. Specifically, the HME 6000 may include a curvature and/or contour that approximates the shape of the subnasale and/or columella so that the patient experiences little to no irritation from wearing the HME 6000 (e.g., no jagged edges that could disrupt the patient's skin). The HME 6000 can then be as close as possible to the patient's nose, so as not to project out and interfere with the plenum chamber 3200.

5.7.3.1 Ring Cradle

As shown in FIGS. 12A-12E, an HME 6000g includes a frame 6004 and a cradle 6006. In the illustrated example, the frame 6004 and the cradle 6006 are formed as separate pieces and are coupled together (e.g., via welding, fastening, adhesive, etc.). The frame 6004 and the cradle 6006 may not be movable with respect to one another.

In the illustrated example, the frame 6004 is shaped like a partial ring, and is curved between a first free end 6048 and a second free end 6050. In other words, the frame 6004 is shaped like a three-dimensional annulus sector (i.e., not a complete annulus). The frame 6004 may be formed as a single piece of material (e.g., metal, plastic, etc.). The material may be semi-rigid or flexible in order to allow some flexion between the first and second free ends 6048, 6050.

The frame 6004 includes an inferior portion 6052 that connects the free ends 6048, 6050 together. A curvature of the inferior portion 6052 is relatively small. In other words, the inferior portion 6052 may be generally straight, and includes only a minimal curvature. The curvature of the inferior portion 6052 may be similar to a curvature of a patient's columella. In other words, the curvature of the inferior portion 6052 may provide a smooth transition so as to avoid providing undue pressure on the patient's columella.

An S-shaped portion 6054 extends from the inferior portion 6052 toward the respective free end 6048, 6050. The S-shaped portions 6054 include both a concave and a convex portion in order to define the s-shape. The S-shaped portions 6054 may mirror each other, and the curvature of the S-shaped portions 6054 may be substantially greater than the curvature of the inferior portion 6052. In other words, the S-shaped portions 6054 may have a substantially sharper curved, and may form a greater proportion of a total circular area than the inferior portion 6052. Each of the S-shaped portions 6054 includes a seating surface 6056 on a convex portion (e.g., a negative curvature with respect to the patient's septum, in use). In other words, a surface generally tangent to the respective S-shaped portion 6054 is disposed proximate to a center of the frame 6004. The seating surfaces 6056 may also be proximate to the respective free ends 6048, 6050.

The cradle 6006 may include a first ring 6058 and a second ring 6060. Each ring 6058, 6060 is coupled to the inferior portion 6052 proximate a transition between the inferior portion 6052 and a respective S-shaped portion 6054. In the illustrated example, the first and second rings 6058, 6060 are generally circular in shape, although in other examples, the first and second rings 6058, 6060 may be other shapes (e.g., elliptical, oblong, etc.). The first ring 6058 is spaced apart from the second ring 6060. The first and second rings 6058, 6060 may also have the same diameter.

As shown in FIG. 12A, HME material 6002 is coupled to each of the first and second rings 6058, 6060. A separate sheet of HME material 6002 may be used for each of the first and second rings 6058, 6060. These sheets may be circular in shape, or may be another shape and trimmed to substantially match the shape of the respective ring 6058, 6060. The sheets of HME material 6002 may be coupled to each respective ring 6058, 6060 using an adhesive (e.g., glue, an adhesive section on the sheet, etc.), or any other appropriate method. In the illustrated example, the HME material 6002 is disposed proximate a superior region of each ring 6058, 6060. In other words, the HME material 6002 is disposed proximate to the patient's nares when the HME 6000g is worn. In other examples, the HME material 6002 may be positioned within the ring 6058, 6060 (e.g., HME material 6002 may fill the entire thickness of each ring 6058, 6060), or on an inferior section of the ring 6058, 6060. In still other examples, the HME material 6002 may be coupled to the superior and the inferior sections of the rings 6058, 6060 but may not be included through the center of each ring 6058, 6060.

In some forms, the HME material 6002 may be disposable after one or more uses. For example, the patient may be able to peel the HME material 6002 off of the respective ring 6058, 6060 and apply a new, clean piece of HME material 6002 with new adhesive. In other forms, the HME material 6002 may be removable from the rings 6058, 6060 and reusable after being cleaned. In still other forms, the HME material 6002 may be permanently coupled to the rings 6058, 6060.

As shown in FIGS. 12B and 12C, a plug 6062 constructed from HME material is inserted into each of the rings 6058, 6060. Each plug 6062 may be constructed from a resilient material so that it is capable of being compressed and then returning to its initial shape.

In the illustrated example, the plug 6062 includes a first end 6064 that has a first diameter and a second end 6066 that has a second diameter smaller than the first diameter. For example, the plug 6062 may be conical or frustoconical. The first diameter may be slightly wider than the diameter of the each ring 6058, 6060. This may prevent the plug 6062 from sliding completely through the respective ring 6058, 6060 when inserted.

In other forms, the plug 6062 may include a first end 6064 and a second end 6066 each with the first diameter. For example, the plug 6062 may be cylindrical. The first diameter may be slightly wider than the diameter of the each ring 6058, 6060. This may prevent the plug 6062 from sliding completely through the respective ring 6058, 6060 when inserted.

As shown in FIG. 12C, a holder 6068 may be used to hold the plugs 6062. The holder 6068 includes a pair of compartments 6070, each sized to substantially correspond to the shape of the plugs 6062. In other words, each of the compartments 6070 also has a larger diameter and a smaller diameter. In the illustrated example, each compartment 6070 is constructed from a plurality of spaced apart rings or circles. The rings are generally concentric with one another, and have progressively decreasing diameters. The compartments 6070 may also have openings on either end. One opening is wide enough in order to receive at least the first end 6064 of the plug 6062. The opposite end has a diameter that is smaller than the second diameter on the second end 6066, so that the plug 6062 may be unable to enter and/or exit the compartment through that end.

The compartments 6070 are coupled together with a linking member 6072. The linking member 6072 may be formed from a flexible material (e.g., flexible plastic, flexible metal, etc.), and may be capable of bending or deforming in order to change a position of one compartment 6070 with respect to the other compartment 6070. For example, the linking member 6072 may allow the compartments 6070 to increase their spacing with respect to one another in order to be inserted into the rings 6058, 6060 (see e.g., FIG. 12B).

In some forms, the linking member 6072 may not be resilient. For example, the linking member 6072 may retain its shape after the patient applies a bending force.

The plugs 6062 may be inserted into the respective compartment 6070 before the holder 6068 is inserted into the cradle 6006, or the plugs 6062 may be inserted after the holder 6068 has been inserted into the cradle 6006. As described above, the plugs 6062 may be constructed from a resilient material. The patient may compress each plug 6062 so that it fits within the smaller sized holder 6068. After releasing the force, each plug 6062 may expand to completely fill the compartment 6070. This may help to ensure that air does not enter the compartment 6070 without also entering the respective plug 6062.

In examples where the plug 6062 is cylindrical, the patient may manipulate (e.g., compress) each plug 6062 so that the second end 6066 has approximately the second diameter (e.g., so the plug 6062 temporarily has a conical or frustoconical shape). This may allow the plug 6062 to be positioned within the compartment 6070. Once the patient releases the force, the plug 6062 may expand toward its initial position until it contacts the side of the compartment. While in use, the cylindrical plug 6062 may appear the same as the conical or frustoconical plug 6062.

In some forms, the plugs 6062 may be inserted into the respective compartment 6070 without the need for additional coupling mechanisms. For example, an adhesive may not be needed to position each plug 6062 within the compartment 6070 (although an adhesive may be used). Instead, the plugs 6062 may be retained within the compartment 6070 by the force of friction. The expansion of the plugs 6062 within each compartment 6070 may create a frictional engagement that retains the plugs 6062 in place. After one or more uses, the patient may remove the plugs 6062 and either replace the used plugs 6062 with new plugs, or clean the plugs 6062 and reinsert them into the compartment 6070.

Once the holder 6068 has been inserted, the linking member 6072 traverses the distance between the rings 6058, 6060 (e.g., a similar distance as the inferior portion 6052). The non-resilient material of the linking member 6072 may make adjusting and inserting the holder 6068 into the compartments 6070 easier. The plugs 6062 are positioned within the holder 6068 so that the first ends 6064 of the plugs 6062 are positioned proximate to the patient's nares when the HME 6000g is worn. The plugs 6062 may be retained within the holder 6068 as a result of the force of gravity. For example, the force of gravity may pull the linking member 6072 into the rings 6058, 6060. The solid rings 6058, 6060 limit further movement in the inferior direction, thereby retaining the holder 6068 (and plugs 6062) in the desired position.

In other examples, the plugs 6062 may be positioned within the respective rings 6058, 6060 without using the holder 6068, and/or the plugs (and holder) may be inserted into the rings 6058, 6060 so that the first ends 6064 are positioned proximate to the patient's nares.

As shown in FIGS. 12D and 12E, the frame 6004 is inserted into the patient's nose, so that one S-shaped portion 6054 is positioned in one of the patient's nares. The inferior portion 6052 is positioned outside of the patient's nares and proximate to the patient's columella. In some examples, the inferior portion 6052 may be spaced apart from the columella in order to decrease irritation. In some examples, the inferior portion 6052 may contact the columella, and the slight curvature of the inferior portion 6052 may reduce irritation associated with the frame 6004 contacting the patient's nose. The curvature of the inferior portion 6052 may be slightly adjustable in order to better match the shape of each patient's columella. In any case, the curvature of the inferior portion 6052 may allow the S-shaped portions 6054 to be positioned deeper into the patient's nares (e.g., in order to provide a more secure connection), without causing significantly more discomfort to the patient.

The seating surface 6056 of each respective S-shaped portion 6054 contacts the patient's septum while the HME 6000g is coupled to the patient's nose. The frame 6004 may be flexible and the S-shaped portions 6054 may be able to bend relative to the inferior portion 6052. Specifically, the S-shaped portions 6054 may bend away from one another in order to create a greater distance between the seating surfaces 6056. This may assist the frame 6004 in fitting around the patient's septum. Once the S-shaped portion 6054 is in position (e.g., inside the respective nostril), the frame 6004 may bias toward a relaxed position so that the seating surfaces 6056 are brought into contact with the patient's septum and retained with the inward bias of the frame 6004.

The seating surfaces 6056 may grip the patient's septum to provide a frictional force that opposes the force of gravity. In other words, gravity may pull the HME 6000g in the inferior direction, and the frictional force caused by the seating surfaces 6056 gripping the septum may retain the HME 6000g in the in use position. When the patient is sleeping, his specific sleeping position may affect the total frictional force needed to retain the HME 6000g in position. For example, when the patient is sleeping on his back, the gravitational force is directed into the patient's face and is helping to retain the HME 6000g in position (e.g., even without considering the effects of friction). Alternatively, the force of gravity is directed away from a patient who sleeps on his stomach. Therefore, the frictional force would oppose the gravitational force and keep the HME 6000g properly positioned. Because gravity assists in maintaining the HME 6000g in the in use position for a back-sleeping patient, some patients may find that position to be more comfortable. However, the light weight of the HME 6000g may not require a substantial frictional force to oppose the force of gravity, so the patient may be able to comfortably wear the HME 6000g while in a different sleeping position.

Once the HME 6000g is coupled to the patient's nose, the rings 6058, 6060 are disposed proximate to the patient's nose. The HME material 6002 is also positioned proximate to the patient's nose. The rings 6058, 6060 are disposed inferior to the patient's nares, and may be substantially aligned with openings to the patient's nares. In this position, the rings 6058, 6060 may not extend substantially beyond the patient's nares in any direction, and the cradle 6006 may not curve around the patient's nose. While this may limit an amount of water vapor collected (e.g., as compared to the previous embodiments), the HME 6000g has a substantially low profile design, which does not extend substantially beyond the patient's nose. Specifically, using only sheets of HME material 6002 with the rings 6058, 6060 may create a low profile because there is substantially no protrusion in either the toward or away from the patient's nares. This may assist in improving patient compliance because the patient may less uncomfortable when a wearable device is smaller and contacts less of the patient's nose.

Additionally the free ends 6048, 6050 may not extend much beyond the respective S-shaped portion 6054. In other words, the free ends 6048, 6050 may not extend substantially across the patient's naris. This may assist in limiting the impedance caused by the frame 6004 (e.g., because there may not be an obstruction in the patient's airway). Additionally, this may improve patient comfort because only a single inner surface of each naris may be contacted by the frame 6004 (e.g., as opposed to both).

As shown in FIG. 12E, the frame 6004 is inserted into the patient's nose so that the plugs 6062 are not positioning within the patient's nares. The plugs 6062 and the holder 6068 may extend away from the patient's nose while in use (e.g., in the anterior and/or inferior direction). The surface area of HME material 6002 facing the patient's nose may be substantially the same in either FIG. 12D or 12E (e.g., regardless of whether the plugs 6062 are being used). In other words, the air that the patient exhales may be directed into the same sized surface of HME material 6002 whether or not the plugs 6062 are used. The plugs 6062 may provide a greater surface area below the frame 6004 as compared to the frame in FIG. 12D without the plugs 6062. The spaces between the concentric circles making up compartments 6070 assist in limiting the impedance caused by the holder 6068. In other words, the spaces provide more surface area for air to escape from the plug 6062, so as not to provide any unnecessary restrictions on the patient's breathing. The spaces may also provide more surface area for air to enter the plug 6062 and be inhaled by the patient (e.g., more inhaled air can be at least partially saturated).

In some forms, the linking member 6072 may be shaped (e.g., bent) to lie in contact with the rings 6058, 6060. This may assist in limiting or preventing contact between the linking member 6072 and the patient's nose (e.g., the patient's pronasale and/or columella). Positioning the linking member 6072 to lie in contact with the rings 6058, 6060 may also limit disturbances in airflow as the patient breathes.

5.7.3.2 Rectangular Cradle

FIGS. 13A-13C illustrate an HME 6000h that is a variation of the HME 6000d shown in FIGS. 12A-12D, and described above. Only some similarities and differences between the HME 6000g and the HME 6000h are described below.

The HME 6000h includes a frame 6004 and a cradle 6006. The frame 6004 may be partially ring shaped (e.g., a three-dimensional annulus sector), and include a first free end 6074 and a second free end 6076. The free ends 6074, 6076 may be spaced apart from one another so that the frame 6004 does not form a complete circle. In the illustrated example, each of the free ends 6074, 6076 have a spherical shape. The diameter of each free end 6074, 6076 may be slightly larger than a diameter of the remainder of the frame 6004. In other examples (not shown), the frame 6004 may have a similar shape to the frame shown in the HME 6000g (or the HME 6000g may have a frame similar to the frame shown in the HME 6000h).

The cradle 6006 is coupled to the frame 6004. In the illustrated example, the cradle 6006 and the frame 6004 are separate pieces, and are coupled together. Specifically, the cradle 6006 includes a clip 6078 that is configured to receive the frame 6004. The frame 6004 and the cradle 6006 may be coupled together using a snap-fit or other mechanical engagement (e.g., without using another fastener). The frame 6004 may also be pivotable relative to the clip 6078 when the two are coupled together.

In the illustrated example, the cradle 6006 is substantially rectangular in shape. Specifically, the cradle 6006 includes a posterior bar 6080 and an anterior bar 6082 that extend generally parallel to one another. In some examples, the posterior bar 6080 may include a slight curvature, which may substantially correspond to a curvature of the patient's lip superior. The cradle 6006 also includes outer support bars 6084, which extend parallel to each other and generally orthogonally with respect to the posterior and anterior bars 6080, 6082. The cradle 6006 further includes a central support bar 6086 that is generally parallel to the outer support bars 6084. The clip 6078 may be formed on the central support bar 6086. Together, the outer support bars 6084, the posterior bar 6080, and the anterior bar 6082 may form a breathing area BA.

In one form, the outer support bars 6084 and the anterior bar 6082 extends in the superior direction, and partially form a volume of the cradle 6006. The central support bar 6086 may also extend in the superior direction. The heights of each of these bars 6082, 6084, 6086 may be substantially the same. The height of the central support bar 6086 may also be slightly less than the heights of the outer support bars 6084 and the anterior bar 6082.

The HME material 6002 is coupled to the cradle 6006 and substantially covers the breathing area BA. A single sheet of HME material 6002 (see e.g., FIG. 13A) or multiple sheets of HME material (see e.g., FIG. 13B) may be coupled to the cradle 6006. In either case, the central support bar 6086 assists in supporting the sheet(s) of HME material 6002.

In one form, the HME material 6002 may have a thickness substantially the same as the height of the bars 6082, 6084, 6086. In other words, the HME material 6002 may extend to a top of the respective bars 6082, 6084, 6086, and may be flush with an upper surface of the bars 6082, 6084, 6086.

In one form, a thickness of the HME material 6002 is less than the height of the bars 6082, 6084, 6086. An upper surface of the HME material 6002 is inferior to the upper surface of the bars 6082, 6084, 6086, so that the HME material 6002 is within the volume defined by the bars 6082, 6084, 6086.

As shown in FIG. 13C, the HME 6000h is coupled to the patient's nose. The free ends 6074, 6076 of the frame 6004 are positioned within the patient's nose, and contact the patient's septum. The curvature of the frame 6004 may limit the contact with the subnasale, in order to reduce irritation experienced by the patient. The rounded surface of the free ends 6074, 6076 (e.g., spherical surface) limits any jagged surfaces from contacting and irritating the patient's nose, which may assist in improving patient compliance. The frame 6004 may be pivotable relative to the cradle 6006 in order to adjust the relative angle between them. This may help patients with different shaped noses find the correct fit. Pivoting the cradle 6006 relative to the frame 6004 may also assist the patient in spacing the cradle 6006 apart from the subnasale and/or lip superior. In other words, the patient may make slight adjustments to an angle between the frame 6004 and the cradle 6006 in order to reduce discomfort (e.g., from direct contact) experienced by the patient. This angular adjustment may be small (e.g., less than 3°) so that the HME 6000h maintains its low profile. For example, the shape and position of the plenum chamber 3200 may constrain the total angular movement of the cradle 6006, but may not entirely prevent some angular adjustment.

The free ends 6074, 6076 may grip the patient's septum to provide a frictional force that opposes the force of gravity. In other words, gravity may pull the HME 6000h in the inferior direction, and the frictional force caused by the free ends 6074, 6076 gripping the septum may retain the HME 6000h in the in use position. When the patient is sleeping, his specific sleeping position may affect the total frictional force needed to retain the HME 6000h in position. For example, when the patient is sleeping on his back, the gravitational force is directed into the patient's face and is helping to retain the HME 6000h in position (e.g., even without considering the effects of friction). Alternatively, the force of gravity is directed away from a patient who sleeps on his stomach. Therefore, the frictional force would oppose the gravitational force and keep the HME 6000h properly positioned. Because gravity assists in maintaining the HME 6000h in the in use position for a back-sleeping patient, some patients may find that position to be more comfortable. However, the light weight of the HME 6000h may not require a substantial frictional force to oppose the force of gravity, so the patient may be able to comfortably wear the HME 6000h while in a different sleeping position.

The cradle 6006 extends laterally beyond the patient's nares in order to limit the breathable gas that passes around the cradle 6006. When the HME material 6002 is substantially the same height as the bars 6082, 6084, 6086, the HME material 6002 is positioned closer to the patient's nares, and may assist in capturing additional water vapor (e.g., because the distance of travel from the HME material 6002 to the patient's nares is reduced). When the HME material 6002 is inferior to the top surface of the bars 6082, 6084, 6086, the volumed formed by the bars 6082, 6084, 6086 may assist in directing exhaled air into the HME material 6002. Since the HME material 6002 is further away, the bars 6082, 6084, 6086 help to limit the amount of exhaled gas that escapes around the cradle 6006.

5.7.3.3 Curved Cradle

FIGS. 14A-14E illustrate an HME 6000i that is a variation of the HME 6000g and the HME 6000h, both of which are described above. Only some similarities and differences between the HMEs 6000g, 6000h and the HME 6000i are described below.

The HME 6000i includes a frame 6004 and a cradle 6006. The frame 6004 may be partially ring shaped (e.g., a three-dimensional annulus sector, and include a first free end 6074 and a second free end 6076. The free ends 6074, 6076 may be spaced apart from one another so that the frame 6004 does not form a complete circle. In the illustrated example, each of the free ends 6074, 6076 have a spherical shape. The frame 6004 of the HME 6000i and the HME 6000h may be substantially the same size.

The cradle 6006 is coupled to the frame 6004. In the illustrated example, the cradle 6006 and the frame 6004 are separate pieces, and are coupled together. Specifically, the cradle 6006 includes a clip 6078 that is configured to receive the frame 6004. The frame 6004 and the cradle 6006 may be coupled together using a snap-fit or other mechanical engagement (e.g., without using another fastener). The frame 6004 may also be pivotable relative to the clip 6078 when the two are coupled together.

In the illustrated example, the cradle 6006 includes a curved surface (e.g., a positively curved surface). A lower edge 6088 of the cradle 6006 is substantially straight, and an upper edge 6090 of the cradle is curved. For example, the upper edge 6090 is convex with respect to the lower edge 6088. The lower edge 6088 may also be longer than the upper edge 6090. A pair of openings 6092 are disposed within the curved surface of the cradle 6006. The clip 6078 may be positioned between the pair of openings 6092.

In some forms, the cradle 6006 may be constructed from a rigid or semi-rigid material in order to assist in maintaining the shape of the cradle 6006. For example, the rigid or semi-rigid material may assist in maintaining a curvature without use of an outside force.

In certain forms, the cradle 6006 may be at least partially flexible so that the patient may customize the shape of the cradle 6006. For example, the patient may flex the cradle 6006 in order to change the curvature (e.g., to make the curvature more or less positive). This may allow the patient to shape the cradle to better fit their individual face. Once the patient has bent the cradle 6006 to the desired shape, the cradle 6006 may stay in the new shape without any additional force.

The HME material 6002 is coupled to the cradle 6006 and substantially covers the pair of openings 6092. Multiple sheets of HME material (see e.g., FIG. 14A), a single sheet of HME material 6002 (see e.g., FIG. 14B), or plugs 6062 of HME material (see e.g., FIG. 14C) may be coupled to the cradle 6006. In any of these cases, the pair of openings 6092 are completely covered by the various shapes of the HME material 6002.

In some forms, the multiple sheets of HME material and/or the single sheet of HME material may be removably connected to the cradle 6006. For example, the sheet(s) of HME material may include an adhesive in order to stick to the cradle 6006 and remain in place over the openings 6092. After one or more uses, the patient may remove the sheet(s) of HME material and connect a new sheet of HME material of the cradle 6006. Alternatively, the patient may clean and replace the existing sheet(s) of HME material.

In some forms, plugs 6062 may be coupled to the cradle 6006 in a similar manner as described above with respect to the cradle 6006 in the ring HME 6000g (see e.g., FIG. 12B). For example, the plugs 6062 may be inserted into the respective compartments 6070, and the holder 6068 may be inserted through the openings 6092. The linking member 6072 may be positioned close to or in contact with the cradle 6006. This may limit discomfort as a result of the linking member 6072 caused by wearing the cradle 6006 (e.g., because the linking member 6072 may be shaped by the patient to avoid uncomfortable contact with the patient's columella).

The linking member 6072 may keep the plugs 6062 connected to the cradle 6006 and prevent disconnection as a result of the force of gravity. In other words, gravity may pull the holder 6068 and the plugs 6062 in the inferior direction. The linking member 6072 may be pulled into the solid surface of the cradle 6006 and prevented from completely passing through the openings 6092.

In the illustrated example, the plugs 6062 may be recessed from the superior surface 6094 of the cradle 6006. In other words, the first ends 6064 of the plugs 6062 and the compartments 6070 may not be flush with the superior surface 6094 of the cradle 6006. Instead, the first ends 6064 of the plugs 6062 may be spaced apart from the patient's nares in the inferior direction, in use. This may limit impedance when the patient exhales, but may still allow the exhaled (and inhaled) air to pass through the plugs 6062. In other examples, the first ends 6064 of the plugs 6062 may be at least partially flush with the superior surface 6094 of the cradle 6006, of the plugs 6062 may protrude beyond the superior surface 6094 of the cradle 6006 (e.g., superior to the superior surface 6094 in use). However, even if the plugs 6062 protrude beyond the superior surface 6094, the plugs 6062 still may not enter the patient's nares in use (and create added impedance while breathing).

As shown in FIGS. 14D and 14E, the HME 6000i is coupled to the patient's nose. Specifically, the free ends 6074, 6076 of the cradle 6006 (see e.g., FIG. 14A) are positioned within the patient's nares, and coupled to a respective side of the patient's septum. The free ends 6074, 6076 may grip the patient's septum to provide a frictional force that opposes the force of gravity. In other words, gravity may pull the HME 6000i in the inferior direction, and the frictional force caused by the free ends 6074, 6076 gripping the septum may retain the HME 6000i in the in use position. When the patient is sleeping, his specific sleeping position may affect the total frictional force needed to retain the HME 6000i in position. For example, when the patient is sleeping on his back, the gravitational force is directed into the patient's face and is helping to retain the HME 6000i in position (e.g., even without considering the effects of friction). Alternatively, the force of gravity is directed away from a patient who sleeps on his stomach. Therefore, the frictional force would oppose the gravitational force and keep the HME 6000i properly positioned. Because gravity assists in maintaining the HME 6000i in the in use position for a back-sleeping patient, some patients may find that position to be more comfortable. However, the light weight of the HME 6000i may not require a substantial frictional force to oppose the force of gravity, so the patient may be able to comfortably wear the HME 6000i while in a different sleeping position.

The cradle 6006 has a concave or positive curvature with respect to the patient's nose, and is positioned proximate to the patient's nose. In the illustrated example, the cradle 6006 may contact a portion of the patient's nose (e.g., the pronasale). In other examples, the cradle 6006 may be slightly spaced apart from the patient's nose (e.g., less than two inches, less than one inch, etc.). The cradle 6006 is positioned so that the lower edge 6088 is positioned proximate to the patient's lip superior, and that the upper edge 6090 is positioned proximate to the patient's pronasale. For example, the HME 6000i may extend through the nasolabial angle in order to form a triangular region defined by the HME 6000i and the lines forming the nasolabial angle (see e.g., FIG. 2E). The concave (e.g., positive) curvature of the upper edge 6090 may assist in curving around the patient's pronasale (e.g., to avoid contact and associated irritation).

The pair of openings 6092 (and the HME material 6002 covering the openings 6092), may be substantially aligned with the patient's nares. Exhaled air may be directed directly onto the HME material 6002. Additionally, the distance between the HME material 6002 and the patient's nares assists in increasing the amount of water vapor retained by the HME 6000i. Since the cradle 6006 is so close to the nose, and because the cradle 6006 curves around the patient's nose, substantially all of the exhaled air is directed into the HME material 6002, and very little is allowed to escape around the edges of the cradle 6006. Positioning the cradle 6006 very close to the patient's nose and curving the cradle 6006 around the patient's nose contributes to a low profile for the HME 6000i. With specific reference to FIG. 14D, very little of the HME 6000i extends beyond the nose, since the HME 6000i is sufficiently thin, and the cradle 6006 curves to substantially correspond to a shape of the patient's nose. This low profile may assist in patient compliance because the patient may be unable to see that they are wearing a medical device.

As shown in FIG. 14E, the HME 6000i utilizing the plugs 6062 may include a larger profile as compared to the HME 6000i using the sheets of HME material 6002. However, the plugs 6062 may not extend significantly beyond the surface of the cradle 6006 in order to maintain a low profile. For example, the plugs 6062 may not contact the patient interface 3000 in use, thereby limiting any discomfort caused by inadvertent contact between the plugs 6062 and the plenum chamber 3200.

5.7.4 Adhesive Against Nose

In certain forms (see e.g., FIGS. 15A-15C), an HME 6000j is coupled to the patient's nose on an outer surface of the patient's nares. The HME 6000j may include only a cradle 6006 that is coupled directly to the patient's nose. In other words, the HME 6000j does not include a frame.

In one form, the cradle 6006 of the HME 6000j has substantially the same shape as the frame 6004 of the HME 6000i. For example, the cradle 6006 includes a curved surface. A lower edge 6088 of the cradle 6006 is substantially straight, and an upper edge 6090 of the cradle is curved. For example, the upper edge 6090 is convex with respect to the lower edge 6088. The lower edge 6088 may also be longer than the upper edge 6090. The cradle 6006 may be constructed from a flexible or semi-rigid material (e.g., plastic, textile, etc.), and may be bendable into different positions. The cradle 6006 may also be constructed in a standard shape (e.g., a circle, a rectangle, etc.), and may be trimmed by the patient and/or the clinician in order to achieve a desired shape.

As shown in FIG. 15B, layers of HME material 6002 may be coupled to the cradle 6006. In the illustrated example, pieces of HME material 6002 are stacked onto one another. This may increase the impedance of the HME material 6002, and increase the amount of moisture than is captured by the HME 6000j. Any number of layers of HME material 6002 may be used, and the layer(s) may cover any area on the cradle 6006. However, it may be desirable for the HME material 6002 to only cover an area of the cradle 6006 that will directly cover the patient's nares. In other words, it may not be necessary to include HME material 6002 in areas that are laterally outside of the patient's nares.

An outer portion of the cradle 6006 may be an adhesive region 6020, or an adhesive may be applied to the cradle 6006 radially outside of where the HME material 6002 is applied. The adhesive is used to secure the cradle to the patient's nose. The adhesive may be biocompatible so that it does not negatively interact with the skin while it is applied. The adhesive is also easy to remove so that it does not cause substantive damage to the patient's skin.

As shown in FIG. 15C, the cradle 6006 of the HME 6000j is positioned against the patient's nose in a substantially similar manner as the cradle 6006 of the HME 6000i. The cradle 6006 wraps around the patient's nose so that the adhesive region 6020 is coupled to sides of the patient's nose. The cradle 6006 may be constructed from a permeable material in order to let inhaled and exhaled air pass through. Alternatively or in addition, hole(s) may be cut into the cradle 6006 proximate to the HME material 6002 in order to allow airflow through the cradle 6006.

The HME 6000j is coupled directly to the patient's nose and does not substantially extend away from the patient's nose. This creates a substantially low profile. The HME 6000j also does not include a piece that pinches the nose (e.g., either inside the nose or outside the nose), which a patient may find comfortable and improve patient compliance.

The adhesive may be strong enough in order to oppose the force of gravity and maintain the in use position of the HME 6000j. In other words, the adhesive force between the cradle 6006 and the patient's skin is greater than the gravitational force acting on the HME 6000j.

5.7.5 Wearing the Heat and Moisture Exchanger

Once any of the above HMEs 6000 described above are coupled to the patient's nose, the patient may don a patient interface 3000. The HME 6000 is independently supported against the patient's nose (e.g., using any one of the above mechanisms), and remains in the appropriate place on the patient's nose without an additional force provided by the patient. In other words, the patient may have both hands free to don the patient interface 3000 because the HME 6000 is already connected and in place.

Different types or styles of patient interfaces 3000 may be worn by a patient wearing an HME 6000. For example, the patient interface 3000 may have a positioning and stabilizing structure 3300 that is also conduit headgear (see e.g., FIG. 16A). Alternatively, the patient interface 3000 may have the connection port 3600 on the plenum chamber 3200 so that the air circuit 4170 extends away from the patient's face (see e.g., FIG. 16B). In this example, the positioning and stabilizing structure 3300 does not convey airflow to the plenum chamber 3200. However, in some forms, the patient interface 3000 utilizing the connection port 3600 (e.g., FIG. 16B) may still use tubes 3302 that do not convey air to provide a sealing force for the seal-forming structure 3100. In other forms, the tubes 3302 may be replaced with textile straps 3310 when the connection port 3600 is used to convey air into the plenum chamber 3200.

The low profile of the HME 6000 also assists the patient with donning (or doffing) the patient interface 3000. For example, if the HME 6000 does not substantially protrude from the patient's nose, the patient does not have another obstruction to avoid while attempting to properly position the plenum chamber 3200. Additionally, the low profile of the HME 6000 helps to maintain a space with the plenum chamber 3200, so that the plenum chamber 3200 does not contact the HME 6000, and provide a force directed into the patient's nose while in the therapeutically effective position. This assists in providing optimal comfort for a patient wearing the HME 6000, and therefore increasing patient compliance.

As shown in FIGS. 17A and 17B, once the patient interface 3000 is donned on the patient's head, the HME 6000 is positioned within the plenum chamber 3200. The low profile of the HME 6000 allows many different styles of plenum chambers 3200 to be used. In other words, a special plenum chamber 3200 does not need to be designed for use with the HME 6000.

As shown in FIGS. 18A and 18B, when the RPT device 4000 is active and pressurized breathable gas is flowing into the plenum chamber 3200, the airflow is directed into the HME 6000. For example, FIG. 18A illustrates that each tube 3302 of the conduit headgear supplies airflow into the plenum chamber 3200 to a lateral side of the HME 6000. An entrance 3304 from the tube 3302 into the plenum chamber 3200 may be inferior to the HME 6000, but may be directed in a superior direction. The airflow may also be directed in a posterior direction (e.g., toward the patient). This causes the airflow to be directed up and into the HME 6000, and toward the patient's nose. The paths of the airflow may be directed into the HME material 6002, so that the airflow may pick up any moisture captured by the HME material 6002, before delivering the pressurized breathable gas to the patient's airways. Similarly, FIG. 18B illustrates that the connection port 3600 is inferior to the HME 6000, but directs the airflow in a superior and posterior direction in order to flow through the HME material 6002.

As shown in FIGS. 19A and 19B, breathable gas flowing into the plenum chamber 3200 is similarly directed into the HME 6000. Similar to FIG. 18A, FIG. 19A illustrates the tubes of the conduit headgear supplying airflow into the plenum chamber 3200 on the lateral side of the HME 6000. Although an entrance 3304 from the tube 3302 may be inferior to the cradle 6006, the plugs 6062 in the holder 6068 also extend in the inferior direction (as viewed in FIG. 19A). This may cause a greater portion if airflow (e.g., as compared to the example in FIG. 18A) to be directed into the HME material (i.e., the plugs 6062). Also, directing the airflow from the entrance 3304 in the superior direction may direct the airflow toward the first end 6064 of the plug 6062, which has a larger surface area. Allowing more airflow to pass into the HME material may improve the efficiency of the HME 6000. The airflow entering the plenum chamber 3200 may be able to pick up a greater portion of exhaled moisture trapped in the plugs 6062, and return that moisture to the patient's airways. Similarly, FIG. 19B illustrates that the connection port 3600 is inferior to the HME 6000, but directs the airflow in a superior and posterior direction in order to flow through the HME material 6002. Like in FIG. 19A, the plugs 6062 extend away from the patient's nose in the inferior direction (e.g., as viewed in FIG. 19B) so that the airflow from the connection port 3600 is directed into the plugs 6062 in order to increase the efficiency of the HME 6000 (e.g., as compared to the HME 6000 in FIG. 18B).

5.8 Breathing Waveforms

FIG. 5 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.9 Portable Oxygen Concentrator (POC)

Portable oxygen concentrators may take advantage of pressure swing adsorption (PSA). Pressure swing adsorption may involve using one or more compressors to increase gas pressure inside a canister that contains particles of a gas separation adsorbent arranged in a "sieve bed". As the pressure increases, certain molecules in the gas may become adsorbed onto the gas separation adsorbent. Removal of a portion of the gas in the canister under the pressurized conditions allows separation of the non-adsorbed molecules from the adsorbed molecules. The gas separation adsorbent may be regenerated by reducing the pressure, which reverses the adsorption of molecules from the adsorbent. Further details regarding oxygen concentrators may be found, for example, in U.S. Published Patent Application No. 2009-0065007, published Mar. 12, 2009, and entitled "Oxygen Concentrator Apparatus and Method", which is incorporated herein by reference.

Ambient air usually includes approximately 78% nitrogen and 21% oxygen with the balance comprised of argon, carbon dioxide, water vapor and other trace gases. If a gas mixture such as air, for example, is passed under pressure through a canister containing a gas separation adsorbent bed that attracts nitrogen more strongly than it does oxygen, part or all of the nitrogen will stay in the bed, and the gas coming out of the canister will be enriched in oxygen. When the bed reaches the end of its capacity to adsorb nitrogen, it can be regenerated by reducing the pressure, thereby releasing the adsorbed nitrogen. It is then ready for another cycle of producing oxygen enriched air. By alternating canisters in a two-canister system, one canister can be separating oxygen while the other canister is being purged (resulting in a continuous separation of the oxygen from the nitrogen). In this manner, oxygen enriched air can be accumulated, such as in a storage container or other pressurizable vessel or conduit coupled to the canisters, for a variety of uses including providing supplemental oxygen to patients.

5.10 Glossary

For the purposes of the present technology disclosure, in certain forms of the present technology, one or more of the following definitions may apply. In other forms of the present technology, alternative definitions may apply.

5.10.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal (1 hectopascal=100 Pa=100 $N/m^2$=1 millibar ~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.10.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240

Polycarbonate: a thermoplastic polymer of Bisphenol-A Carbonate.

5.10.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cm1H_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.10.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
  (i) Flattened: Having a rise followed by a relatively flat portion, followed by a fall.
  (ii) M-shaped: Having two local peaks, one at the leading edge, and one at the trailing edge, and a relatively flat portion between the two peaks.
  (iii) Chair-shaped: Having a single local peak, the peak being at the leading edge, followed by a relatively flat portion.
  (iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
  (i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peakflow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.10.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (SIT): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator, or other respiratory therapy device such as an RPT device or portable oxygen concentrator, delivers a volume of breathable gas to a spontaneously breathing patient, it is said to be triggered to do so. Triggering usually takes place at or near the initiation of the respiratory portion of the breathing cycle by the patient's efforts.

5.10.4 Anatomy 5.10.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bonyframework: The bony framework of the nose comprises the nasal bones, the frontal process of the maxillae and the nasal part of the frontal bone.

(nose) Cartilaginousframework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labialfold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.10.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.10.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.10.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.10.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.10.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.10.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.10.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.10.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.11 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology. 5.12 REFERENCE SIGNS LIST

| | |
|---|---|
| patient | 1000 |
| bed partner | 1100 |
| ground electrode ISOG | 2010 |
| EOG electrode | 2015 |
| EEG electrode | 2020 |
| ECG electrode | 2025 |
| submental EMG electrode | 2030 |
| snore sensor | 2035 |
| movement sensor | 2040 |
| respiratory inductance plethysmogram | 2045 |
| respiratory effort sensor | |
| oro-nasal cannula | 2050 |
| pulse oximeter | 2055 |
| body position sensor | 2060 |
| patient interface | 3000 |
| seal-forming structure | 3100 |
| plenum chamber | 3200 |
| chord | 3210 |
| superior point | 3220 |
| inferior point | 3230 |
| plug | 3250 |
| positioning and stabilizing structure | 3300 |
| hollow tube | 3302 |
| entrance | 3304 |
| tab | 3306 |
| rear strap | 3308 |
| front strap | 3310 |
| vent | 3400 |
| decoupling structure | 3500 |
| connection port | 3600 |
| forehead support | 3700 |
| ISO | 3744 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| ring | 4171 |
| supplementary gas | 4180 |
| electrical components | 4200 |
| single Printed Circuit Board Assembly PCBA | 4202 |
| power supply | 4210 |
| input device | 4220 |
| transducer | 4270 |
| humidifier | 5000 |
| heat and moisture exchanger (HME) | 6000 |
| HME material | 6002 |
| corrugated paper | 6002A |
| foam | 6002B |
| frame | 6004 |
| cradle | 6006 |
| first superior bar portion | 6008 |
| second superior bar portion | 6010 |
| first inferior bar portion | 6012 |
| second superior bar portion | 6014 |
| posterior bar portion | 6016 |
| anterior bar portion | 6018 |
| adhesive region | 6020 |

-continued

| | |
|---|---|
| support bar portion | 6022 |
| first arm | 6024 |
| second arm | 6026 |
| loop | 6028 |
| lateral arm portions | 6030 |
| anterior arm portion | 6032 |
| first connector arm | 6034 |
| second connector arm | 6036 |
| posterior arm | 6038 |
| anterior arm | 6040 |
| outer support arms | 6042 |
| central support arm | 6044 |
| posterior arm | 6046 |
| first free end | 6048 |
| second free end | 6050 |
| inferior portion | 6052 |
| S-shaped portion | 6054 |
| seating surface | 6056 |
| first ring | 6058 |
| second ring | 6060 |
| plug | 6062 |
| first end | 6064 |
| second end | 6066 |
| holder | 6068 |
| compartment | 6070 |
| linking member | 6072 |
| first free end | 6074 |
| second free end | 6076 |
| clip | 6078 |
| posterior bar | 6080 |
| anterior bar | 6082 |
| outer support bars | 6084 |
| central support bar | 6086 |
| lower edge | 6088 |
| upper edge | 6090 |
| openings | 6092 |
| pipe | 7000 |
| airflow | 7002 |
| airflow | 7004 | patient 1000 bed partner 1100 ground electrode ISOG 2010

The invention claimed is:

1. A heat and moisture exchanger (HME) configured to engage the patient's nose while retrofitted into a plenum chamber of a patient interface, the HME comprising,
    a frame comprising a pair of superior bar portions joined together at a joint such that the joint is proximal to a ridge of the patient's nose in use, the frame comprising a pair of inferior bar portions, each of the inferior bar portions joined to an end of a corresponding one of the superior bar portions opposite the joint;
    a cradle coupled to the inferior bar portions and configured to be positioned proximate to the patient's nares, in use; and
    an HME material coupled to the cradle, the HME material configured to retain moisture exhaled by the patient;
    wherein the HME material is configured to allow air to pass through the HME material when entering and exiting the patient's nares;
    wherein the frame is configured to engage and secure to the patient's nose independently of any other structure; and
    wherein the frame and the cradle form a shape configured to complement a shape of the plenum chamber.

2. The HME of claim 1, wherein each of the inferior bar portions of the frame is inwardly biased and configured to clamp against a surface of the patient's nose.

3. The HME of claim 1, wherein the cradle includes a positive curvature with respect to an entrance of the patient's nares in use.

4. The HME of claim 1, wherein the cradle is configured to be disposed substantially orthogonal with respect to the patient's upper lip.

5. The HME of claim 1, wherein the cradle is flexible or semi-rigid and configured to be adjusted by a patient to change the shape of the cradle.

6. The HME of claim 1, wherein the HME material is removable from the cradle.

7. The HME of claim 1, wherein the HME material is permanently affixed to the cradle.

8. The HME of claim 1, wherein the HME material is configured to allow exhaled air to pass through so that at least some moisture in the exhaled air is collected in the HME material.

9. The HME of claim 1, wherein the HME material is configured to be spaced apart from the patient's nares so that at least one flow path of air configured to travel into or out of the patient's nares does not travel through the HME material.

10. The HME of claim 1, wherein the cradle includes a first cradle section and a second cradle section, and
    wherein the HME material includes a first HME material section and a second HME material section that covers each of the first cradle section and the second cradle section, respectively.

11. The HME of claim 10, wherein the first cradle section is spaced apart from the second cradle section.

12. The HME of claim 1, wherein the HME material is foam and/or paper.

13. The HME of claim 1, wherein the cradle further includes a posterior bar shaped with a curvature configured to be substantially similar to the patient's upper lip.

14. The HME of claim 13, wherein the HME further includes a middle bar connected to the cradle and the posterior bar, the middle bar supporting the HME material.

15. The HME of claim 1, wherein the HME material is coupled to the cradle with an adhesive.

16. The HME of claim 1, further comprising a gauze material configured to be disposed between the HME material and the patient's skin.

17. The HME of claim 16, wherein the gauze material is coupled to the HME material with an adhesive.

18. The HME of claim 1, wherein the HME material is removable from the cradle such that the HME material is disposable after a single use, and the cradle is reusable.

19. The HME of claim 1, wherein the cradle is configured to be secured to the patient without adhesive.

20. A patient interface in combination with the HME of claim 1, the patient interface comprising:
    the plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;
    a seal-forming structure comprising a seal, the seal-forming structure being constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use; and a positioning and stabilizing structure comprising at least one strap, the positioning and stabilizing structure being configured to provide a force to hold the seal-forming structure in a therapeutically effective position on a patient's head, wherein the frame and the cradle are shaped to complement a shape of the plenum chamber such that the HME fits within the plenum chamber during use.

21. The patient interface of claim 20, wherein the shape formed by the frame and the cradle and the shape of the plenum chamber have similar curvature.

22. The patient interface of claim 20, wherein the HME material is configured to allow at least a portion of a flow of air entering the plenum chamber through the plenum chamber inlet port to pass through the HME material prior to reaching the patient's nares.

23. A heat and moisture exchanger (HME) configured to engage the patient's nose while retrofitted into a plenum chamber of a patient interface, the HME comprising, a cradle configured to be positioned proximate to the patient's nares, in use, the cradle including at least one opening;

a frame comprising a pair of elongate members, each of the elongate members connected to a corresponding lateral portion of the cradle at a first end, each of the elongate members having a second end opposite the first end, the second end being a free end, and a portion between the first end and the second end of each of the elongate members extending towards the opposite lateral side of the cradle to couple to a corresponding lateral portion of the patient's nose in use; and an HME material coupled to the cradle covering the opening and configured to be spaced apart from the patient's nares so as to form a gap between the HME material and the patient's nares;

wherein the HME is configured to engage and secure to the patient's nose independently of any other structure; and wherein the frame and the cradle form a shape configured to complement a shape of the plenum chamber; and wherein the opening is configured to allow inhaled and exhaled air to pass through the opening and the HME material.

24. The HME of claim 23, wherein the frame is configured to be coupled to a ridge of the patient's nose.

25. The HME of claim 23, wherein the elongate members of the frame are configured to be positioned adjacent to the lateral nasal cartilage and/or to the greater alar cartilage of the patient's nose.

26. The HME of claim 23, wherein the elongate members of the frame are shaped like an annulus sector, and are configured to engage a septum of the patient's nose.

27. The HME of claim 26, wherein the frame is pivotable relative to the cradle.

28. The HME of claim 26, wherein each of the elongate members of the frame is curved to substantially corresponds to a curvature of the patient's columella.

29. The HME of claim 26, wherein the cradle is ring shaped.

30. The HME of claim 29, wherein the HME material is formed as a plug, the HME further comprising a holder configured to removably receive the plug, and wherein the holder is removably received within the cradle.

31. The HME of claim 30, wherein the plug has a conical shape, a frustoconical shape, or a cylindrical shape.

32. The HME of claim 23, wherein each of the elongate members of the frame is configured to be coupled to a corresponding nasal ala of the patient's nose.

33. The HME of claim 23, wherein the cradle is configured to extend from the upper lip to the pronasale in use.

34. The HME of claim 33, wherein the cradle is configured to extend generally parallel with respect to the patient's upper lip in use, the cradle configured to extend from the pronasale to the patient's lower lip in use so that at least some air entering and/or exiting the patient's mouth passes through the HME material.

35. A patient interface comprising:

a plenum chamber pressurisable to a therapeutic pressure of at least 6 cmH2O above ambient air pressure, said plenum chamber including a plenum chamber inlet port sized and structured to receive a flow of air at a therapeutic pressure for breathing by a patient;

a seal-forming structure comprising a seal, the seal-forming structure being constructed and arranged to form a seal with a region of a patient's face surrounding an entrance to a patient's airways for sealed delivery of a flow of air at the therapeutic pressure of at least 6 cmH2O above ambient air pressure throughout a patient's respiratory cycle in use, said seal-forming structure having a hole therein such that the flow of air at said therapeutic pressure is delivered to at least an entrance to a patient's nares, the seal-forming structure constructed and arranged to maintain said therapeutic pressure in the plenum chamber throughout the patient's respiratory cycle in use;

a positioning and stabilizing structure comprising at least one strap, the positioning and stabilizing structure being configured to provide a force to hold a seal-forming structure in a therapeutically effective position on a patient's head; and a heat and moisture exchanger (HME) configured to be coupled to the patient's nose in use as a retrofit, the HME comprising, a cradle including at least one opening, an HME material coupled to the cradle such that, in use, the HME material does not contact the patient's nares, the HME material covering the opening, and a pair of elongate members, each of the elongate members connected to a corresponding lateral portion of the cradle at a first end, each of the elongate members having a second end opposite the first end, the second end being a free end, and a portion between the first end and the second end of each of the elongate members extending towards the opposite lateral side of the cradle to couple to a corresponding lateral portion of the patient's nose in use, and wherein the cradle has a shape complementing a shape of the plenum chamber in order to fit at least partially inside of the plenum chamber; and wherein the opening is configured to allow inhaled and exhaled air to pass through the opening and the HME material.

* * * * *